United States Patent
Tung et al.

(10) Patent No.: US 9,265,844 B2
(45) Date of Patent: Feb. 23, 2016

(54) PROTEASE DEGRADABLE POLYPEPTIDES AND USES THEREOF

(75) Inventors: Ching-Hsuan Tung, Houston, TX (US); Wael R. Abd-Elgaliel, Houston, TX (US); Craig D. Logsdon, Houston, TX (US); Zobeida Cruz-Monserrate, Houston, TX (US)

(73) Assignees: THE METHODIST HOSPITAL SYSTEM, Houston, TX (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 13/990,866

(22) PCT Filed: Dec. 1, 2011

(86) PCT No.: PCT/US2011/062817
§ 371 (c)(1),
(2), (4) Date: May 31, 2013

(87) PCT Pub. No.: WO2012/075241
PCT Pub. Date: Jun. 7, 2012

(65) Prior Publication Data
US 2013/0251640 A1  Sep. 26, 2013

Related U.S. Application Data

(60) Provisional application No. 61/418,661, filed on Dec. 1, 2010.

(51) Int. Cl.
*A61B 5/00* (2006.01)
*A61B 8/00* (2006.01)
*A61B 10/00* (2006.01)
*C12Q 1/37* (2006.01)
*A61K 38/04* (2006.01)
*C07K 5/00* (2006.01)
*C07K 7/00* (2006.01)
*C07K 16/00* (2006.01)
*C07K 17/00* (2006.01)
*A61K 49/00* (2006.01)
*A61K 47/48* (2006.01)
*G01N 33/533* (2006.01)
*G01N 33/542* (2006.01)
*G01N 33/574* (2006.01)
*G01N 21/64* (2006.01)
*C12N 15/11* (2006.01)
(Continued)

(52) U.S. Cl.
CPC ....... *A61K 49/0045* (2013.01); *A61K 47/48238* (2013.01); *A61K 47/48861* (2013.01); *A61K 49/0039* (2013.01); *A61K 49/0056* (2013.01); *C12N 15/111* (2013.01); *C12Q 1/37* (2013.01); *G01N 21/6486* (2013.01); *G01N 33/533* (2013.01); *G01N 33/542* (2013.01); *G01N 33/574* (2013.01); *A61K 38/00* (2013.01); *A61K 48/00* (2013.01); *C12N 2310/14* (2013.01); *C12N 2320/32* (2013.01); *G01N 2800/52* (2013.01)

(58) Field of Classification Search
CPC .............. A61K 49/0045; A61K 38/00; A61K 47/48238; A61K 47/48861; A61K 48/00; A61K 49/0039; A61K 49/0056; G01N 21/6486; G01N 2800/52; G01N 33/533; G01N 33/542; G01N 33/574; C12N 15/111; C12N 2310/14; C12N 2320/32; C12Q 1/37
See application file for complete search history.

(56) References Cited

U.S. PATENT DOCUMENTS

| | | | |
|---|---|---|---|
| 6,083,486 | A | 7/2000 | Weissleder et al. |
| 6,592,847 | B1 | 7/2003 | Weissleder et al. |
| 2004/0067927 | A1 | 4/2004 | Boss et al. |

(Continued)

FOREIGN PATENT DOCUMENTS

| | | |
|---|---|---|
| EP | 582477 | 2/1994 |
| JP | 2005-117993 A | 5/2005 |

(Continued)

OTHER PUBLICATIONS

Azuma et al "Cathepsin E Expressedin Pancreatic Cancer" in Aspartic Proteinases: Structure, Function, Biology, and Biomedical Implications. p. 363-366. Published 1995.*

(Continued)

*Primary Examiner* — Christina Bradley
*Assistant Examiner* — Zachary J Miknis
(74) *Attorney, Agent, or Firm* — Kilpatrick Townsend & Stockton LLP

(57) ABSTRACT

Provided herein are polypeptides that are selectively cleaved by cathepsin E. Also provided are methods of detecting cathepsin E. The methods comprise contacting cathepsin E with the polypeptides provided herein and detecting fluorescence. Further provided are methods of diagnosing cancer or precancerous conditions in a subject. Also provided herein is a multilayered nanoparticle or a composition comprising the multilayer nanoparticle, wherein the multilayered nanoparticle comprises a negatively charged nanoparticle core or capsule coated with alternating positive and negative layers. Optionally, the positive layer comprises a positively charged protease degradable polypeptide. Optionally, the negative layer comprises a negatively charged therapeutic agent or a therapeutic agent and a means for providing the agent with a negative charge. For example, optionally, the therapeutic agent is linked to a negatively charged polymer. Further provided are methods of treating or preventing a disease characterized by expression of a protease in a subject using the nanoparticle.

42 Claims, 30 Drawing Sheets

(51) Int. Cl.
*A61K 48/00* (2006.01)
*A61K 38/00* (2006.01)

(56) References Cited

U.S. PATENT DOCUMENTS

| | | | |
|---|---|---|---|
| 2004/0102431 | A1 | 5/2004 | Boss et al. |
| 2006/0275775 | A1 | 12/2006 | Weissleder et al. |
| 2008/0076762 | A1 | 3/2008 | Boss et al. |
| 2009/0311193 | A1 | 12/2009 | Mauro et al. |
| 2010/0124757 | A1 | 5/2010 | Kwon et al. |
| 2012/0225425 | A1* | 9/2012 | Navari et al. ............ 435/6.11 |

FOREIGN PATENT DOCUMENTS

| | | |
|---|---|---|
| KR | 1020100026477 | 3/2010 |
| WO | WO 0073437 A1 * | 12/2000 |
| WO | 2009111470 | 9/2009 |
| WO | 2010024609 | 3/2010 |

OTHER PUBLICATIONS

AnaSpec, Inc. "FRET Technology the dawn of long wavelength protease FRET assays". 2nd Edition. Published 2008.*

Kokame K et al "FRETS-VWF73, a first fluorogenic substrate for ADAMTS12 assay" Brit. J. Haematology 129:93-100. Published 2005.*

Abd-Elgaliel et al., "Molecular imaging of Cathepsin E-positive tumors in mice using novel protease-activatable fluorescent probe", Molecular Biosystems, vol. 7, No. 12, Dec. 2011, pp. 3207-3213.

Abd-Elgaliel et al., "Selective Detection of Cathepsin E Proteolytic Activity", Biochimica et Biophysica Acta, vol. 1800, No. 9, Jun. 2010, pp. 1002-1008.

Al et al., "Biomedical applications of electrostatic layer-by-layer nano-assembly of polymers, enzymes, and nanoparticles", Cell Biochemistry and Biophysics, vol. 39, No. 1, 2003, pp. 23-43.

Amano et al., "Increased expression of cathepsins E and D in reactive microglial cells associated with spongiform degeneration in the brain stem of senescence-accelerated mouse", Experimental Neurology, vol. 136, No. 2, Dec. 1995, pp. 171-182.

AnaSpec, Inc. "FRET Technology the dawn of long wavelength protease FRET assays." 2nd Edition. Published 2008.

Anderson, C. J. et al., "AACR/SNMMI state-of-the-art molecular imaging in cancer biology and therapy: Abstracts," J Nucl Med, 2013, vol. 54, No. Supplement 1, pp. 3A-35.

Arumugam et al., "Epithelial to mesenchymal transition contributes to drug resistance in pancreatic cancer", Cancer Research, vol. 69, No. 14, Jul. 15, 2009, pp. 5820-5828.

Arvizo et al., "Effect of Nanoparticle Surface Charge at the Plasma Membrane and Beyond", Nano Letters, vol. 10, No. 7, Jul. 14, 2010, pp. 2543-2548.

Azuma et al., "Cathepsin E expressed in pancreatic cancer", Advances in Experimental Medicine and Biology, vol. 362, 1995, pp. 363-366.

Azuma et al., "Expression of cathepsin E in pancreas: a possible tumor marker for pancreas, a preliminary report", International Journal of Cancer, vol. 67, No. 4, Aug. 7, 1996, pp. 492-497.

Azuma et al., "Origins of the multiple cathepsin E transcripts observed in human gastric mucosa and gastric adenocarcinoma", Advances in Experimental Medicine and Biology, vol. 306, 1991, pp. 365-368.

Baechle et al., "Biotinylated fluorescent peptide substrates for the sensitive and specific determination of cathepsin D activity", Journal of Peptide Science, vol. 11, No. 3, Mar. 2005, pp. 166-174.

Bagalkot et al., "Quantum dot-aptamer conjugates for synchronous cancer imaging, therapy, and sensing of drug delivery based on bi-fluorescence resonance energy transfer", Nano Letters, vol. 7 No. 10, Sep. 14, 2007, pp. 3065-3070.

Bander et al., "Phase I trial of 177lutetium-labeled J591, a monoclonal antibody to prostate-specific membrane antigen, in patients with androgen-independent prostate cancer", Journal of Clinical Oncology, vol. 23, No. 21, Jul. 20, 2005, pp. 4591-4601.

Bardeesy et al., "Both p16(Ink4a) and the p19(Arf)-p53 pathway constrain progression of pancreatic adenocarcinoma in the mouse", Proceedings of the National Academy of Sciences of the USA, vol. 103, No. 15, Apr. 11, 2006, pp. 5947-5952.

Bartoli, M., Bourg, N. et al., "A mouse model for monitoring calpain activity under physiological and pathological conditions," J. Biol. Chem, 2006, vol. 281, No. 51, pp. 39672-39680.

Bausch et al., "Plectin-1 as a novel biomarker for pancreatic cancer", Clinical Cancer Research, vol. 17, No. 2, Jan. 15, 2010, pp. 302-309.

Bennett et al., "Antigen processing for presentation by class II major histocompatibility complex requires cleavage by cathepsin E", European Journal of Immunology, vol. 22, No. 6, Jun. 1992, pp. 1519-1524.

Benveniste et al., "Role of macrophages/microglia in multiple sclerosis and experimental allergic encephalomyelitis", Journal of Molecular Medicine, vol. 75, No. 3, Mar. 1997, pp. 165-173.

Berdowska et al., "Cysteine proteases as disease markers", Clinica Chimica Acta, vol. 342, No. 1-2, Apr. 2004, pp. 41-69.

Berlin, N.I. et al., "The metabolism of delta-aminolaevulic acid. 1. Normal pathways, studied with the aid of 15N," Biochem J, 1956, vol. 64, No. 1, pp. 80-90.

Bervar et al., "Invasiveness of transformed human breast epithelial cell lines is related to cathepsin B and inhibited by cysteine proteinase inhibitors", Biological Chemistry, vol. 384, No. 3, Mar. 2003, pp. 447-455.

Bird et al., "The effects of novel cathepsin E inhibitors on the big endothelin pressor response in conscious rats", Biochemical and Biophysical Research Communications, vol. 182, No. 1, Jan. 15, 1992, pp. 224-231.

Blaveri et al., "Bladder cancer outcome and subtype classification by gene expression", Clinical Cancer Research, vol. 11, No. 11, Jun. 1, 2005, pp. 4044-4055.

Bock et al., "Selection of single-stranded DNA molecules that bind and inhibit human thrombin", Nature, vol. 355, No. 6360, Feb. 6, 1992, pp. 564-566.

Bogdanov et al., "Cellular activation of the self-quenched fluorescent reporter probe in tumor microenvironment", Neoplasia, vol. 4, No. 3, May/Jun. 2002, pp. 228-236.

Bonetta, "RNA-based therapeutics: ready for delivery?", Cell, vol. 136, No. 4, Feb. 20, 2009, pp. 581-584.

Bown SG et al., "Photodynamic therapy for cancer of the pancreas," Gut, 2002, vol. 50, pp. 549-557.

Boyce, "Trial halted after gene shows up in semen", Nature, vol. 414, No. 6865, Dec. 13, 2001, p. 677.

Bremer et al., "In vivo molecular target assessment of matrix metalloproteinase inhibition", Nature Medicine, vol. 7, No. 6, Jun. 2001, pp. 743-748.

Brokx RD et al., "Designing peptide-based scaffolds as drug delivery vehicles," J Control Release, 2002, vol. 78, pp. 115-123.

Brown SB et al., "The present and future role of photodynamic therapy in cancer treatment," Lancet Oncol, 2004, vol. 5, pp. 497-508.

Bumcrot et al., "RNAi therapeutics: a potential new class of pharmaceutical drugs", Nature Chemical Biology, vol. 2, No. 12, Dec. 2006, pp. 711-719.

Busquets et al., "Cathepsin E is a specific marker of dysplasia in APC mouse intestine", Tumour Biology, vol. 27, No. 1, 2006, pp. 36-42.

Campo et al., "Cathepsin B expression in colorectal carcinomas correlates with tumor progression and shortened patient survival", American Journal of Pathology, vol. 145, No. 2, Aug. 1994, pp. 301-309.

Cartwright et al., "Cancer of the pancreas: are we making progress? A review of studies in the US Oncology Research Network", Cancer Control, vol. 15, No. 4, Oct. 2008, pp. 308-313.

Caruso et al., "Over-expression of cathepsin E and trefoil factor 1 in sessile serrated adenomas of the colorectum identified by gene expression analysis", Virchows Arch, vol. 454, No. 3, Mar. 2009, pp. 291-302.

Castanotto et al., "The promises and pitfalls of RNA-interference-based therapeutics", Nature, vol. 457, No. 7228, Jan. 22, 2009, pp. 426-433.

(56) References Cited

OTHER PUBLICATIONS

Celli JP et al., "Imaging and photodynamic therapy: mechanisms, monitoring, and optimization," Chem Rev, 2010, vol. 110, pp. 2795-2838.

Chain et al., "The Expression and Function of Cathepsin E in Dendritic Cells", The Journal of Immunology, vol. 174, No. 4, Feb. 15, 2005, pp. 1791-1800.

Chanana et al., "Interaction of polyelectrolytes and their composites with living cells", Nano Letters, vol. 5, No. 12, 2005, pp. 2605-2612.

Chang et al., "Lessons from Nature: microRNA-based shRNA libraries", Nature Methods, vol. 3, No. 9, Sep. 2006, pp. 707-714.

Chang et al., "Prostate-specific membrane antigen is produced in tumor-associated neovasculature", Clinical Cancer Research, vol. 5, No. 10, Oct. 1999, pp. 2674-2681.

Chari, "Detecting early pancreatic cancer: problems and prospects", Seminars in Oncology, vol. 34, No. 4, Aug. 2007, pp. 284-294.

Check, "A tragic setback", Nature, vol. 420, No. 6912, Nov. 14, 2002, pp. 116-118.

Chen et al., "In vivo imaging of proteolytic activity in atherosclerosis", Circulation, vol. 105, No. 23, Jun. 11, 2002, pp. 2766-2771.

Chen et al., "Near-infrared fluorescent imaging of matrix metalloproteinase activity after myocardial infarction", Circulation, vol. 111, No. 14, Apr. 12, 2005, pp. 1800-1805.

Cho, "Understanding the Role of Surface Charges in Cellular Adsorption versus Internalization by Selectively Removing Gold Nanoparticles on the Cell Surface with a I2/KI Etchant", Nano Letters, vol. 9, No. 3, Mar. 11, 2009, pp. 1080-1084.

Choi et al., "Selective Antitumor Effect of Novel Protease-Mediated Photodynamic Agent", Cancer Research, vol. 66, No. 14, Jul. 15, 2006, pp. 7225-7229.

Choi Y et al., "Conjugation of a photosensitizer to an oligoarginine-based cell-penetrating peptide increases the efficacy of photodynamic therapy," ChemMedChem, 2006, vol. 1, pp. 458-463.

Choi Y et al., "Protease-mediated phototoxicity of a polylysine-chlorin(E6) conjugate," ChemMedChem, 2006, vol. 1, pp. 698-701.

Chu et al., "Aptamer: toxin conjugates that specifically target prostate tumor cells", Cancer Research, vol. 66, No. 12, Jun. 15, 2006, pp. 5989-5992.

Chua et al., "Pancreatic cancer—is the wall crumbling?", Annals of Oncology, vol. 19, No. 7, 2008, pp. 1224-1230.

Colella et al., "Increased cell density decreases cysteine proteinase inhibitor activity and increases invasive ability of two prostate tumor cell lines", Cancer Letters, vol. 185, No. 2, Nov. 28, 2002, pp. 163-172.

Crunkhorn, "RNA interference: clinical gene-silencing success", Nature Reviews Drug Discovery, vol. 9, May 2010, p. 359.

Cruz-Monserrate et al., "Detection of pancreatic cancer tumours and precursor lesions by cathepsin E activity in mouse models", Gut, vol. 61, No. 9, Sep. 2012, pp. 1315-1322.

Daniel et al., "Gold Nanoparticles: Assembly, Supramolecular Chemistry, Quantum-Size-Related Properties, and Applications toward Biology, Catalysis, and Nanotechnology", Chemical Reviews, vol. 104, No. 1, 2004, pp. 293-346.

Dassie et al., "Systemic administration of optimized aptamer-siRNA chimeras promotes regression of PSMA-expressing tumors", Nature Biotechnology, vol. 27, No. 9, 2009, pp. 839-849.

Davis et al., "Evidence of RNAi in humans from systemically administered siRNA via targeted nanoparticles", Nature, vol. 464, No. 7291, Apr. 15, 2010, pp. 1067-1070.

Declerck et al., "Proteases, extracellular matrix, and cancer: a workshop of the path B study section", American Journal of Pathology, vol. 164, No. 4, Apr. 2004, pp. 1131-1139.

Dhar et al., "Targeted delivery of cisplatin to prostate cancer cells by aptamer functionalized Pt(IV) prodrug-PLGA-PEG nanoparticles", Proceedings of the National Academy of Sciences of the USA, vol. 105, No. 45, Nov. 11, 2008, pp. 17356-17361.

Dolmans DE et al., "Photodynamic therapy for cancer," Nat Rev Cancer, 2003, vol. 3, pp. 380-387.

Dreyer et al., "Processing of the Pre-β-amyloid Protein by Cathepsin D is Enhanced by a Familial Alzheimer's Disease Mutation", European Journal of Biochemistry, vol. 224, No. 2, Sep. 1994, pp. 265-271.

Dunn, "A taste test for proteases", Nature Biotechnology, vol. 18, No. 2, Feb. 2000, pp. 149-150.

Edwards et al., "Cancer. Proteases—invasion and more", Nature, vol. 394, No. 6693, Aug. 6, 1998, pp. 527-528.

Elbakry et al., "Layer-by-Layer Assembled Gold Nanoparticles for siRNA Delivery", Nano Letters, vol. 9, No. 5, Mar. 30, 2009, pp. 2059-2064.

Elbashir et al., "Duplexes of 21-nucleotide RNAs mediate RNA interference in cultured mammalian cells", Nature, vol. 411, May 24, 2001, pp. 494-499.

Elouahabi et al., "Formation and Intracellular Trafficking of Lipoplexes and Polyplexes", Molecular Therapy, vol. 11, No. 3, Mar. 2005, pp. 336-347.

Eser et al., "In vivo diagnosis of murine pancreatic intraepithelial neoplasia and early-stage pancreatic cancer by molecular imaging", Proceedings of the National Academy of Science of the USA, vol. 108, No. 24, Jun. 14, 2011, pp. 9945-9950.

Evans et al. "Chemical imaging of tissue in vivo with video-rate coherent anti-Stokes Raman scattering microscopy," Proc. Natl. Acad. Sci.USA, 2005, vol. 102, No. 46, pp. 16807-16812.

Fan BG et al., "Photodynamic therapy for pancreatic cancer," Pancreas, 2007, vol. 34, pp. 385-389.

Farokhzad et al., "Nanoparticle-aptamer bioconjugates: a new approach for targeting prostate cancer cells", Cancer Research, vol. 64, No. 21, Nov. 1, 2004, pp. 7668-7672.

Fendrich et al., "Detection of Precursor Lesions of Pancreatic Adenocarcinoma in PET-CT in a Genetically Engineered Mouse Model of Pancreatic Cancer", Neoplasia, vol. 13, No. 2, Feb. 2011, pp. 180-186.

Fernandez et al., "Expression of cathepsins B and S in the progression of prostate carcinoma", International Journal of Cancer, vol. 95, No. 1, Jan. 20, 2001, pp. 51-55.

Finzi et al., "Cathepsin E in follicle associated epithelium of intestine and tonsils: localization to M cells and possible role in antigen processing", Histochemistry, vol. 99, No. 3, Mar. 1993, pp. 201-211.

Fire et al., "Potent and specific genetic interference by double-stranded RNA in *Caenorhabditis elegans*", Nature, vol. 391, No. 6669, Feb. 19, 1998, pp. 806-811.

Flores et al., "Detection of pancreatic carcinomas by imaging lactose-binding protein expression in peritumoral pancreas using [18F]fluoroethyl-deoxylactose PET/CT", PLoS One, vol. 4, No. 11, 2009, p. e7977.

Foltmann et al., In Handbook of Proteolytic Enzymes (Barrett, A.J., Rawlings, N.D. and Woessner, J.F., eds.), Academic Press, San Diego, 1998, pp. 819-823.

Frosch, "Molecular regulation, membrane association and secretion of tumor cathepsin B", APMIS, vol. 107, No. 1-6, Mar. 1999, pp. 28-37.

Fujimoto et al., "Layer-by-layer assembly of small interfering RNA and poly(ethyleneimine) for substrate-mediated electroporation with high efficiency", Analytical & Bioanalytical Chemistry, vol. 397, No. 2, May 2010, pp. 571-578.

Funovics et al., "Protease sensors for bioimaging", Analytical & Bioanalytical Chemistry, vol. 377, No. 6, Nov. 2003, pp. 956-963.

Gaind et al., "Deep-tissue imaging of intramolecular fluorescence resonance energy-transfer parameters," Opt. Letters, 2010, vol. 35, No. 9, pp. 1314-1316.

Gao et al., "Nonviral methods for siRNA delivery", Molecular Pharmaceutics, vol. 6, No. 3, May/Jun. 2009, pp. 651-658.

Gary et al., "Polymer-based siRNA delivery: perspectives on the fundamental and phenomenological distinctions from polymer-based DNA delivery", Journal of Controlled Release, vol. 121, No. 1-2, Aug. 16, 2007, pp. 64-73.

Ghosh et al., "Tumor target prostate specific membrane antigen (PSMA) and its regulation in prostate cancer", Journal of Cellular Biochemistry, vol. 91, No. 3, Feb. 15, 2004, pp. 528-539.

Giljohann, "Gene regulation with polyvalent siRNA-nanoparticle conjugates", Journal of the American Chemical Society, vol. 131, No. 6, Feb. 18, 2009, pp. 2072-2073.

(56) References Cited

OTHER PUBLICATIONS

Giljohann et al., "Gold Nanoparticles for Biology and Medicine", Angewandte Chemie International Edition, vol. 49, No. 19, Apr. 26, 2010, pp. 3280-3294.
Glondu, "A mutated cathepsin-D devoid of its catalytic activity stimulates the growth of cancer cells", Oncogene, vol. 20, No. 47, Oct. 18, 2001, pp. 6920-6929.
Goggins, "Identifying molecular markers for the early detection of pancreatic neoplasia", Seminars in Oncology, vol. 34, No. 4, Aug. 2007, pp. 303-310.
Goggins, "Markers of pancreatic cancer: working toward early detection", Clinical Cancer Research, vol. 17, No. 4, Feb. 15, 2011, pp. 635-637.
Gold et al., "Diversity of oligonucleotide functions", Annual Review of Biochemistry, vol. 64, 1995, pp. 763-797.
Gong et al., "Prostate-specific membrane antigen (PSMA)-specific monoclonal antibodies in the treatment of prostate and other cancers", Cancer Metastasis Reviews, vol. 18, No. 4, 1999, pp. 483-490.
Gounaris et al., "Live imaging of cysteine-cathepsin activity reveals dynamics of focal inflammation, angiogenesis, and polyp growth", PloS One, vol. 3, No. 8, Aug. 13, 2008, p. e2916.
Gulnik el al., "Design of sensitive fluorogenic substrates for human cathepsin D", Federation of European Biochemical Societies Letters, vol. 413, No. 2, Aug. 18, 1997, pp. 379-384.
Gutt et al., "Adjuvant radiotherapy for resected pancreatic cancer: a lack of benefit or a lack of adequate trials?", Nature Clinical Practice Gastroenterology and Hepatology, vol. 6, No. 1, Jan. 2009, pp. 38-46.
Haffner et al., "Prostate-specific membrane antigen expression in the neovasculature of gastric and colorectal cancers", Human Pathology, vol. 40, No. 12, Dec. 2009, pp. 1754-1761.
Hahn SM et al., "Photofrin uptake in the tumor and normal tissues of patients receiving intraperitoneal photodynamic therapy," Clin Cancer Res, 2006, vol. 12, pp. 5464-5470.
Harsha et al., "A compendium of potential biomarkers of pancreatic cancer", PLoS Medicine, vol. 6, No. 4, Apr. 7, 2009, p. e1000046.
Hawes et al., "A multispecialty approach to the diagnosis and management of pancreatic cancer", American Journal of Gastroenterology, vol. 95, No. 1, Jan. 2000, pp. 17-31.
Henry et al., "A prostate-specific membrane antigen-targeted monoclonal antibody-chemotherapeutic conjugate designed for the treatment of prostate cancer", Cancer Research, vol. 64, No. 21, Nov. 1, 2004, pp. 7995-8001.
Higashi et al., "Layer-by-layer fabrication of well-packed gold nanoparticle assemblies guided by a β-sheet peptide network", Polymer Journal, vol. 42, 2010, pp. 95-99.
Hingorani et al., "Preinvasive and invasive ductal pancreatic cancer and its early detection in the mouse", Cancer Cell, vol. 4, No. 6, Dec. 2003, pp. 437-450.
Ho et al., "Development of a dual fluorogenic and chromogenic dipeptidyl peptidase IV substrate", Bioorganic & Medicinal Chemistry Letters, vol. 16, No. 10, May 15, 2006, pp. 2599-2602.
Hon et al., "The roles of binding site arrangement and combinatorial targeting in microRNA repression of gene expression", Genome Biology, vol. 8, No. 8, 2007, p. R166.
Hopper C., "Photodynamic therapy: a clinical reality in the treatment of cancer," Lancet Oncol, 2000, vol. 1, pp. 212-219.
Hu et al., "Low Molecular Weight Polyethylenimine Conjugated Gold Nanoparticles as Efficient Gene Vectors", Bioconjugate Chemistry, vol. 21, No. 5, 2010, pp. 836-843.
Huguet et al., "Chemoradiotherapy in the management of locally advanced pancreatic carcinoma: a qualitative systematic review", Journal of Clinical Oncology, vol. 27, No. 13, May 1, 2009, pp. 2269-2277.
Hutvagner et al., "Argonaute proteins: key players in RNA silencing", Nature Review Molecular Cell Biology, vol. 9, No. 1, Jan. 2008, pp. 22-32.
Issa MC et al., "Photodynamic therapy: a review of the literature and image documentation," An Bras Dermatol, 2010, vol. 85, pp. 501-511.

Izuishi et al., "Impact of 18-fluorodeoxyglucose positron emission tomography on the management of pancreatic cancer", Journal of Gastrointestinal Surgery, vol. 14, No. 7, Jul. 2010, pp. 1151-1158.
Jackson et al., "Analysis of lung tumor initiation and progression using conditional expression of oncogenic K-ras", Genes and Development, vol. 15, No. 24, Dec. 15, 2001, pp. 3243-3248.
Jaffer et al., "In vivo imaging of thrombin activity in experimental thrombi with thrombin-sensitive near-infrared molecular probe", Arteriosclerosis, Thrombosis, and Vascular Biology, vol. 22, No. 11, Nov. 1, 2002, pp. 1929-1935.
Jang B et al., "Gold nanorod-photosensitizer complex for near-infrared fluorescence imaging and photodynamic/photothermal therapy in vivo," ACS Nano, 2011, vol. 5, pp. 1086-1094.
Jemal et al., "Cancer statistics, 2008", CA: A Cancer Journal for Clinicians, vol. 58, No. 2, 2008, pp. 71-96.
Jemal et al., "Cancer statistics, 2010", CA: A Cancer Journal for Clinicians, vol. 60, No. 5, Sep./Oct. 2010, pp. 277-300.
Jewell et al., "Multilayered polyelectrolyte assemblies as platforms for the delivery of DNA and other nucleic acid-based therapeutics", Advanced Drug Delivery Reviews, vol. 60, No. 9, 2008, pp. 979-999.
Ji et al., "Ras activity levels control the development of pancreatic diseases", Gastroenterology, vol. 137, No. 3, Sep. 2009, pp. 1072-1082.
Jinek et al., "A three-dimensional view of the molecular machinery of RNA interference", Nature, vol. 457, No. 7228, Jan. 22, 2009, pp. 405-412.
John et al., "Human MicroRNA targets", PLoS Biology, vol. 2, No. 11, Nov. 2004, p. e363.
Jonkers et al., "Synergistic tumor suppressor activity of BRCA2 and p53 in a conditional mouse model for breast cancer", Nature Genetics, vol. 29, No. 4, Dec. 2001, pp. 418-425.
Josephson et al., "High-efficiency intracellular magnetic labeling with novel superparamagnetic-Tat peptide conjugates", Bioconjugate Chemistry, vol. 10, No. 2, Mar./Apr. 1999, pp. 186-191.
Juliano et al., "Biological barriers to therapy with antisense and siRNA oligonucleotides", Molecular Pharmaceutics, vol. 6, No. 3, May/Jun. 2009, pp. 686-695.
Jupp et al., "Identification of the aspartic proteinases from human erythrocyte membranes and gastric mucosa (slow-moving proteinase) as catalytically equivalent to cathepsin E", Biochemical Journal, vol. 254, No. 3, Sep. 15, 1988, pp. 895-898.
Jupp et al., "The selectivity of statine-based inhibitors against various human aspartic proteinases", Biochemical Journal, vol. 265, No. 3, Feb. 1, 1990, pp. 871-878.
Just et al. "Optical coherence tomography allows for the reliable identification of laryngeal epithelial dysplasia and for precise biopsy: a clinicopathological study of 61 patients undergoing microlaryngoscopy" Laryngoscope, 2010, vol. 120, No. 10, pp. 1964-1970.
Kageyama et al., "A Cathepsin D-Like Acid Proteinase from Human Gastric Mucosa: Purification and Characterization", The Journal of Biochemistry, vol. 87, No. 3, Mar. 1989, pp. 737-743.
Kageyama, "Procathepsin E and cathepsin E", Methods in Enzymology, vol. 248, 1995, pp. 120-136.
Kageyama, "Rabbit procathepsin E and cathepsin E : Nucleotide sequence of cDNA, hydrolytic specificity for biologically active peptides and gene expression during development", European Journal of Biochemistry, vol. 216, No. 3, Sep. 1993, pp. 717-728.
Kakehashi et al., "Differential Regulation of the Nature and Functions of Dendritic Cells and Macrophages by Cathepsin E", The Journal of Immunology, vol. 179, No. 9, Nov. 1, 2007, pp. 5728-5737.
Kaul et al., "HIV protease inhibitors: advances in therapy and adverse reactions, induding metabolic complications", Pharmacotherapy, vol. 19, No. 3, Mar. 1999, pp. 281-298.
Ke et al., "Optimal subsite occupancy and design of a selective inhibitor of urokinase", Journal of Biological Chemistry, vol. 272, No. 33, 1997, pp. 20456-20462.
Kelly et al., "Targeted nanoparticles for imaging incipient pancreatic ductal adenocarcinoma", PLoS Medicine, vol. 5, No. 4, 2008, p. e85.
Kennedy JC et al., "Photodynamic therapy with endogenous protoporphyrin IX: basic principles and present clinical experience," J Photochem Photobiol B, 1990, vol. 6, pp. 143-148.

(56) References Cited

OTHER PUBLICATIONS

Khan et al., "Cathepsin B and tumor-associated laminin expression in the progression of colorectal adenoma to carcinoma.", Modern Pathology, vol. 11, No. 8, Aug. 1998, pp. 704-708.
Kichler, "Gene transfer with modified polyethylenimines", Journal of Gene Medicine, vol. 6, Suppl. 1, Feb. 2004, pp. S3-S10.
Kim et al., "Generation of orthotopic and heterotopic human pancreatic cancer xenografts in immunodeficient mice", Nature Protocols, vol. 4, No. 11, 2009, pp. 1670-1680.
Kim et al., "Strategies for silencing human disease using RNA interference", Nature Reviews Genetics, vol. 8, No. 3, Mar. 2007, pp. 173-184.
Kim et al., "Strategies for targeted nonviral delivery of siRNAs in vivo", Trends in Molecular Medicine, vol. 15, No., Nov. 2009, pp. 491-500.
Kisiday et al., "Self-assembling peptide hydrogel fosters chondrocyte extracellular matrix production and cell division: implications for cartilage tissue repair", Proceedings of the National Academy of Sciences of the USA, vol. 99, No. 15, Jul. 23, 2002, pp. 9996-10001.
Kitamura, "Development of Systemic in vitro Evolution and Its Application to Generation of Peptide-Aptamer-Based Inhibitors of Cathepsin E", Journal of Molecular Biology, vol. 387, No. 5, Apr. 17, 2009, pp. 1186-1198.
Koblinski et al., "Unraveling the role of proteases in cancer", Clinical Chimica Acta, vol. 291, No. 2, Feb. 15, 2000, pp. 113-135.
Konan YN et al., "State of the art in the delivery of photosensitizers for photodynamic therapy," J Photochem Photobiol B, 2002, vol. 66, pp. 89-106.
Krek et al., "Combinatorial microRNA target predictions", Nature Genetics, vol. 37, No. 5, May 2005, pp. 495-500.
Krishna et al., "EUS/EUS-FNA for suspected pancreatic cancer: influence of chronic pancreatitis and clinical presentation with or without obstructive jaundice on performance characteristics", Gastrointestinal Endoscopy, vol. 70, No. 1, Jul. 2009, pp. 70-79.
Kumar et al., "T Cell-Specific siRNA Delivery Suppresses HIV-1 Infection in Humanized Mice", Cell, vol. 134, No. 4, Aug. 22, 2008, pp. 577-586.
Kunath et al., "Low-molecular-weight polyethylenimine as a non-viral vector for DNA delivery: comparison of physicochemical properties, transfection efficiency and in vivo distribution with high-molecular-weight polyethylenimine", Journal of Controlled Release, vol. 89, No. 1, Apr. 14, 2003, pp. 113-125.
Kwan et al., "Grassystatins A-C from Marine Cyanobacteria, Potent Cathepsin E Inhibitors That Reduce Antigen Presentation", Journal of Medicinal Chemistry, vol. 52, No. 18, Sep. 24, 2009, pp. 5732-5747.
Kyte et al., "A simple method for displaying the hydropathic character of a protein", Journal of Molecular Biology, vol. 157, No. 1, May 5, 1982, pp. 105-132.
Ladror et al., "Cleavage at the amino and carboxyl termini of Alzheimer's amyloid-beta by cathepsin D", Journal of Biological Chemistry, vol. 269, No. 28, Jul. 15, 1994, pp. 18422-18428.
Lai et al., "Early diagnosis of osteoarthritis using cathepsin B sensitive near-infrared fluorescent probes", Osteoarthritis and Cartilage, vol. 12, No. 3, Mar. 2004, pp. 239-244.
Law et al., "A mitochondrial targeted fusion peptide exhibits remarkable cytotoxicity", Molecular Cancer Therapeutics, vol. 5, No. 8, Aug. 2006, pp. 1944-1949.
Law et al., "Design, Synthesis, and Characterization of Urokinase Plasminogen-Activator-Sensitive Near-Infrared Reporter", Chemistry & Biology, vol. 11, No. 1, Jan. 2004, pp. 99-106.
Law et al., "Optical zymography for specific detection of urokinase plasminogen activator activity in biological samples", Analytical Biochemistry, vol. 338, No. 1, Mar. 1, 2005, pp. 151-158.
Law et al., "Peptide-based biomaterials for protease-enhanced drug delivery", Biomacromolecules, vol. 7, No. 4, 2006, pp. 1261-1265.
Law et al., "Proteolysis: a biological process adapted in drug delivery, therapy, and imaging", Bioconjugate Chemistry, vol. 20, No. 9, Sep. 2009, pp. 1683-1695.

Ledakis et al., "Cathepsins D, B, and L in malignant human lung tissue", Clinical Cancer Research, vol. 2, No. 3, Mar. 1996, pp. 561-568.
Lee et al., "All-in-one target-cell-specific magnetic nanoparticles for simultaneous molecular imaging and siRNA delivery", Angewandte Chemie International Edition, vol. 48, No. 23, 2009, pp. 4174-4179.
Lee et al., "Layered nanoprobe for long-lasting fluorescent cell label", Small, vol. 8, No. 21, Nov. 5, 2012, pp. 3315-3320.
Lee, S.K. et al., "Effective Gene Silencing by multilayered siRNA coated gold nanoparticles," Small, 2011, vol. 7, No. 3, pp. 364-370.
Leguen et al., "Bioactive coatings based on polyelectrolyte multilayer architectures functionalized by embedded proteins, peptides or drugs", Biomolecular Engineering, vol. 24, No. 1, Feb. 2007, pp. 33-41.
Lewin et al., "Tat peptide-derivatized magnetic nanoparticles allow in vivo tracking and recovery of progenitor cells", Nature Biotechnology, vol. 18, No. 4, Apr. 2000, pp. 410-414.
Lewis et al., "The absence of p53 promotes metastasis in a novel somatic mouse model for hepatocellular carcinoma", Molecular and Cellular Biology, vol. 25, No. 4, Feb. 2005, pp. 1228-1237.
Lin et al., "Novel near-infrared cyanine fluorochromes: synthesis, properties, and bioconjugation", Bioconjugate Chemistry, vol. 13, No. 3, May/Jun. 2002, pp. 605-610.
Liu CD et al., "Hypericin and photodynamic therapy decreases human pancreatic cancer in vitro and in vivo," J Surg Res, 2000, vol. 93, pp. 137-143.
Liu et al., "Peptide-based molecular beacons for cancer imaging and therapy", Amino Acids, vol. 41, No. 5, Nov. 2011, pp. 1123-1134.
Loos et al., "Surgical treatment of pancreatic cancer", Annals of the NY Academy of Sciences, vol. 1138, Sep. 2008, pp. 169-180.
Lovell JF et al., "Activatable photosensitizers for imaging and therapy," Chem Rev, 2010, vol. 110, pp. 2839-2857.
Lu et al., "Covalently linked DNA/protein multilayered film for controlled DNA release", Journal of Colloid and Interface Science, vol. 314, No. 1, Oct. 1, 2007, pp. 80-88.
Lupold et al., "Identification and characterization of nuclease-stabilized RNA molecules that bind human prostate cancer cells via the prostate-specific membrane antigen", Cancer Research, vol. 62, No. 14, Jul. 15, 2002, pp. 4029-4033.
Mackay et al., "A Possible Role for Cathepsins D, E, and B in the Processing of β-amyloid Precursor Protein in Alzheimer's Disease", European Journal of Biochemistry, vol. 244, No. 2, Mar. 1997, pp. 414-425.
Mallikaratchy et al., "Cell specific aptamer-photosensitizer conjugates as a molecular tool in photodynamic therapy", ChemMedChem, vol. 3, No. 3, Mar. 2008, pp. 425-428.
Mansouri, "Modulating the release kinetics through the control of the permeability of the layer-by-layer assembly: a review", Expert Opinion on Drug Delivery, vol. 6, No. 6, Jun. 2009, pp. 585-597.
Marecos et al., "Antibody-mediated versus nontargeted delivery in a human small cell lung carcinoma model", Bioconjugate Chemistry, vol. 9, No. 2, Mar./Apr. 1998, pp. 184-191.
Marten et al., "Detection of dysplastic intestinal adenomas using enzyme-sensing molecular beacons in mice", Gastroenterology, vol. 122, No. 2, Feb. 2002, pp. 406-414.
Matsuo et al., "Immunohistochemical localization of cathepsins D and E in human gastric cancer: A possible correlation with local invasive and metastatic activities of carcinoma cells", Human Pathology, vol. 27, No. 2, Feb. 1996, pp. 184-190.
Mayya et al., "Preparation and Organization of Nanoscale Polyelectrolyte-Coated Gold Nanoparticles", Advanced Functional Materials, vol. 13, No. 3, Mar. 2003, pp. 183-188.
McCawley et al., "Matrix metalloproteinases: multifunctional contributors to tumor progression", Molecular Medicine Today, vol. 6, No. 4, Apr. 1, 2000, pp. 149-156.
McIntyre et al., "Molecular imaging of proteolytic activity in cancer", Journal of Cellular Biology, vol. 90, No. 6, Dec. 15, 2003, pp. 1087-1097.
McNamara et al., "Cell type-specific delivery of siRNAs with aptamer-siRNA chimeras", Nature Biotechnology, vol. 24, No. 8, 2006, pp. 1005-1015.
Medarova et al., "In vivo imaging of siRNA delivery and silencing in tumors", Nature Medicine, vol. 13, No. 3, Mar. 2007, pp. 372-377.

(56) References Cited

OTHER PUBLICATIONS

Meister et al., "Mechanisms of gene silencing by double-stranded RNA", Nature, vol. 431, No. 7006, Sep. 16, 2004, pp. 343-349.
Messerli et al., "A novel method for imaging apoptosis using a caspase-1 near-infrared fluorescent probe", Neoplasia, vol. 6, No. 2, Mar./Apr. 2004, pp. 95-105.
Mitelman et al., "The impact of translocations and gene fusions on cancer causation", Nature Reviews Cancer, vol. 7, No. 4, Apr. 2007, pp. 233-245.
Mota et al., "Cathepsin E expression by normal and premalignant cervical epithelium", American Journal of Pathology, vol. 150, No. 4, Apr. 1997, pp. 1223-1229.
Murphy et al., "Current evaluation of the tissue localization and diagnostic utility of prostate specific membrane antigen", Cancer, vol. 83. No. 11, Dec. 1, 1998, pp. 2259-2269.
Musiol R et al., "Prodrugs in photodynamic anticancer therapy," Curr Pharm Des, 2011, vol. 17, pp. 3548-3559.
Muto et al., "Characteristic Distribution of Cathepsin E Which Immunologically Cross-Reacts with the 86-kDa Acid Proteinase from Rat Gastric Mucosa", The Journal of Biochemistry, vol. 103, No. 4, Apr. 1988, pp. 629-632.
Muto et al., "Purification and properties of a cathepsin D-like acid proteinase from rat gastric mucosa", Biochimica et Biophysica Acta (BBA)—Protein Structure and Molecular Enzymology, vol. 745, No. 1, May 30, 1983, pp. 61-69.
Nakanishi et al., "Increased Expression of Cathepsins E and D in Neurons of the Aged Rat Brain and Their Colocalization with Lipofuscin and Carboxy-Terminal Fragments of Alzheimer Amyloid Precursor Protein", Journal of Neurochemistry, vol. 68, No. 2, Feb. 1997, pp. 739-749.
Nishikawa et al., "The role of cathepsin B and cystatin C in the mechanisms of invasion by ovarian cancer", Gynecologic Oncology, vol. 92, No. 3, Mar. 2004, pp. 881-886.
Nishioka NS, "Drug, light, and oxygen: a dynamic combination in the clinic," Gastroenterology, 1998, vol. 114, pp. 604-606.
Nomura et al., "Involvement of cathepsins in the invasion, metastasis and proliferation of cancer cells", Journal of Medical Investigation, vol. 52, No. 1-2, Feb. 2005, pp. 1-9.
Olive et al., "The use of targeted mouse models for preclinical testing of novel cancer therapeutics", Clinical Cancer Research, vol. 12, No. 18, Sep. 15, 2006, pp. 5277-5287.
Parsons et al., "Preoperative evaluation of pancreatic adenocarcinoma", Journal of Hepatobiliary Pancreatic Surgery, vol. 15, No. 4, 2008, pp. 429-435.
Peiper et al., "Human Pancreatic Cancer Cells (MPANC-96) Recognized by Autologous Tumor-Infiltrating Lymphocytes After in Vitro as Well as in Vivo Tumor Expansion", International Journal of Cancer, vol. 71, No. 6, Jun. 11, 1997, pp. 993-999.
Peng Q et al., "5-Aminolevulinic acid-based photodynamic therapy. Clinical research and future challenges," Cancer, 1997, vol. 79, pp. 2282-2308.
Peterson CM et al., "HPMA copolymer delivery of chemotherapy and photodynamic therapy in ovarian cancer," Adv Exp Med Biol, 2003, vol. 519, pp. 101-123.
Peyratout et al., "Tailor-Made Polyelectrolyte Microcapsules: From Multilayers to Smart Containers", Angewandte Chemie International Edition, vol. 43, No. 29, Jul. 19, 2004, pp. 3762-3783.
Pham et al., "Developing a peptide-based near-infrared molecular probe for protease sensing", Bioconjugate Chemistry, vol. 15, No. 6, Nov./Dec. 2004, pp. 1403-1407.
Podgorski, "Bone microenvironment modulates expression and activity of cathepsin B in prostate cancer", Neoplasia, vol. 7, No. 3, Mar. 2005, pp. 207-223.
Prasad et al., "Gene expression profiles in pancreatic intraepithelial neoplasia reflect the effects of Hedgehog signaling on pancreatic ductal epithelial cells", Cancer Research, vol. 65, No. 5, Mar. 1, 2005, pp. 1619-1626.

Qin et al., "Inhibiting HIV-1 infection in human T cells by lentiviral-mediated delivery of small interfering RNA against CCR5", Proceedings of the National Academy of Sciences of the USA, vol. 100, No. 1, Jan. 7, 2003, pp. 183-188.
Qiu et al., "Environment-sensitive hydrogels for drug delivery", Advances in Drug Delivery Reviews, vol. 53, No. 3, Dec. 31, 2001, pp. 321-339.
Rabbitts, "Commonality but diversity in cancer gene fusions", Cell, vol. 137, No. 3, May 1, 2009, pp. 391-395.
Rao et al., "Specificity in the binding of inhibitors to the active site of human/primate aspartic proteinases: analysis of P2-P1-P1'-P2' variation", Journal of Medicinal Chemistry, vol. 36, No. 18, 1993, pp. 2614-2620.
Rao-Naik et al., "Exploring the binding preferences/specificity in the active site of human cathepsin E", Proteins, vol. 22, No. 2, Jun. 1995, pp. 168-181.
Read et al., "A versatile reducible polycation-based system for efficient delivery of a broad range of nucleic acids", Nucleic Acids Research, vol. 33, No. 9, May 2005, p. e86.
Regula J et al., "Photodynamic therapy using 5-aminolaevulinic acid for experimental pancreatic cancer—prolonged animal survival," Br J Cancer, 1994, vol. 70, pp. 248-254.
Reynolds et al., "Protamine as an efficient membrane-translocating peptide", Bioconjugate Chemistry, vol. 16, No. 5, 2005, pp. 1240-1245.
Rocha-Lima, "New directions in the management of advanced pancreatic cancer: a review", Anticancer Drugs, vol. 19, No. 5, Jun. 2008, pp. 435-446.
Rochefort et al., "Cathepsin D in cancer metastasis: A protease and a ligand", Apmis, vol. 107, No. 1-6, Mar. 1999, pp. 86-95.
Rosi et al., "Oligonucleotide-modified gold nanoparticles for intracellular gene regulation", Science, vol. 312, No. 5776, May 19, 2006, pp. 1027-1030.
Rubin et al., "Bioinformatics approach leads to the discovery of the TMPRSS2:ETS gene fusion in prostate cancer", Laboratory Investigations, vol. 86, No. 11, Nov. 2006, pp. 1099-1102.
Sakai et al., "Quantitation and immunohistochemical localization of cathepsins E and D in rat tissues and blood cells", Biochimica et Biophysica Acta (BBA)—General Subjects, vol. 991, No. 2, May 31, 1989, pp. 367-375.
Sastradipura et al., "Identification of Cellular Compartments Involved in Processing of Cathepsin E in Primary Cultures of Rat Microglia", The Journal of Neurochemistry, vol. 70, No. 5, May 1998, pp. 2045-2056.
Scarborough et al., "Exploration of subsite binding specificity of human cathepsin D through kinetics and rule-based molecular modeling", Protein Science, vol. 2, No. 2, Feb. 1993, pp. 264-276.
Scarborough et al., "Redesign of the substrate specificity of human cathepsin D: the dominant role of position 287 in the S2 subsite", Protein Engineering Design & Selection, vol. 7, No. 4, Apr. 1994, pp. 495-502.
Schneider et al., "Multifunctional Cytotoxic Stealth Nanoparticles. A Model Approach with Potential for Cancer Therapy", Nano Letters, vol. 9, No. 2, Feb. 2009, pp. 636-642.
Schultz et al., "Mobile Near-Infrared Fluorescence Imaging: New Tissue Resection Guidance Tool for Surgeons", www.siemens.com/medical-magazine, Dec. 2007, 8 pages.
Scorilas et al., "Determination of cathepsin B expression may offer additional prognostic information for ovarian cancer patients", Biological Chemistry, vol. 383, No. 7-8, Jul./Aug. 2002, pp. 1297-1303.
Sessa et al., "Ductal cancers of the pancreas frequently express markers of gastrointestinal epithelial cells", Gastroenterology, vol. 98, No. 6, Jun. 1990, pp. 1655-1665.
Shah et al., "In Vivo Imaging of HIV Protease Activity in Amplicon Vector-transduced Gliomas", Cancer Research, vol. 64, No. 1, Jan. 1, 2004, pp. 273-278.
Shah et al., "Inducible release of TRAIL fusion proteins from a proapoptotic form for tumor therapy", Cancer Research, vol. 64, No. 9, May 1, 2004, pp. 3236-3242.
Siegel R et al., "Cancer statistics, 2012," CA Cancer J Clin, 2012, vol. 62, pp. 10-29.

(56) References Cited

OTHER PUBLICATIONS

Singh et al., "Poly-l-lysine-coated albumin nanoparticles: Stability, mechanism for increasing in vitro enzymatic resilience, and siRNA release characteristics", Acta Biomaterialia, vol. 6, No. 11, Nov. 2010, pp. 4277-4284.
Sinha et al., "Cathepsin B in angiogenesis of human prostate: an immunohistochemical and immunoelectron microscopic analysis", The Anatomical Record, vol. 241, No. 3, Mar. 1995, pp. 353-362.
Sinha et al., "Immunohistochemical localization of cathepsin B in neoplastic human prostate", Prostate, vol. 26, No. 4, Apr. 1995, pp. 171-178.
Sinha et al., "Plasma membrane association of cathepsin B in human prostate cancer: biochemical and immunogold electron microscopic analysis", Prostate, vol. 49, No. 3, Nov. 1, 2001, pp. 172-184.
Smith et al., "Synthetic peptide-based DNA complexes for nonviral gene delivery", Advanced Drug Delivery Reviews, vol. 30, No. 1-3, 1998, pp. 115-131.
Song et al., "Gold nanoparticles capped with polyethyleneimine for enhanced siRNA delivery", Small, vol. 6, No. 2, Jan. 2010, pp. 239-246.
Sun et al., "Novel targets for therapeutic intervention against ischemic brain injury", Clinical Neuropharmacology, vol. 22, No. 3, May/Jun. 1999, pp. 164-171.
Tai et al., "Inhibition of Breast Cancer Cell Growth and Invasiveness by Dual Silencing of HER-2 and VEGF", Molecular Pharmaceutics, vol. 7, No. 2, Apr. 5, 2010, pp. 543-556.
Tang, In Handbook of Proteolytic Enzymes (Barrett, A.J., Rawlings, N.D. and Woessner, J.F., eds.), Academic Press, San Diego, 1998, pp. 828-836.
Tatematsu et al., "Markers of surface mucous cell type human gastric cancer cells: galactose oxidase-Schiff reactive mucins, monoclonal antibody SH-9 reactive mucins and cathepsin E", Acta Pathologica Japonica, vol. 43, No. 9, Sep. 1993, pp. 500-506.
Tenti et al., "Cervical adenocarcinomas express markers common to gastric, intestinal, and pancreatobiliary epithelial cells", Pathology, Research and Practice, vol. 190, No. 4, Apr. 1994, pp. 342-349.
Terris et al., "Characterization of Gene Expression Profiles in Intraductal Papillary-Mucinous Tumors of the Pancreas", American Journal of Pathology, vol. 160, No. 5, May 2002, pp. 1745-1754.
Thomas et al., "Conjugation to gold nanoparticles enhances polyethylenimine's transfer of plasmid DNA into mammalian cells", Proceedings of the National Academy of Sciences of the USA, vol. 100, No., Jun. 12, 2003, pp. 9138-9143.
Tiemann et al., "You have full text access to this OnlineOpen article RNAi-based therapeutics—current status, challenges and prospects", EMBO Molecular Medicine, vol. 1, No. 3, Jun. 2009, pp. 142-151.
Tomari et al., "Perspective: machines for RNAi", Genes & Development, vol. 19, No. 5, Mar. 1, 2005, pp. 517-529.
Tomlins et al., "Distinct classes of chromosomal rearrangements create oncogenic ETS gene fusions in prostate cancer", Nature, vol. 448, No. 7153, Aug. 2, 2007, pp. 595-599.
Tomlins et al., "Recurrent fusion of TMPRSS2 and ETS transcription factor genes in prostate cancer", Science, vol. 310, No. 5748, Oct. 28, 2005, pp. 644-648.
Topazian M et al., "Photodynamic therapy of intraductal papillary mucinous neoplasm," Endoscopy, 2012, vol. 44, pp. 213-215.
Torchilin et al., "TAT peptide on the surface of liposomes affords their efficient intracellular delivery even at low temperature and in the presence of metabolic inhibitors", Proceedings of the National Academy of Sciences of the USA, vol. 98, No. 15, Jul. 17, 2001, pp. 8786-8791.
Tsukuba, "Association of cathepsin E deficiency with development of atopic dermatitis", Journal of Biochemistry, vol. 134, No. 6, Dec. 2003, pp. 893-902.
Tung et al., "A Novel Near-Infrared Fluorescence Sensor for Detection of Thrombin Activation in Blood", Chembiochem, vol. 3, No. 2-3, Mar. 1, 2002, pp. 207-211.
Tung et al., "Arginine containing peptides as delivery vectors", Advanced Drug Delivery Reviews, vol. 55, No. 2, Feb. 10, 2003, pp. 281-294.
Tung et al., "In Vivo Imaging of Proteolytic Enzyme Activity Using a Novel Molecular Reporter", Cancer Research, vol. 60, No. 17, Sep. 1, 2000, pp. 4953-4958.
Tung et al., "Novel branching membrane translocational peptide as gene delivery vector", Bioorganic & Medicinal Chemistry, vol. 10, No. 11, Nov. 2002, pp. 3609-3614.
Tung et al., "Preparation of a Cathepsin D Sensitive Near-Infrared Fluorescence Probe for Imaging", Bioconjugate Chemistry, vol. 10, No. 5, Sep. 1999, pp. 892-896.
Ueno et al., "Adjuvant treatments for resectable pancreatic cancer", Journal of Hepatobiliary Pancreatic Surgery, vol. 15, No. 5, Sep. 2008, pp. 468-472.
Ullmann et al., "Protein expression profiles in adenocarcinomas and squamous cell carcinomas of the lung generated using tissue microarrays", Journal of Pathology, vol. 203, No. 3, Jul. 2004, pp. 798-807.
Uno et al., "Clinical significance of cathepsin E in pancreatic juice in the diagnosis of pancreatic ductal adenocarcinoma", Journal of Gastroenterology and Hepatology, vol. 15, No. 11, Nov. 2000, pp. 1333-1338.
Urban-Klein et al., "RNAi-mediated gene-targeting through systemic application of polyethylenimine (PEI)-complexed siRNA in vivo", Gene Therapy, vol. 12, No. 5, Mar. 2005, pp. 461-466.
Van Geel IP et al., "Mechanisms for optimising photodynamic therapy: second-generation photosensitisers in combination with mitomycin C," Br J Cancer, 1995, vol. 72, pp. 344-350.
Varadarajulu et al., "Yield of EUS-guided FNA of pancreatic masses in the presence or the absence of chronic pancreatitis", Gastrointestinal Endoscopy, vol. 62, No. 5, Nov. 2005, pp. 728-736.
Verma et al., "Effect of surface properties on nanoparticle-cell interactions", Small, vol. 6, No. 1, Jan. 4, 2010, pp. 12-21.
Von Burstin et al., "Highly sensitive detection of early-stage pancreatic cancer by multimodal near-infrared molecular imaging in living mice", International Journal of Cancer, vol. 123, No. 9, Nov. 1, 2008, pp. 2138-2147.
Waghray et al., "Analysis of a truncated form of cathepsin H in human prostate tumor cells", Journal of Biological Chemistry, vol. 277, No. 13, Mar. 29, 2002, pp. 11533-11538.
Waley et al., "The action of trypsin on polylysine", Biochemical Journal, vol. 55, No. 2, Sep. 1953, pp. 328-337.
Wang et al., "Design and synthesis of new fluorogenic HIV protease substrates based on resonance energy transfer", Tetrahedron Letters, vol. 31, No. 45, 1990, pp. 6493-6496.
Wang et al., "Pleiotropic biological activities of alternatively spliced TMPRSS2/ERG fusion gene transcripts", Cancer Research, vol. 68, No. 20, Oct. 15, 2008, pp. 8516-8524.
Wang et al., "Superparamagnetic iron oxide nanoparticle-aptamer bioconjugates for combined prostate cancer imaging and therapy", ChemMedChem, vol. 3, No. 9, Sep. 15, 2008, pp. 1311-1315.
Weissleder et al., "In vivo imaging of tumors with protease-activated near-infrared fluorescent probes", Nature Biotechnology, vol. 17, No. 4, Apr. 1999, pp. 375-378.
Weissleder et al., "Non-invasive in vivo mapping of tumour vascular and interstitial volume fractions", European Journal of Cancer, vol. 34, No. 9, Aug. 1998, pp. 1448-1454.
Wild et al., "Gene expression profiling of progressive papillary noninvasive carcinomas of the urinary bladder", Clinical Cancer Research, vol. 11, No. 12, Jun. 15, 2005, pp. 4415-4429.
Wullner et al., "Cell-specific induction of apoptosis by rationally designed bivalent aptamer-siRNA transcripts silencing eukaryotic elongation factor 2", Current Cancer Drug Targets, vol. 8, No. 7, Nov. 2008, pp. 554-565.
Wunder et al., "In vivo imaging of protease activity in arthritis: a novel approach for monitoring treatment response", Arthritis and Rheumatism, vol. 50, No. 8, Aug. 2004, pp. 2459-2465.
Xie Q et al., "Synergetic anticancer effect of combined gemcitabine and photodynamic therapy on pancreatic cancer in vivo," World J Gastroenterol, 2009, vol. 15, pp. 737-741.

(56) References Cited

OTHER PUBLICATIONS

Xiong et al., "Periodicity of polar and nonpolar amino acids is the major determinant of secondary structure in self-assembling oligomeric peptides", Proceedings of the National Academy for Sciences of the USA, vol. 92, No. 14, Jul. 3, 1995, pp. 6349-6353.
Yamamoto et al., "Affinity Purification and Properties of Cathepsin-E-Like Acid Proteinase from Rat Spleen", European Journal of Biochemistry, vol. 92, No. 2, Dec. 1978, pp. 499-508.
Yang et al., "Molecular imaging of pancreatic cancer in an animal model using targeted multifunctional nanoparticles", Gastroenterology, vol. 136, No. 5, May 2009, pp. 1514-1525e2.
Yasuda et al., "A new selective substrate for cathepsin E based on the cleavage site sequence of α2-macroglobulin", Biological Chemistry, vol. 386, No. 3, Mar. 2005, pp. 299-305.
Yasuda et al., "Characterization of New Fluorogenic Substrates for the Rapid and Sensitive Assay of Cathepsin E and Cathepsin D", Journal of Biochemistry, vol. 125, No. 6, Jun. 1999, pp. 1137-1143.
Yeo et al., "Six hundred fifty consecutive pancreaticoduodenectomies in the 1990s: pathology, complications, and outcomes", Annals of Surgery, vol. 226, No. 3, Sep. 1997, pp. 248-260.
Yoshimine et al., "Specific immunocytochemical localization of cathepsin E at the ruffled border membrane of active osteoclasts", Cell and Tissue Research, vol. 281, No. 1, Jul. 1995, pp. 85-91.
Yusuf TE et al., "EUS-guided photodynamic therapy with verteporfin for ablation of normal pancreatic tissue: a pilot study in a porcine model (with video)," Gastrointest Endosc, 2008, vol. 67, pp. 957-961.
Zaidi et al., "A new approach for distinguishing cathepsin E and D activity in antigen-processing organelles", Federation of European Biochemical Societies Journal, vol. 274, No. 12, Jun. 2007, pp. 3138-3149.
Zaidi et al., "Cathepsin E: a mini review", Biochemical and Biophysical Research Communications, vol. 367, No. 3, Mar. 14, 2008, pp. 517-522.
Zaidi et al., "Emerging Functional Roles of Cathepsin E", Biochemical and Biophysical Research Communications, vol. 377, No. 2, 2008, pp. 327-330.
Zaidi et al., "Recombinant cathepsin E has no proteolytic activity at neutral pH", Biochemical and Biophysical Research Communications, vol. 360, No. 1, Aug. 17, 2007, pp. 51-55.
Zamore, "RNA interference: big applause for silencing in Stockholm", Cell, vol. 127, No., Dec. 15, 2006, pp. 1083-1086.
Zhang et al., "Cationic lipids and polymers mediated vectors for delivery of siRNA", Journal of Controlled Release, vol. 123, No. 1, Oct. 18, 2007, pp. 1-10.
Zhang et al., "Construction of a novel chimera consisting of a chelator-containing Tat peptide conjugated to a morpholino antisense oligomer for technetium-99m labeling and accelerating cellular kinetics", Nuclear Medicine and Biology, vol. 33, No. 2, Feb. 2006, pp. 263-269.
Zhang et al., "SiRNA-loaded multi-shell nanoparticles incorporated into a multilayered film as a reservoir for gene silencing", Biomaterials, vol. 31, No. 23, Aug. 2010, pp. 6013-6018.
Zhang et al., "Using an RNA aptamer probe for flow cytometry detection of CD30-expressing lymphoma cells", Laboratory Investigation, vol. 89, No. 12, Dec. 2009, pp. 1423-1432.

\* cited by examiner

PanIN2
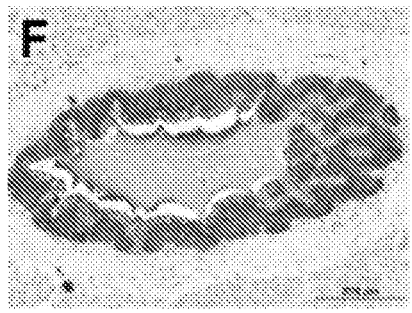 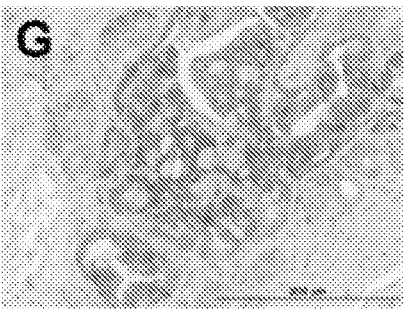
Figure 15F          Figure 15G
PanIN3
 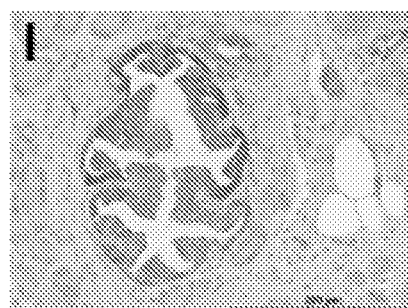
Figure 15H          Figure 15I
PDAC
 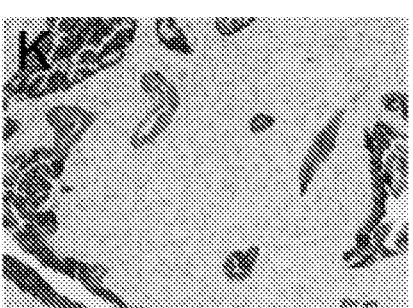
Figure 15J          Figure 15K

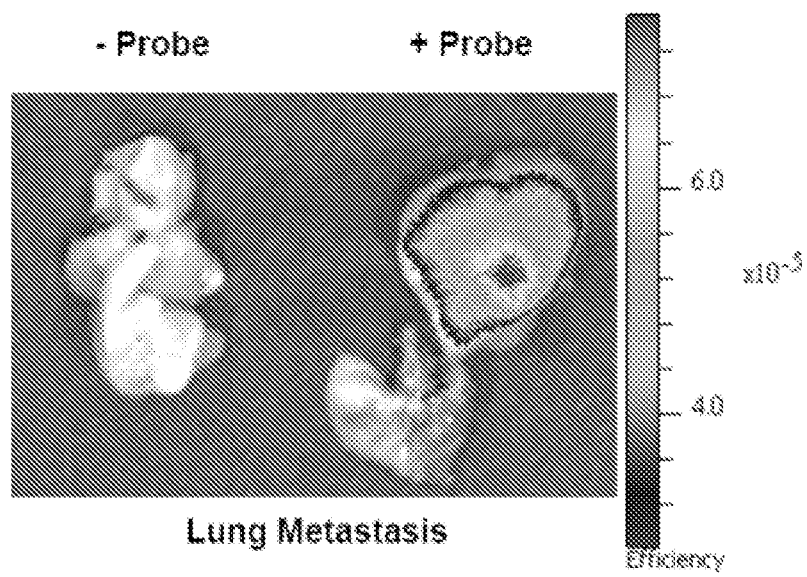
Figure 20C
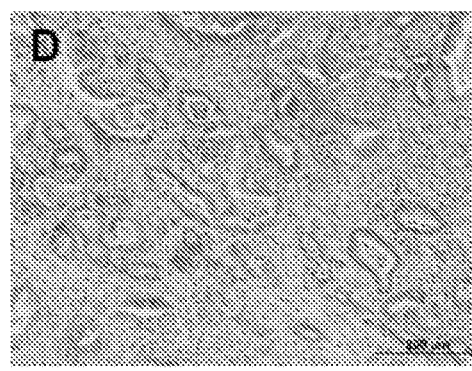
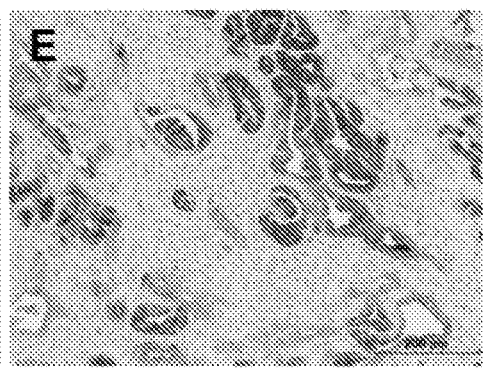
Figure 20D          Figure 20E
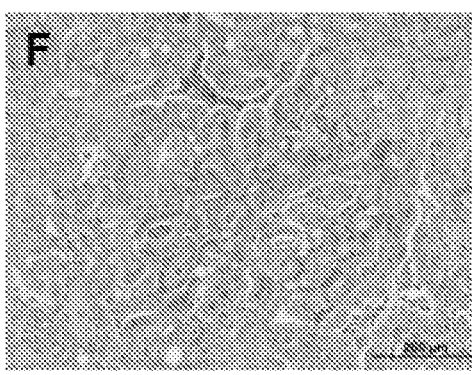
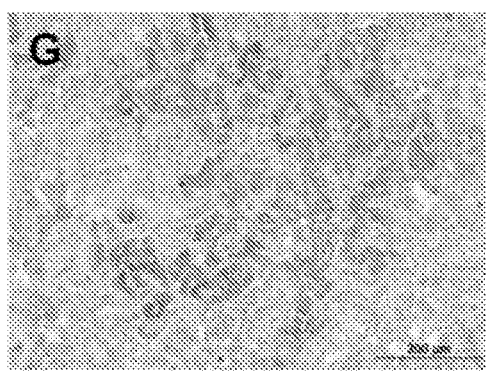
Figure 20F          Figure 20G

PROTEASE DEGRADABLE POLYPEPTIDES AND USES THEREOF

CROSS REFERENCE TO RELATED APPLICATION

This application claims the benefit of U.S. Provisional Application No. 61/418,661, filed on Dec. 1, 2010, which is incorporated by reference herein in its entirety.

STATEMENT REGARDING FEDERALLY FUNDED RESEARCH

This invention was made with government support under Grant No. CA135312 from the National Institutes of Health. The government has certain rights in the invention.

BACKGROUND

Cathepsin E (Cath E) and Cathepsin D (Cath D), members of the aspartic proteolytic enzymes family, have very similar substrate selectivity. Unlike the relatively ubiquitous Cath D, Cath E has a limited cellular localization and tissue distribution. Cath E is contained mainly within vesicular structures associated with the endoplasmic reticulum and endosomal compartments of macrophages, gastric epithelial cells, lymphocytes, microglia, and dendritic cells. In contrast to Cath E, Cath D is known to be involved in various diseases, e.g., cancer growth, metastasis, Alzheimer's Disease, and several other diseases. Although Cath E and Cath D have different tissue localization, cellular distribution, and physiological function, they share many enzymatic characteristics including molecular weight (43 kDa), catalytic mechanism, substrate preferences, proteolytic conditions, and inhibition susceptibility. Both of them are aspartic endopeptidases, which prefer hydrophobic amino acid residues at P1 and P1' positions of the scissile bond. Their optimal pH of proteolysis is between 3.5 and 5.0. A wide variety of peptidomimetic inhibitors are known for Cath E, but none can provide satisfactory discrimination against Cath D.

There are numerous methods of delivering therapeutics to subjects. These methods, however, are associated with multiple issues including toxicity, degradation of the therapeutic agent, and limited duration of efficacy of the therapeutic agent.

SUMMARY

Provided herein are polypeptides that are selectively cleaved by cathepsin E. The polypeptides optionally comprise a fluorescent donor moiety, an energy acceptor moiety, and an amino acid sequence comprising a Leucine-Proline or Leucine-X-Proline linkage at a scissile bond of the polypeptide, wherein X is an amino acid residue. The amino acid sequence comprising the Leucine-Proline or Leucine-X-Proline linkage is positioned between the fluorescent donor moiety and the energy acceptor moiety. The scissile bond is selectively cleaved by cathepsin E. Cleavage of the scissile bond results in fluorescence.

Also provided are methods of detecting cathepsin E. The methods comprise contacting cathepsin E with the polypeptides provided herein and detecting fluorescence. Fluorescence indicates the presence of cathepsin E.

Also provided are methods of diagnosing cancer in a subject. The methods comprise administering to the subject the polypeptides provided herein and detecting fluorescence in the subject above background. An increase in fluorescence in the subject above background indicates the subject has cancer.

Further provided are methods of detecting cancer or a pre-cancerous condition in a subject previously treated for a cancer. The methods comprise contacting a cell of the subject with the polypeptides provided herein and detecting fluorescence in the subject above background. An increase in fluorescence above background indicates the subject has cancer or a pre-cancerous condition.

Further provided are methods of monitoring the effectiveness of a cancer treatment in a subject being treated for cancer. The methods comprise contacting a cell of the subject at various time points with the polypeptides provided herein and detecting a level of fluorescence. A decreasing level of fluorescence indicates that the treatment is effective and an unchanged or increasing level of fluorescence indicates that the treatment is ineffective.

Further provided are methods of treating or preventing a disease characterized by expression of protease in a subject. The methods comprise identifying a subject with or at risk of developing a disease characterized by the expression of a protease and administering to the subject a multilayered nanoparticle. The multilayered nanoparticle comprises at least one layer of a therapeutic agent and at least one layer of a protease degradable polypeptide, wherein administration of the multilayered nanoparticle treats or prevents the disease characterized by the expression of the protease.

Also provided are methods of localizing in a subject a disease characterized by the expression of a protease. The methods comprise administering to the subject a multilayered nanoparticle, wherein the multilayered nanoparticle comprises at least one layer of a detectable agent and at least one layer of a protease degradable polypeptide, and localizing the multilayered nanoparticle by detecting the presence of the detectable agent in the subject.

Also provided are multilayered nanoparticles comprising at least one layer of a therapeutic agent and at least one layer of a protease degradable polypeptide. The multilayered nanoparticle can comprise a negatively charged nanoparticle core or capsule coated with alternating layers of positively charged protease degradable polypeptides and negatively charged therapeutic agents. Also provided are methods of using these nanoparticles, including, for example, in a method of treating or preventing a disease characterized by expression of a protease in a subject. The method includes administering to the subject a multilayered nanoparticle, wherein the multilayered nanoparticle comprises at least one layer of a therapeutic agent and at least one layer of a protease degradable polypeptide, wherein administration of the multilayered nanoparticle treats or prevents the disease characterized by the expression of the protease. Optionally, the subject is identified with or at risk of developing a disease characterized by the expression of a protease.

The details are set forth in the accompanying drawings and the description below. Other features, objects, and advantages are apparent from the description and drawings, and from the claims.

Without enzymes, fluorescence intensities of all tested substrates remain at the base line level. Values represent the mean of triplicate measurements.

Figure 2:
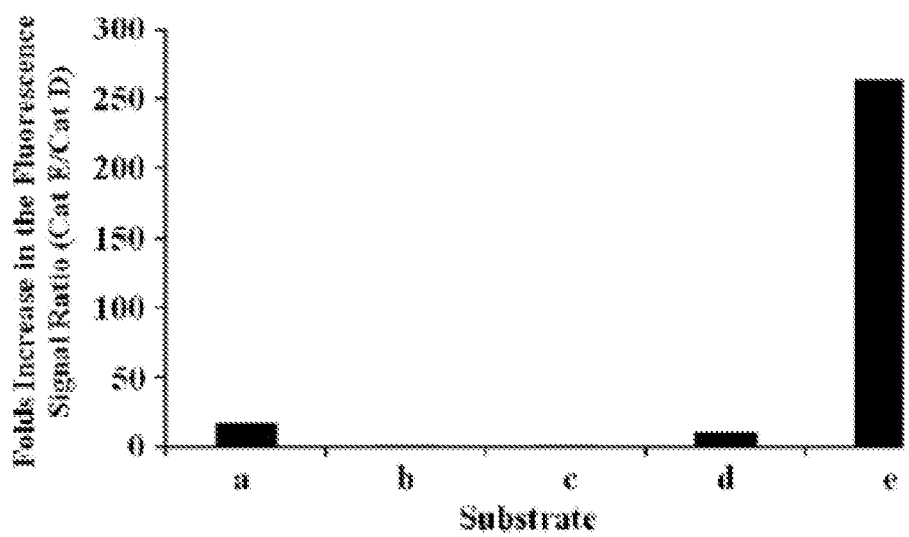

FIG. 2 shows a profile of net fluorescence signal ratio (Cath E/Cath D) of substrates a-e encountered at 1 minute after starting the enzymatic catalytic cleavage. Net fluorescence signals represent the signals after correction for the substrates quenched background signals.

Figure 3A:
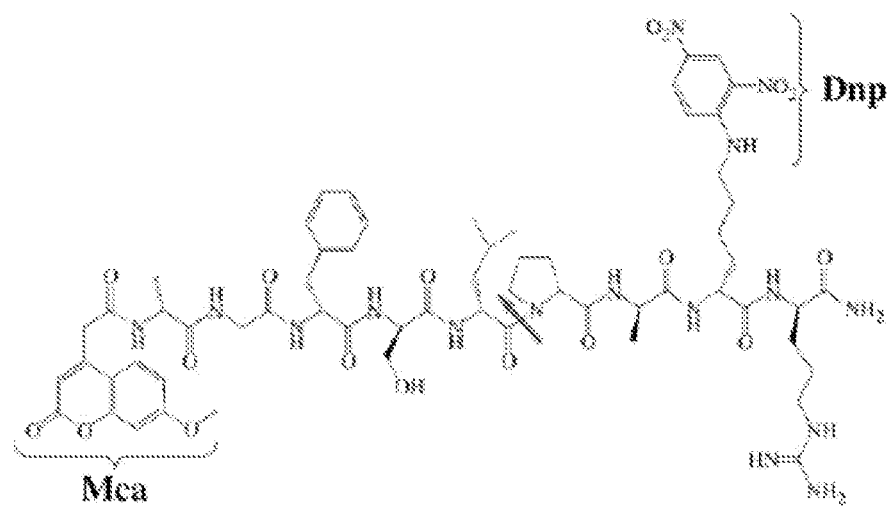
Figure 3B:
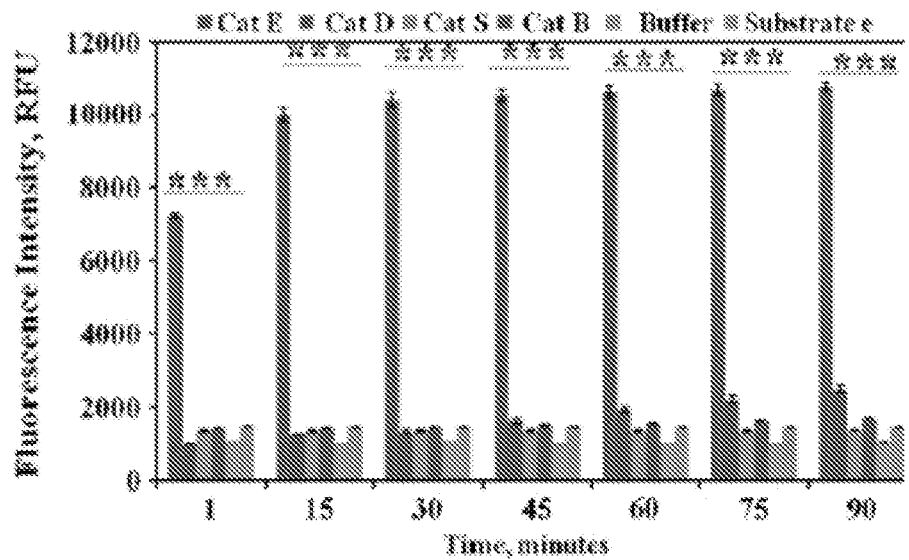

FIG. 3A shows the structure of the intramolecular quenched substrate e, Mca-Ala-Gly-Phe-Ser-LeuPro-Ala-Lys(Dnp)-D-Arg-CONH2 (SEQ ID NO:1).  indicates the scissile bond. FIG. 3B shows the change in the fluorescence intensity of substrate e (200 μM) during incubation with 23 pmol of Cath E, Cath D, Cath S and Cath B in 50 mM NaOAc buffer of pH 4.0 for Cath E and D and 100 mM NaOAc buffer of pH 6.5 for Cath S and Cath B. Values represent the mean of at least three independent experiments. Error bars represent the upper and lower values of the standard error mean (SEM). Asterisks represent the statistical significance of the two-tailed P-values (***P≤0.001).

Figure 4A:
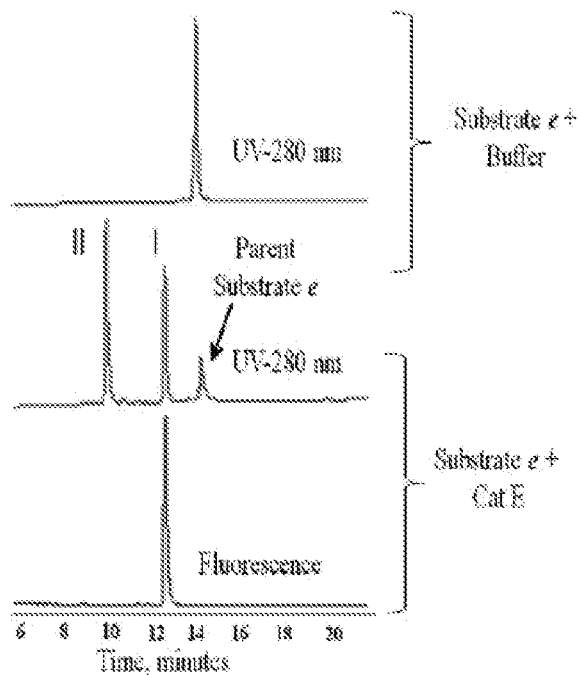
Figure 4B:
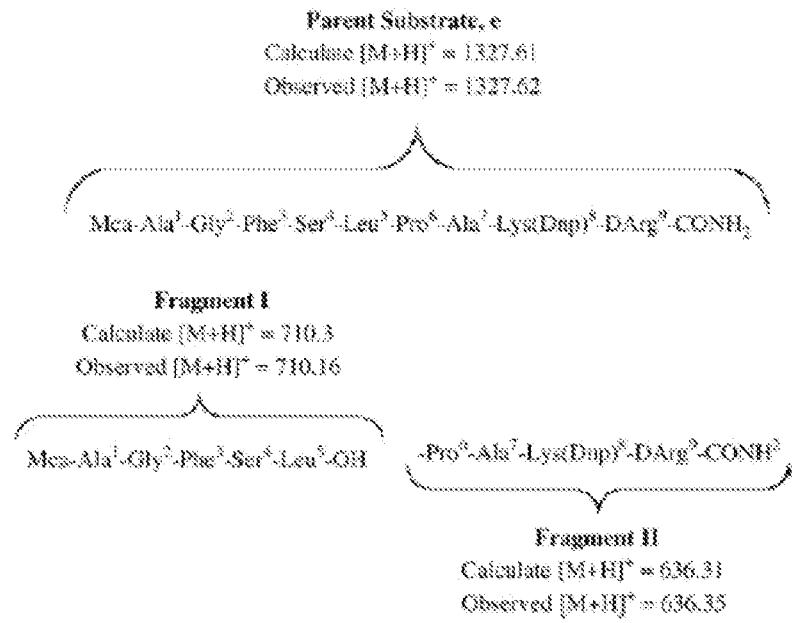

FIG. 4A shows a reverse phase high pressure liquid chromatograph (RP-HPLC) profile of peptide fragments obtained after digestion of 100 μM fluorogenic substrate e with Cath E (~119 pmol) in 50 mM sodium acetate buffer, pH 4.0, 150 mM NaCl at 37° C. for 3 hours. UV absorbance detected at 280 nm. FIG. 4B shows the identified proteolytic fragments (SEQ ID NOs:21 and 22) of substrate e (SEQ ID NO:1) and their electrospray ionization-mass spectrometry (ESI-MS) characteristics.

Figure 5A:
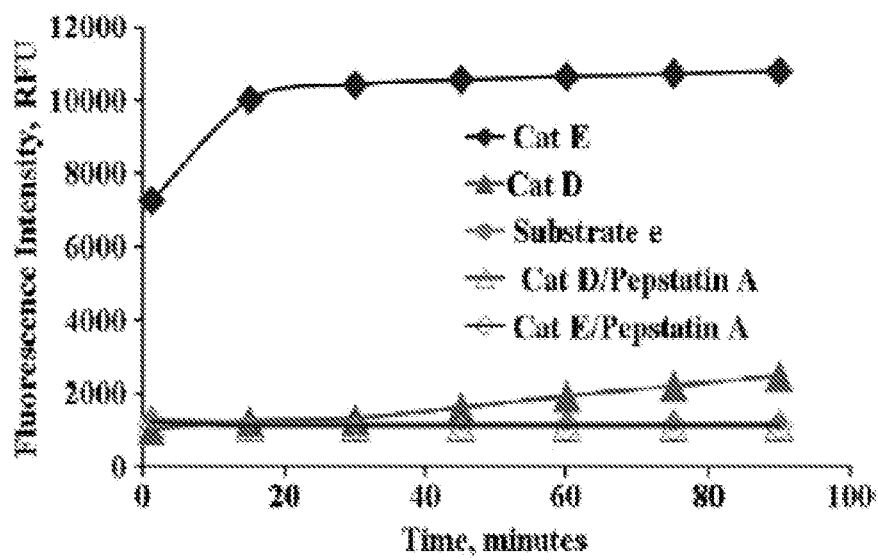
Figure 5B:
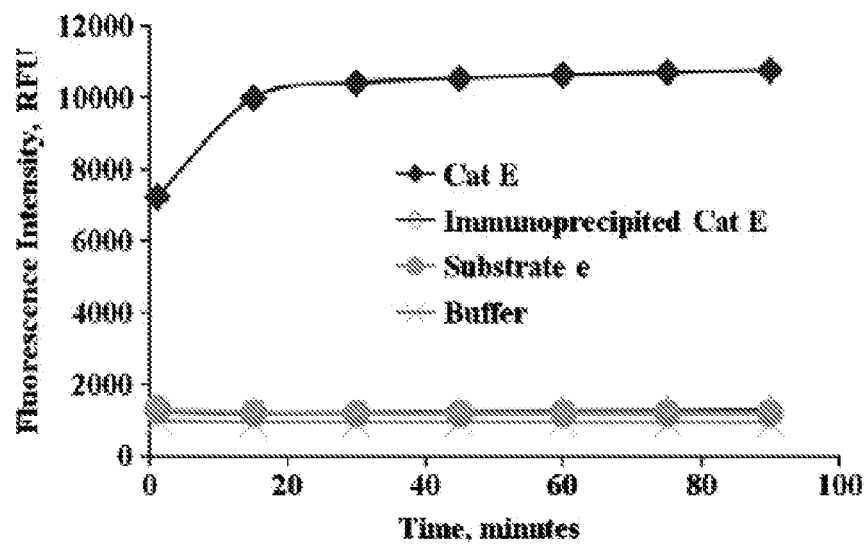

FIG. 5 shows the effect of inhibition of the enzymatic catalytic activity of Cath E and Cath D. Substrate e (200 μM) is in a 150 mM NaCl, 50 mM NaOAc buffer (pH 4.0) with 1 μL of 1 mM pepstatin A/methanol (FIG. 5A) and selective immunoprecipitation using a Cath E specific antibody in 1×PBS (FIG. 5B). All fluorescent measurements were collected with $\lambda_{ex}$=340 nm and $\lambda_{em}$=405 nm.

Figure 6A:
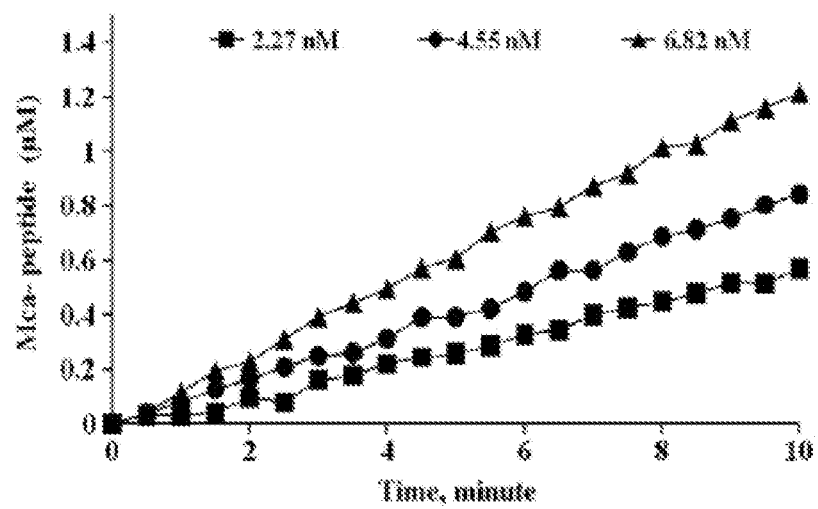
Figure 6B:
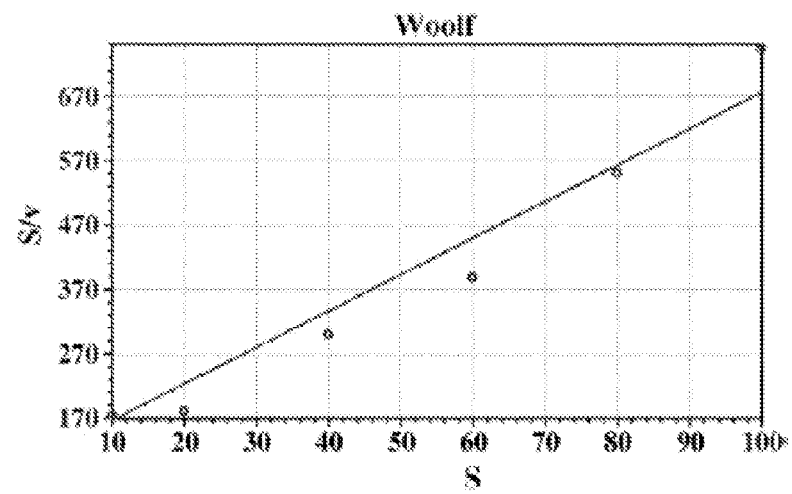

FIG. 6A shows a dose response for proteolysis. Substrate e (10 μM) was incubated with various amounts of Cathepsin E (2.27, 4.55 and 6.82 nM). FIG. 6B shows Hanes-Woolf kinetic transformation diagrams of Cathepsin E (6.82 nM). Values represent the means of triplicate measurements.

Figure 7:
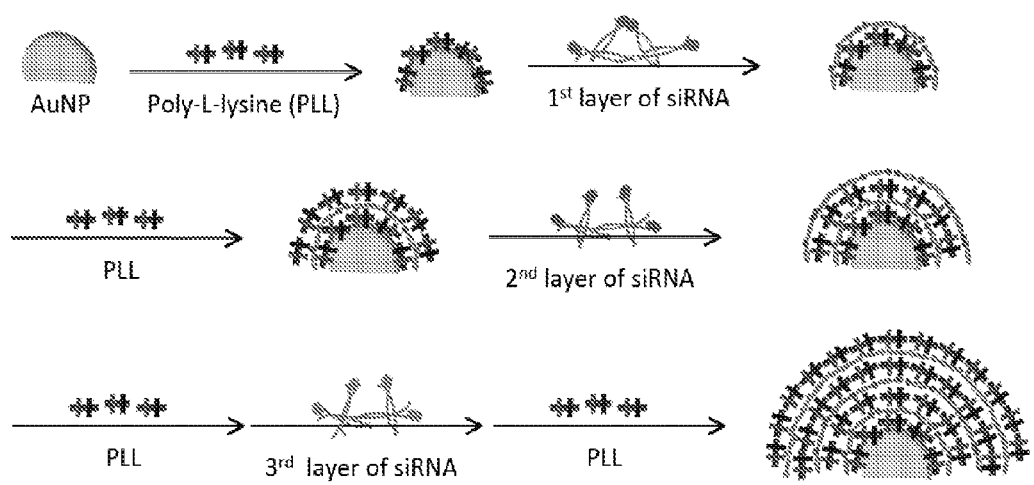

FIG. 7 shows a schematic demonstrating a method used for the preparation of multilayered siRNA coated AuNPs (sRAuNPs) using siRNA and PLL as the charged polyelectrolytes.

Figure 8A:
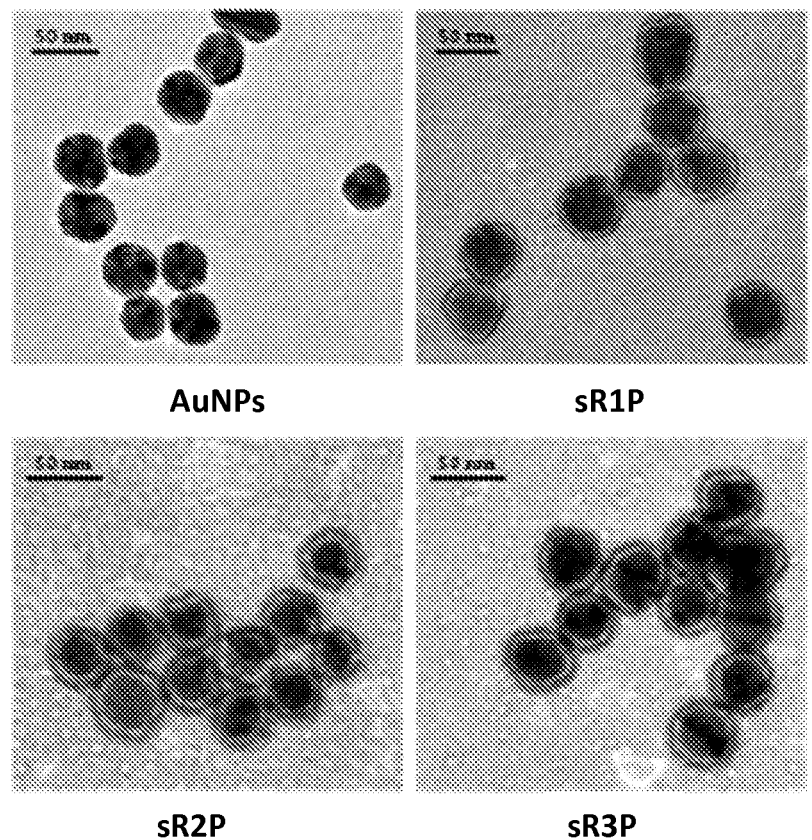
Figure 8B:
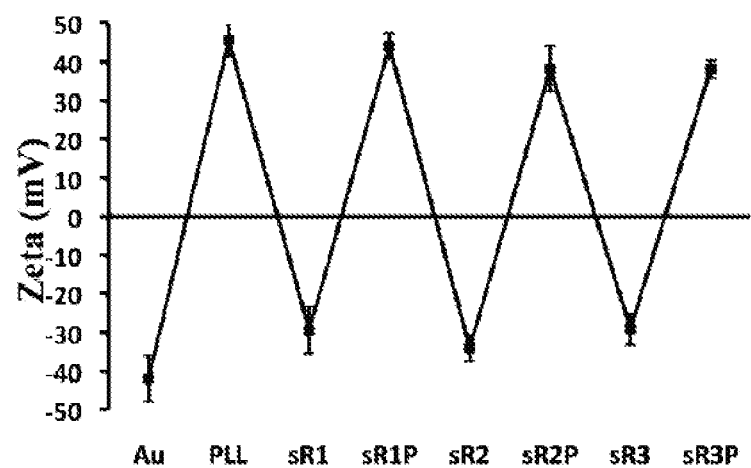

FIG. 8 shows the characterization of sRAuNPs. FIG. 8A shows transmission electron microscope (TEM) images of bare AuNPs and polyelectrolyte coated AuNPs. Negative staining by methylamine tungstate is used for all images. FIG. 8B shows a graph of the zeta-potential after each coating of polyelectrolytes. The values represent the standard deviation of three independent experiments.

Figure 9A:
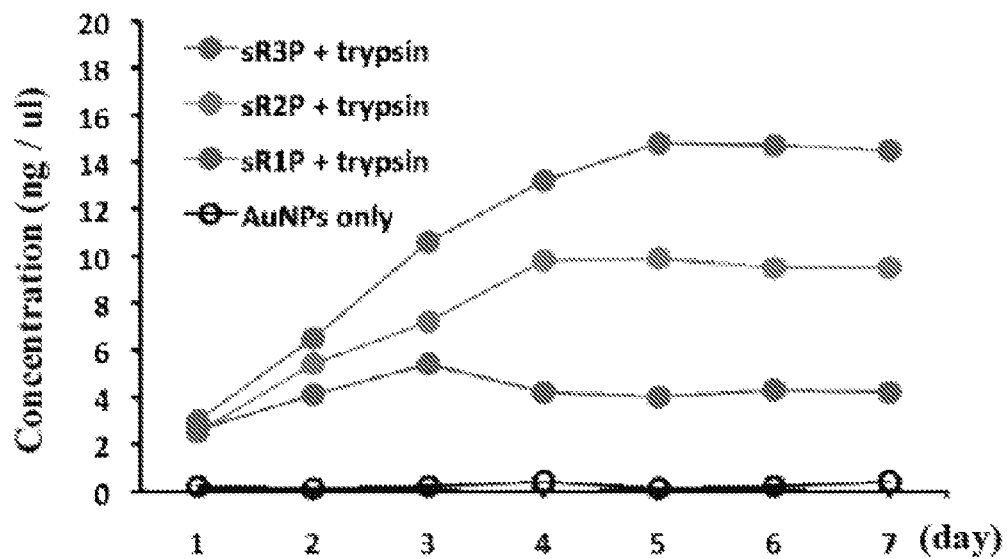
Figure 9B:
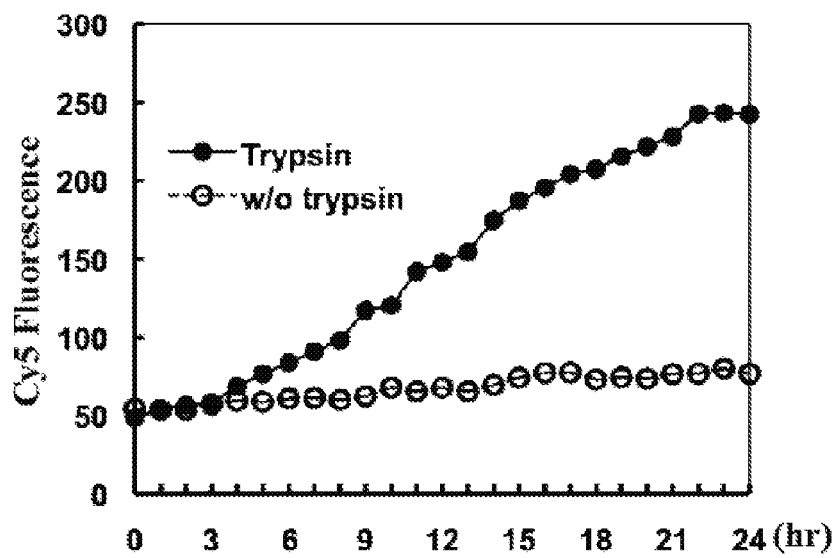

FIG. 9 shows the release of siRNA after proteolytic cleavage of poly-1-lysine (PLL). FIG. 9A shows a graph demonstrating the concentration of siRNAs released in the supernatant over time. Multilayer sRAuNPs were incubated with or without trypsin in PBS and the concentration of released siRNA in supernatant was measured. FIG. 9B shows a graph demonstrating Cy5 fluorescence over time. sR1(cy5)P AuNPs were incubated in RPMI 1640 medium containing serum with or without trypsin for 24 hours and the fluorescence was examined every hour.

FIG. 10 shows the cellular uptake of sRAuNP. FIGS. 10A and 10C show real time images of the uptake of siRNA by fluorescence microscopy after 8 hour incubation with sR(cy5)P AuNPs in MDA231-luc2 (FIG. 10A) and LNCaP-luc2 (FIG. 10C). FIGS. 10B and 10D show the graphical representation of cellular uptake of siRNA for FIGS. 10A and 10C, respectively.

Figure 11A:
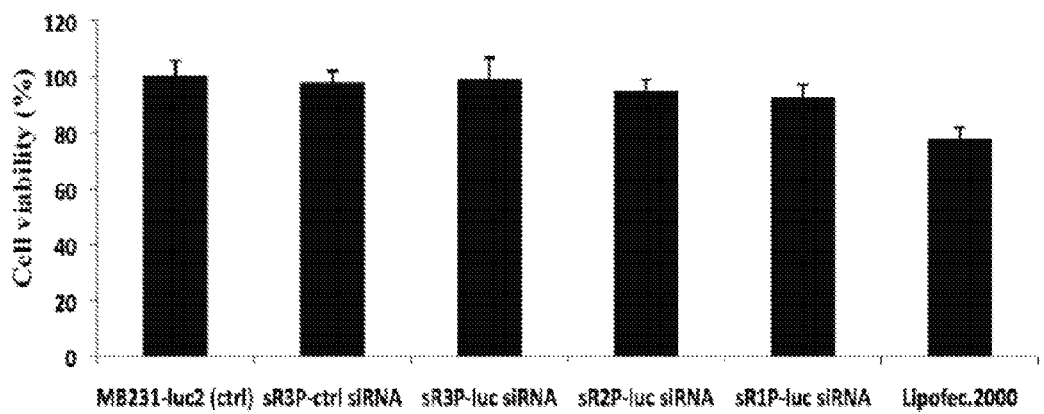
Figure 11B:
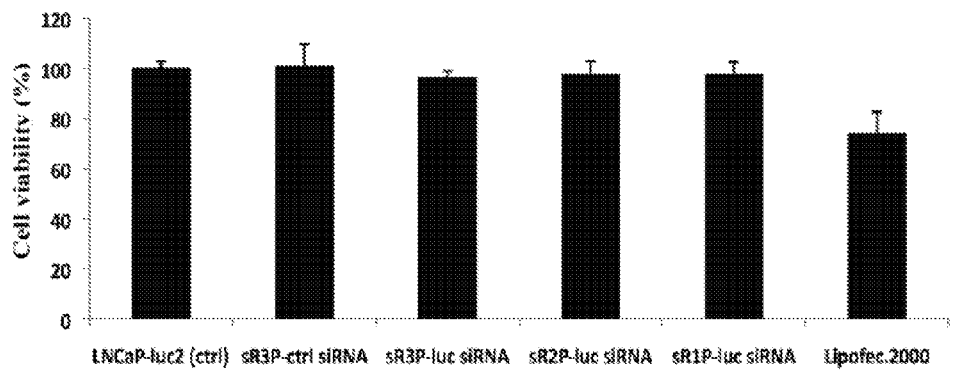

FIG. 11 shows the cytotoxicity of multilayer sRAuNPs. Cell viability was evaluated by MTT assay after transfection with multilayer sRAuNPs or Lipofectamine 2000 in MDA-MB231-luc2 (FIG. 11A) and LNCaP-luc2 (FIG. 11B). The results are representative of three independent experiments.

Figure 12A:
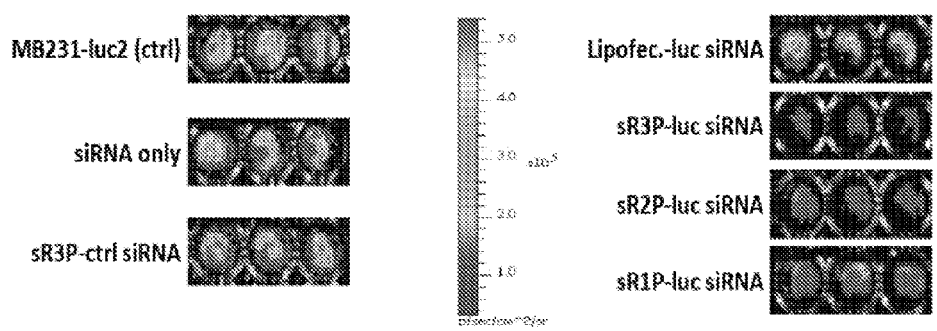
Figure 12B:
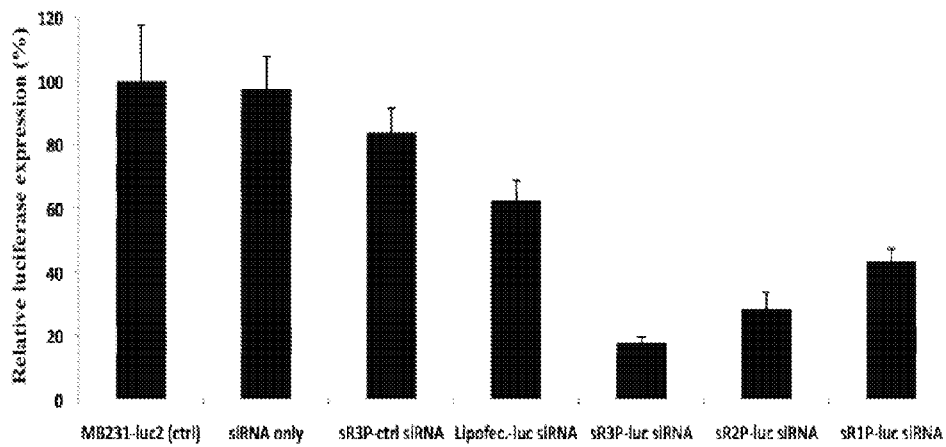

FIG. 12 shows the gene silencing effect of multilayer sRAuNP in the MDA-MB231-luc2 cell line. FIG. 12A shows images of the luminescence signal in MDA-MD231-luc2 cells after incubation with different sRAuNPs or Lipofectamine 2000 as evaluated by IVIS 200. FIG. 12B shows a graph with the values of luminescence intensity (photon/sec) in MDA-MB231-luc2 cells. The value for cells without treatment was set at 100%. The results are representative of three independent experiments.

Figure 13:
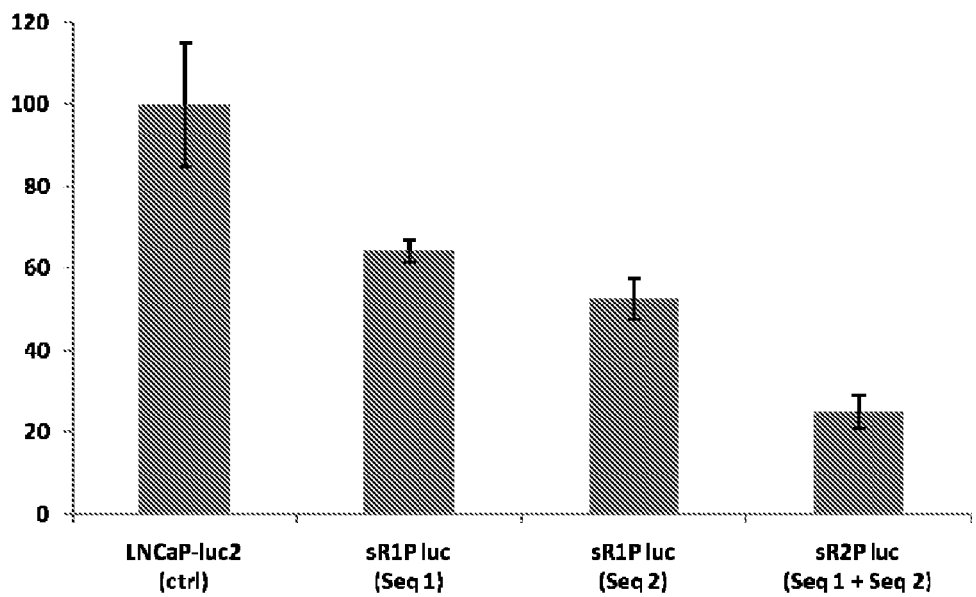

FIG. 13 shows a graph demonstrating the comparison of gene silencing effect between single siRNA and dual siRNA coated AuNPs in LNCaP-luc2 cell line. Cells were treated with luciferase targeting single siRNA particle, sR1P-luc (Seq 1) or sR1P-luc (Seq 2), or dual siRNA particle, sR2P (Seq 1+Seq 2). After incubating with or with sRAuNPs for 5 days, the luminescence of LNCaP-luc2 cells was measured immediately after addition of luciferin by IVIS 200. Value of luminescence was normalized to LNCaP-luc2 cells without treatment. Significant gene silencing effect was observed with dual siRNA coated particles (23% inhibition).

Figure 14:
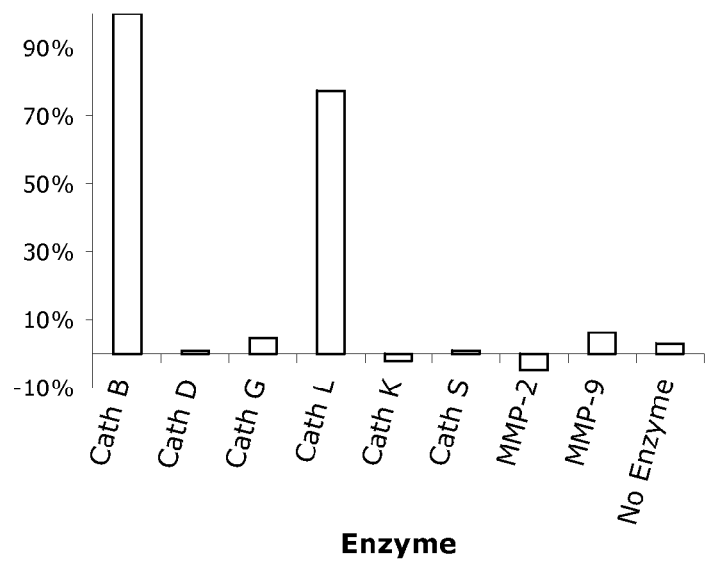

FIG. 14 shows a graph demonstrating the results of an in vitro protease selectivity assay. The probe was tested with various proteases at 37° C. for 5 hours.

Figure 15A:
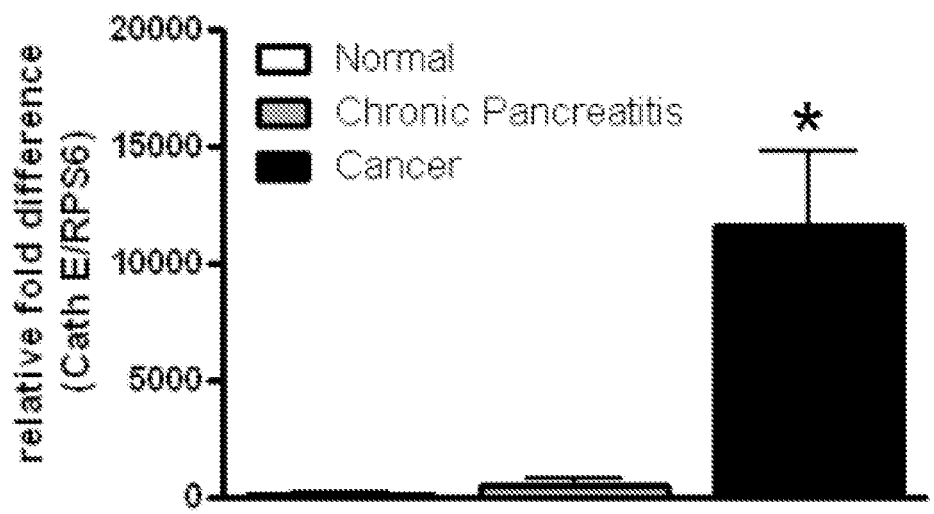
Figures 15B, 15C:
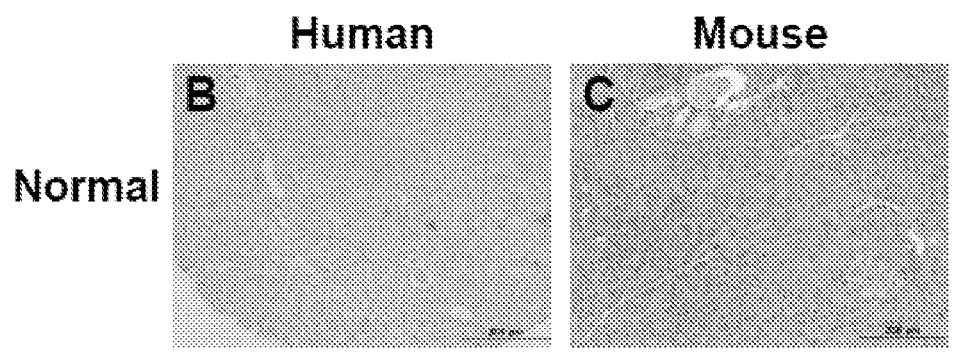
Figures 15D, 15E:
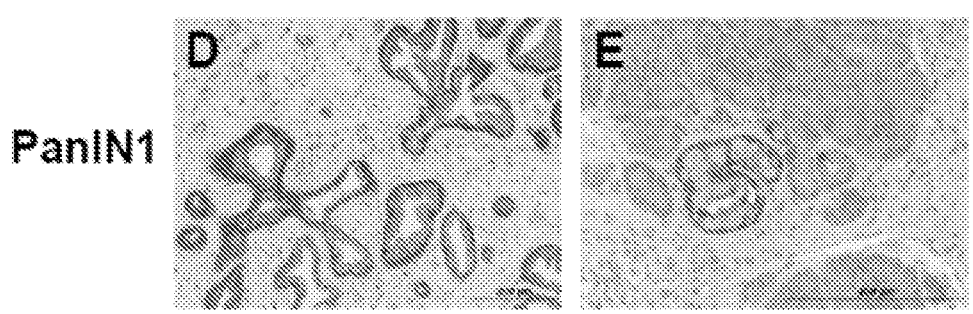
Figure 16A:
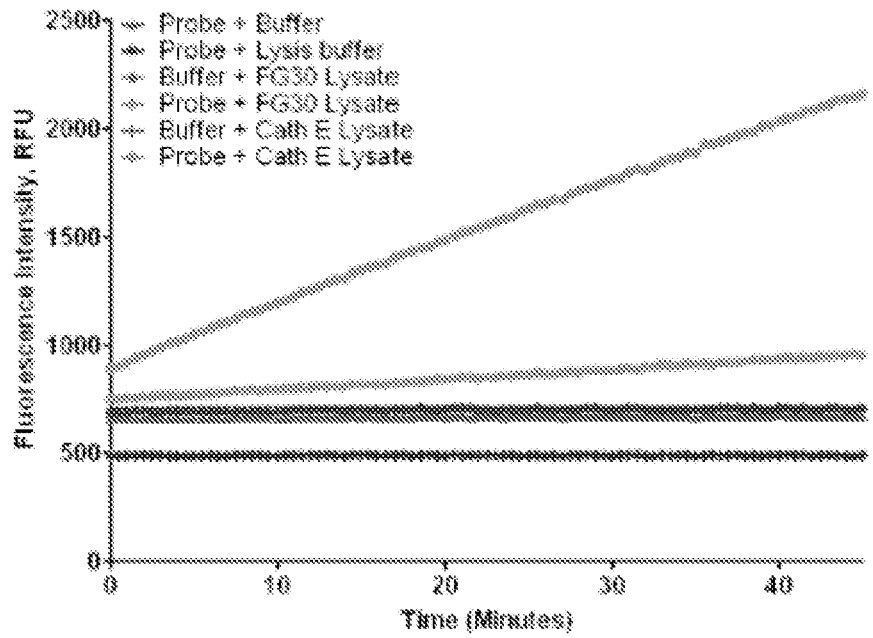
Figure 16B:
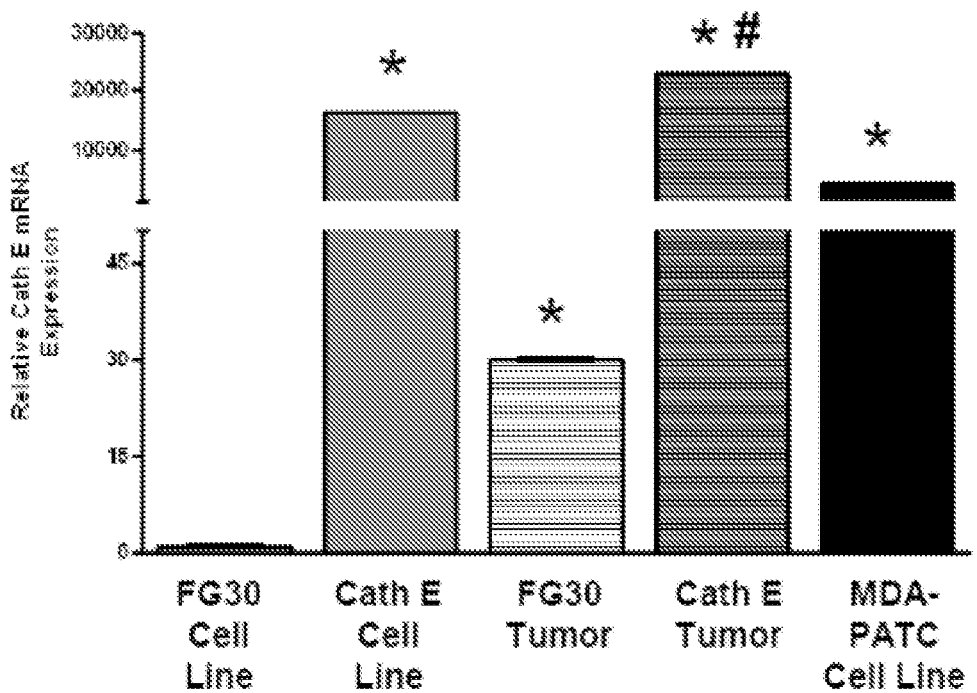
Figure 16C:
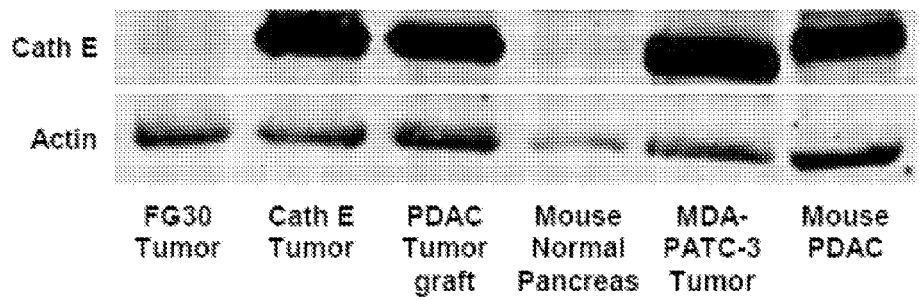
Figure 16D:
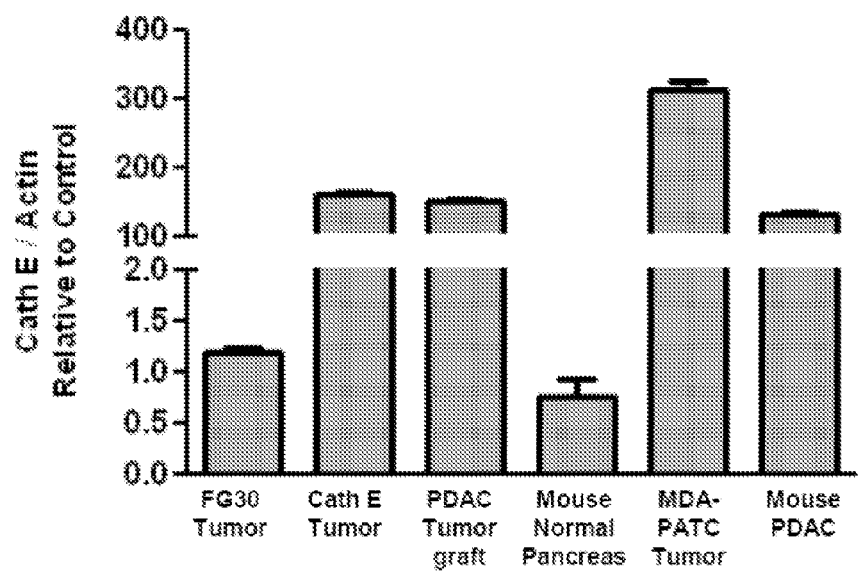
Figure 17A:
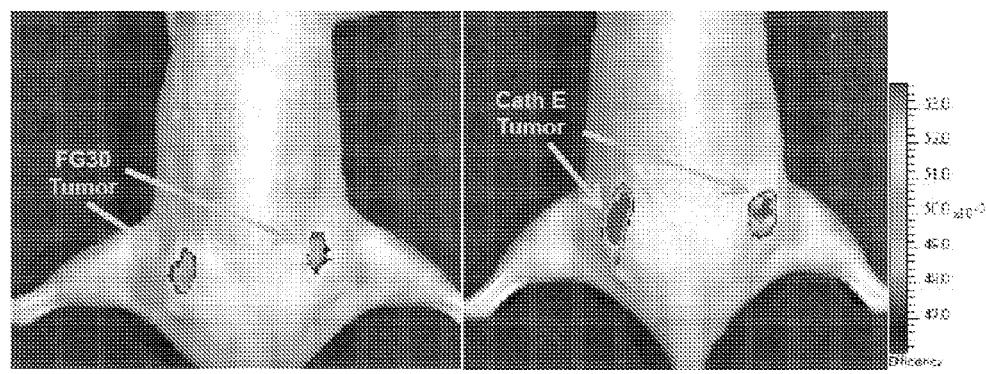
Figure 17B:
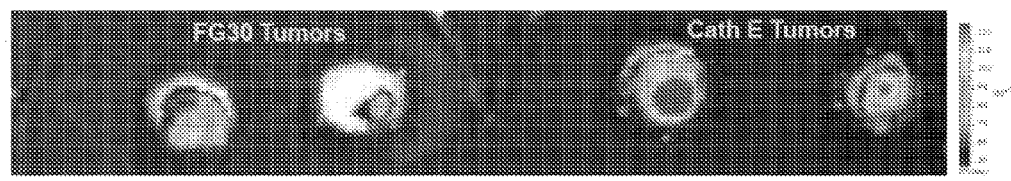
Figure 17C:
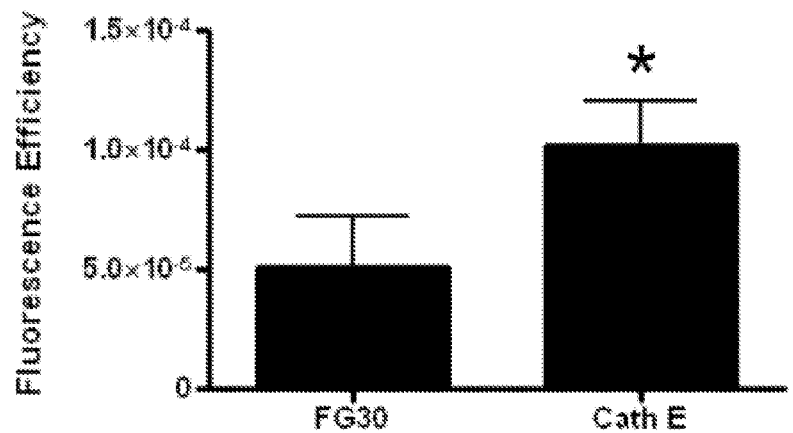
Figure 17D:
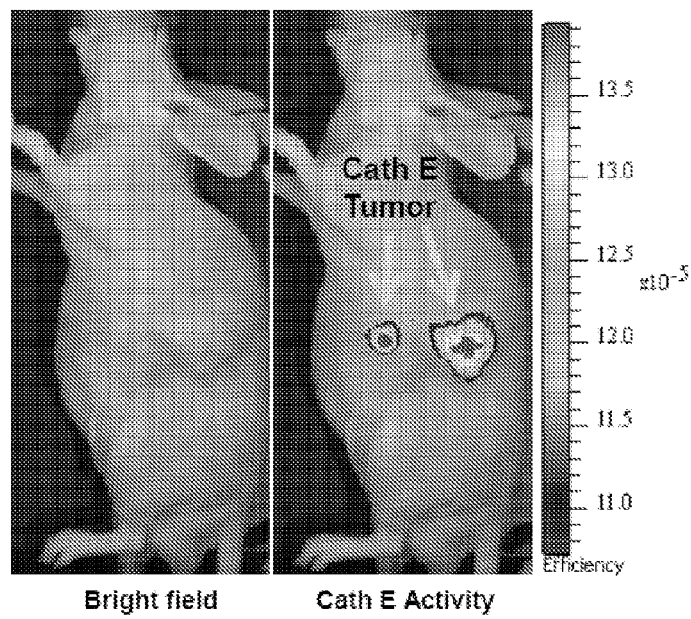
Figure 17E:
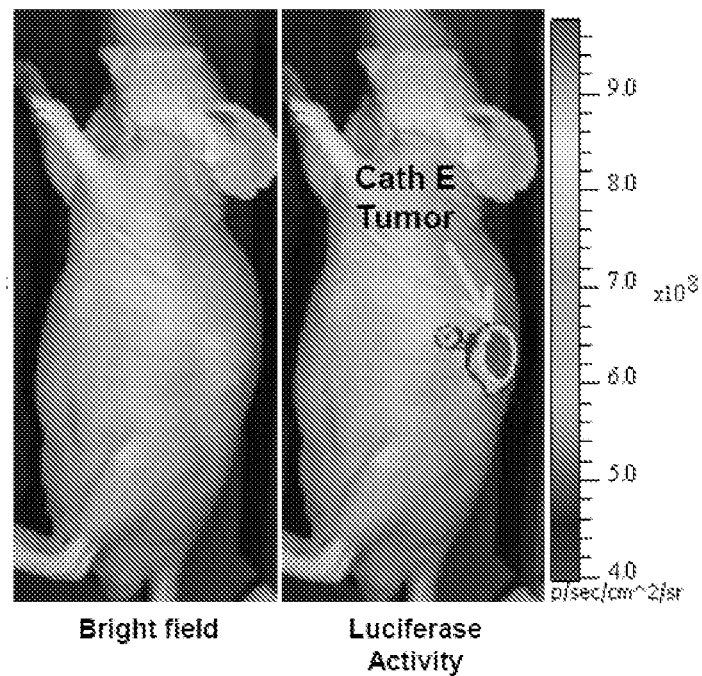

FIG. 15 shows Cath E is overexpressed in pancreatic human and mouse PanINs and PDAC. FIG. 15A shows a histogram of Taq-Man real-time PCR relative expression levels of Cath E mRNA in normal human pancreas tissue, chronic pancreatitis and pancreatic cancer samples (n=5) that were normalized to RPS6 mRNA expression (*p=0.0072 when compared to normal pancreas). Error bars represent standard deviation. FIGS. 15B, 15D, 15F, 15H, and 15J show representative images of immunohistochemical localization of Cath E in human pancreas tissue sections of normal pancreas (15B), PanIN1 (15D), PanIN2 (15F), PanIN3 (15H) and PDAC (15J), showing strong cytoplasmic Cath E expression on PanINs and cancer cells but not on normal pancreas. FIGS. 15C, 15E, 15G, 15I, and 15K show representative images of Cath E immunohistochemical localization of mouse pancreas tissue sections from wild type mouse (15C), GEMM with PanIN1 (15E), GEMM with PanIN2 (15G), GEMM with PanIN3 (15I) and GEMM PDAC (15K). Scale bar as shown in μm.

FIG. 16 shows Cath E activity can be detected efficiently in vitro and correlates with Cath E expression levels. FIG. 16A shows a change in the fluorescence intensity of the Cath E-activatable imaging probe (1 nmole) during incubation with cell lysate from MPanc96 pancreatic cancer cell lines stably transfected with lentiviral vector only (FG30) and Cath E full length lentiviral construct (Cath E). FIG. 16B shows a histogram of relative Cath E mRNA expression in Mpanc96-FG30, Mpanc96-Cath E cultures in vitro or grown in vivo as well as a primary PDAC cell line (MDA PATC-3). The cells were assessed for Cath E mRNA expression by real time PCR, relative expression levels are shown after normalization with 18S gene and calibration with Mpanc96-FG30 cell line culture in vitro. Error bars indicate coefficient of variation (n=3). (* p<0.05 when compared to Mpanc96-FG30 cell line and #p<0.05 when compared to Mpanc96-FG30 tumors). FIG. 16C shows a Western blot of Cath E expression in lysates from mouse subcutaneous tumors from cell lines used in FIG. 16A. Human tumor graft, normal mouse pancreas, orthotopic model using primary cell line (MDA-PATC-3) and GEMMs (p53 conditional deletion/LSL-Kras$^{G12D}$/Pdx1-Cre Mice) were assessed for the presence of Cath E protein expression via immunoblotting of Cath E. The top panel shows representative immunoblot of Cath E and the bottom panel shows actin as loading control. FIG. 16D shows a histogram of the quantification of the immunoblot shown in FIG. 16C, which is normalized to actin expression levels and relative to MPanc96-FG30 tumor cell lysate.

FIG. 17 shows Cath E activity can be detected efficiently in vivo and correlates with Cath E expression levels. Representative in vivo (FIG. 17A) and ex-vivo (FIG. 17B) images of Cath E activity using the Cath E-activatable imaging probe in Mpanc96-FG30 (left; n=10) and Mpanc96-Cath E (right; n=10) mouse subcutaneous tumors, 48 hours post injection of the Cath E-activatable imaging probe (1 nmole). FIG. 17C shows a histogram of fluorescence quantification of ex vivo tumors from FIG. 17B (* p<0.05 when compared to Mpanc96-FG30 cell line). FIG. 17D shows a representative in vivo image showing bright field (left) and fluorescence (right) of Cath E-activatable imaging probe image from an orthotopic tumor formed using the luciferase expressing Mpanc96-Cath E cells which shows fluorescence activity localized to the tumor site. Cath E activity fluorescence signal co-localized with the luciferase signal (FIG. 17E) confirming tumor site.

FIG. 18 shows Cath E activity can be detected efficiently in human pancreatic cancer xenografts in mouse. FIG. 18A shows a representative in vivo image of human pancreatic cancer primary patient tumor grafts in mice showing brightfield (left) and fluorescence (Cath E activity) (right) signal at tumor location (n=4). FIG. 18B shows a representative ex vivo image of mouse orthotopic tumor formed from cells (MDA PATC-3) isolated from human pancreatic cancer tumor grafts (FIG. 18A) showing fluorescence signal from pancreas with tumor (bottom) compared to a pancreas without a tumor (top) as well as, kidney, muscle, bone, small intestine, and lung. (n=3). FIG. 18C shows a representative H & E staining of primary patient tumor grafts from FIG. 18A showing the presence of human tumor cells surrounded by the stromal components that characterize human pancreatic tumor. FIG. 18D shows a representative H & E staining of orthotopic pancreas tumor from FIG. 18B which shows the similar characteristics to human PDAC. Representative images of immunohistochemical localization of Cath E of normal pancreas (FIG. 18E) from pancreas imaged in FIG. 18B and tumor (FIG. 18F) from tumor imaged in FIG. 18B. Scale bar as shown in µm.

Figure 19A:
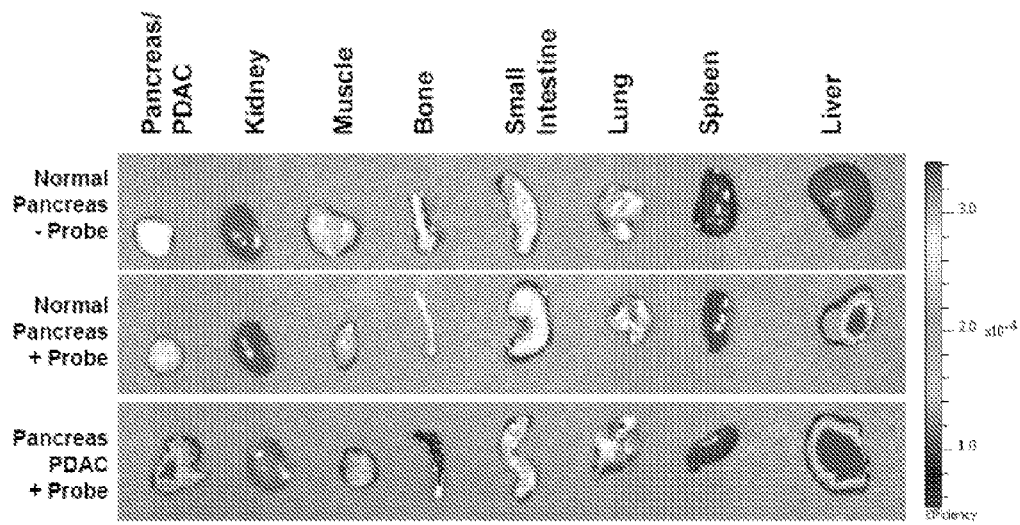
Figure 19B:
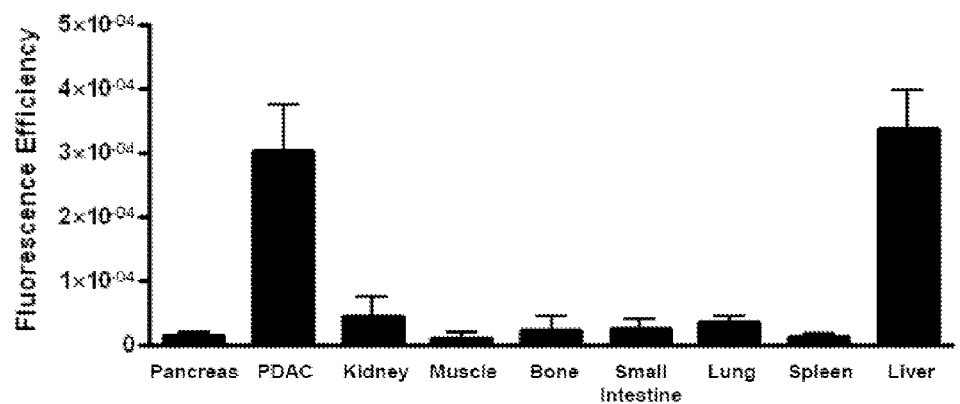

FIG. 19 shows Cath E activity in genetically engineered mouse models (GEMMs). FIG. 19A shows representative ex vivo images of control pancreas and PDAC GEMM (p53 conditional deletion/LSL-Kras$^{G12D}$/Pdx1-Cre Mice) tumor showing specific fluorescence signal from pancreas with tumor in which Cath E-activatable probe was added (bottom panel) compared to a mouse pancreas without tumor and no probe added (top panel) and a mouse pancreas without tumor but Cath E-activatable imaging probe added (middle panel) as well as, the kidney, muscle, bone, small intestine, lung, spleen, and liver from each mouse. FIG. 19B shows a histogram quantifying the ex vivo fluorescence quantification of various mice organs 48 hours after Cath E-activatable imaging probe was injected to the animals (normal pancreas, n=4; PDAC (pool of both GEMMs), n=5; and kidney, muscle, bone, small intestine, lung, spleen, and liver (n=8))

Figure 20A:
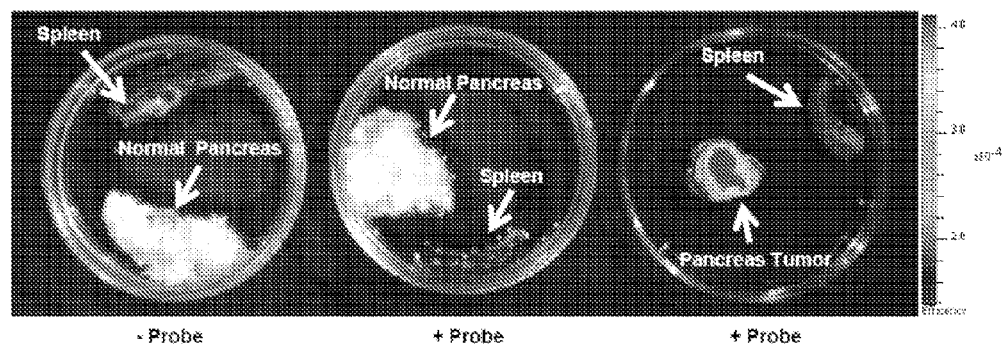
Figure 20B:
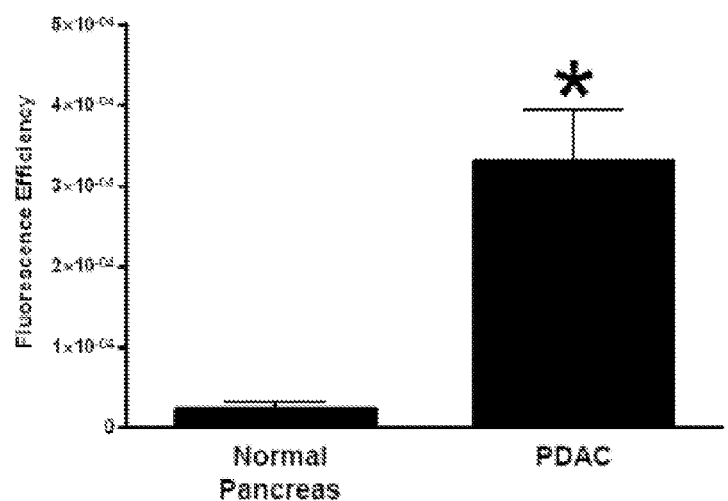

FIG. 20 shows Cath E activity can be detected efficiently in GEMMs tissues. FIG. 20A shows a representative ex vivo image of mouse normal pancreas with spleen (left) in which no Cath E-activatable imaging probe was injected, mouse normal pancreas with spleen (middle) after 48 hours of Cath E-activatable imaging probe injection, and GEMM (cLGL-KRas$^{G12V}$ with Bac-Ela-CreER mice) PDAC tumor with spleen (right) after 48 hours of Cath E-activatable imaging probe injection showing fluorescence signal specific to Cath E activity from the tumor. FIG. 20B shows a histogram of fluorescence quantification of ex vivo normal pancreas and GEMMs (pooled data from both GEMMs used) PDAC tumors showing ~15-fold increase in fluorescence in the pancreas tumors when compared to normal pancreas (n=5) (*P=0.0002). FIG. 20C shows a representative ex vivo image of lung metastasis from mice with PDAC (p53 conditional deletion/LSL-Kras$^{G12D}$/Pdx1-Cre Mice) without probe injection (left) and mice injected with Cath E-activatable imaging probe (right) showing fluorescence signal in lung metastasis when Cath E-activatable imaging probe is added (n=2). FIG. 20D shows a representative H & E staining and FIG. 20E shows a representative image of immunohistochemical localization of Cath E from tumor imaged in FIG. 20A. FIG. 20F shows a representative H & E staining and FIG. 20G shows a representative image of immunohistochemical localization of Cath E from lung metastasis imaged in FIG. 20C. Scale bar as shown in µm.

FIG. 21 shows Cath E activity can be detected efficiently in mouse pancreas with PanIN lesions. FIG. 21A shows a representative ex vivo Cath E-activatable imaging probe image of pancreas from GEMMs with normal pancreas and pancreas with PanIN lesions (cLGL-KRas$^{G12V}$ with Bac-Ela-CreER mice) and PDAC (p53 conditional deletion/LSL-Kras$^{G12D}$/Pdx1-Cre Mice) injected with Cath E-activatable imaging probe. FIGS. 21B and 21C show representative H & E staining of transgenic animals with normal pancreas and pancreas with PanINs but no tumors from FIG. 21A. FIG. 21D shows a representative image of immunohistochemical localization of Cath E from pancreas with PanINs but no tumors from FIG. 21A. FIG. 21E shows a histogram of fluorescence quantification of ex vivo pancreas showing ~3-fold increase in fluorescence in the pancreas with PanIN lesions when compared to normal pancreas (n=4) (*P=0.0058), and a significant increase in tumor fluorescence signal compared to the fluorescence signal from pancreas containing PanIN lesions but no tumor. Scale bar as shown in µm.

Figure 22:
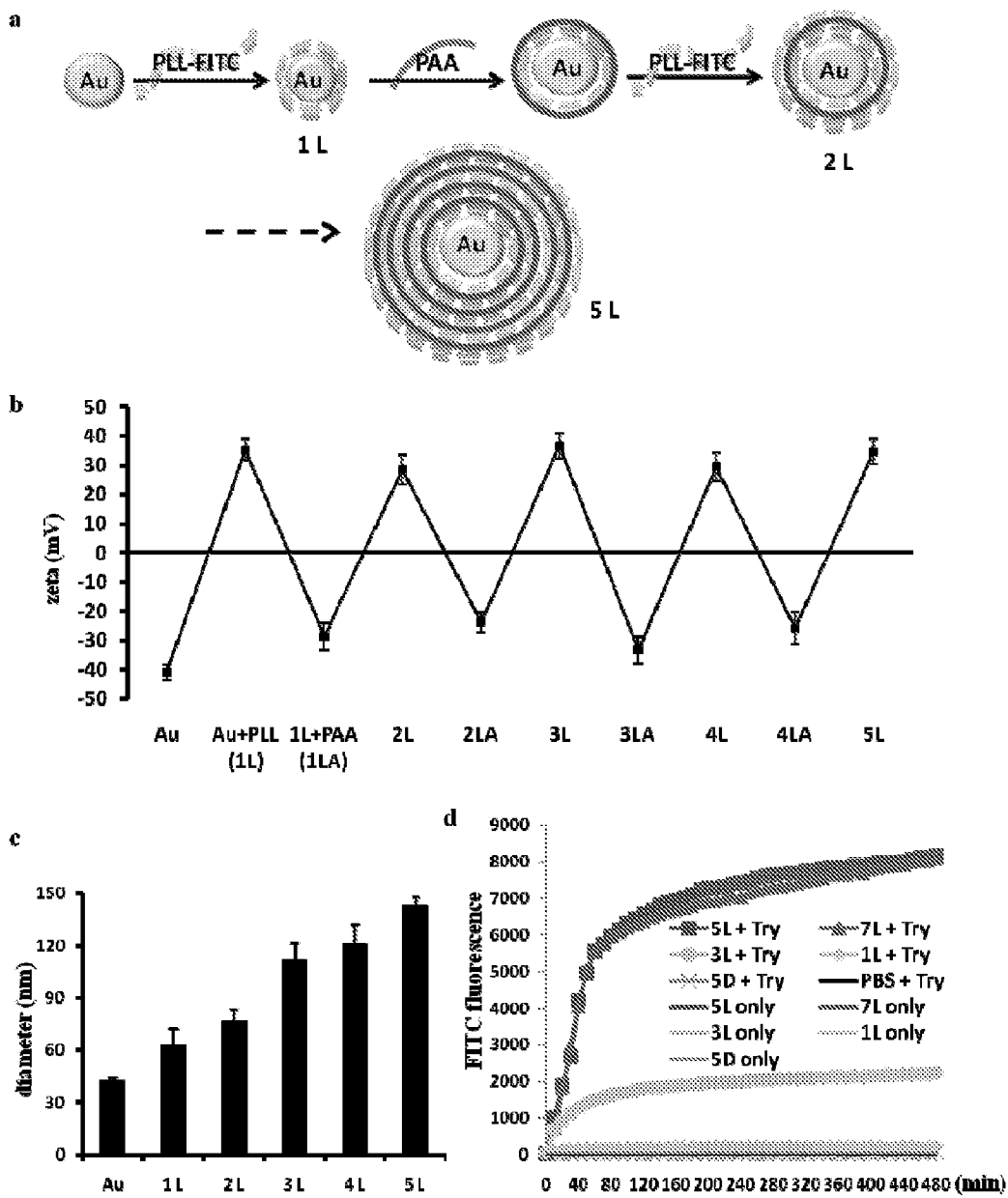

FIG. 22 shows the preparation and characterization of multilayered fluorescent AuNPs. FIG. 22A shows the preparation process for multilayered fluorescent AuNPs using PLL-FITC and PAA as the charged polyelectrolytes. FIG. 22B shows the zeta potential after each coating of polyelectrolytes. FIG. 22C shows the diameter of bare AuNPs and polyelectrolyte-coated AuNPs. FIG. 22D shows the protease-assisted FITC release from various AuNPs. Multilayered fluorescent AuNPs were incubated with or without trypsin in PBS and the fluorescence intensity was examined to 8 hours.

Figure 23:
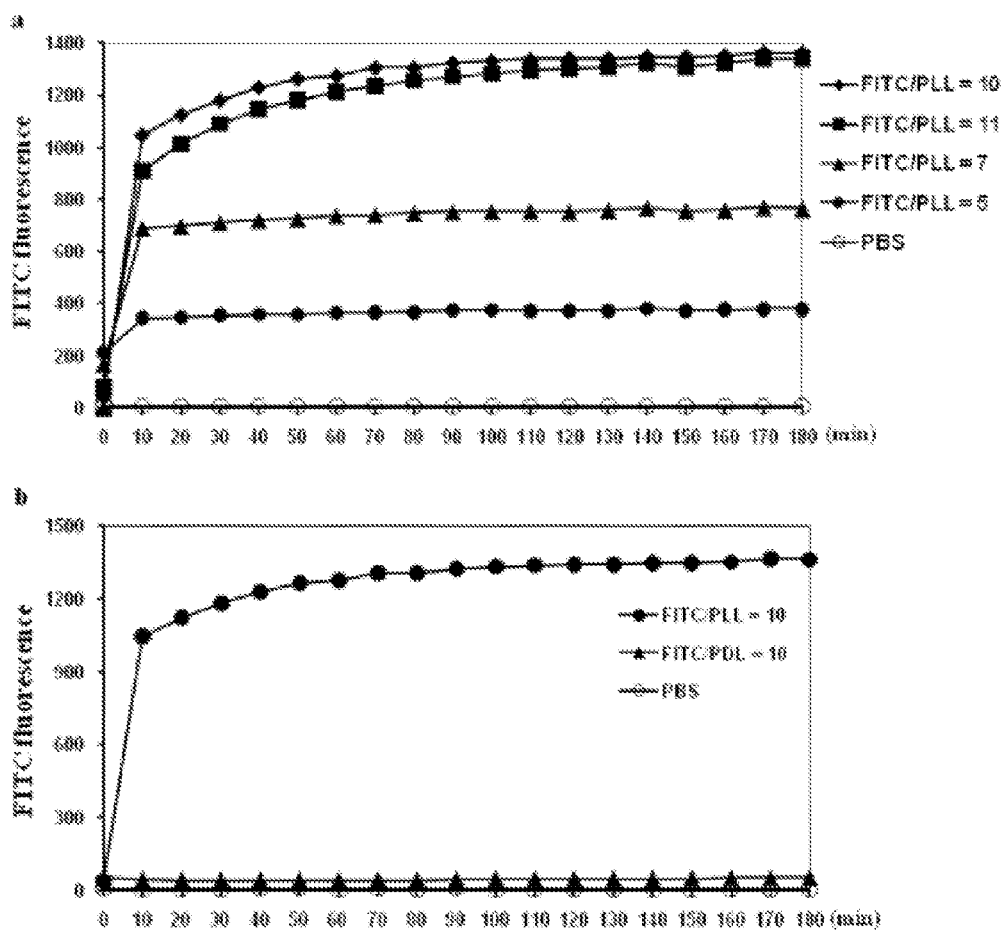

FIG. 23 shows protease-assisted cleavage of PLL or PDL conjugated with FITC. After incubation of different concentration of PLL-FITC (FIG. 23A) or PDL-FITC (FIG. 23B) with or without trypsin in PBS, the fluorescence intensity was examined until 3 hours.

Figure 24:
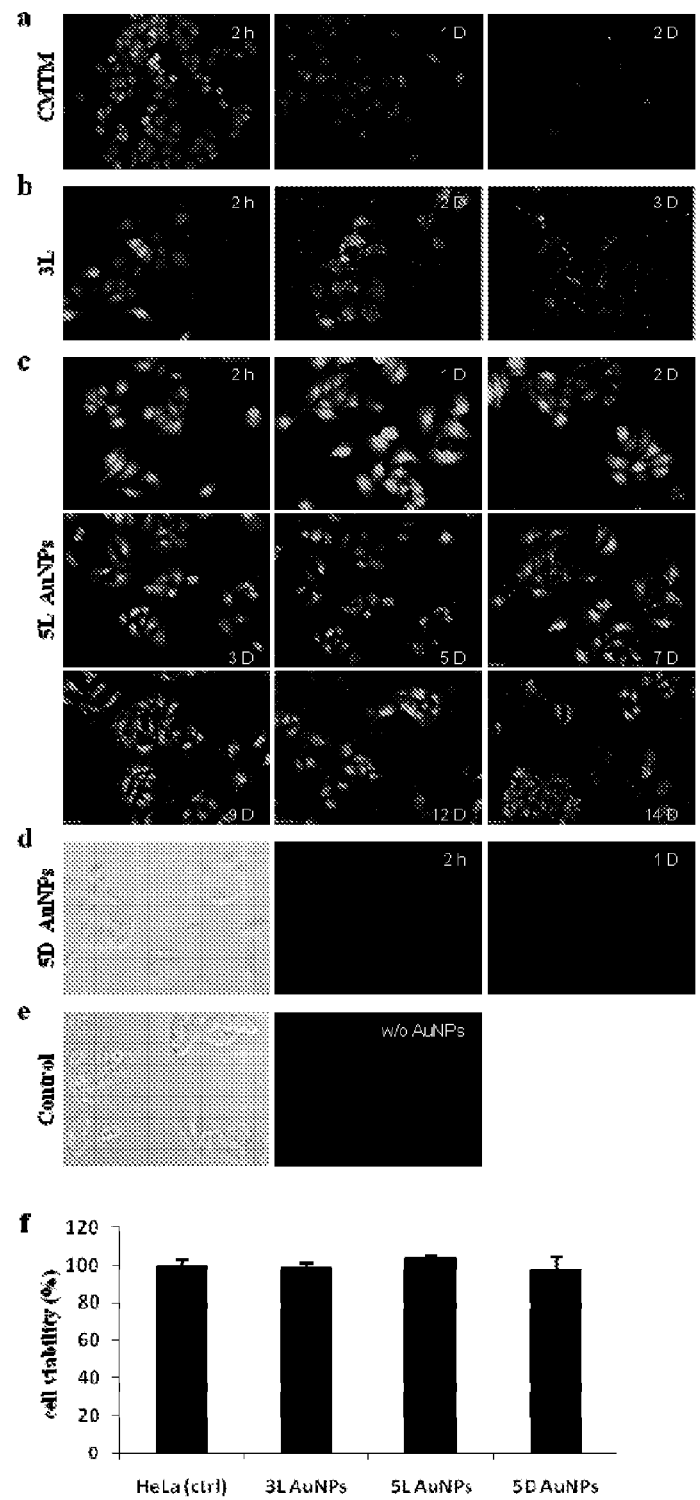

FIG. 24 shows live cell imaging and cytotoxicity in HeLa cells. After incubation for 30 minutes with cell tracker, CMTMR (FIG. 24A) or incubation for 12 hours with various multilayered fluorescent AuNPs, such as 3L (FIG. 24B), 5L (FIG. 24C), and 5D (FIG. 24D), fluorescence signal were assessed using fluorescence microscopy. Control is shown in FIG. 24E. Cell viability (FIG. 24F) was evaluated after incubation for 24 hours with various multilayered fluorescent AuNPs using CellTiter solution.

Figure 25:
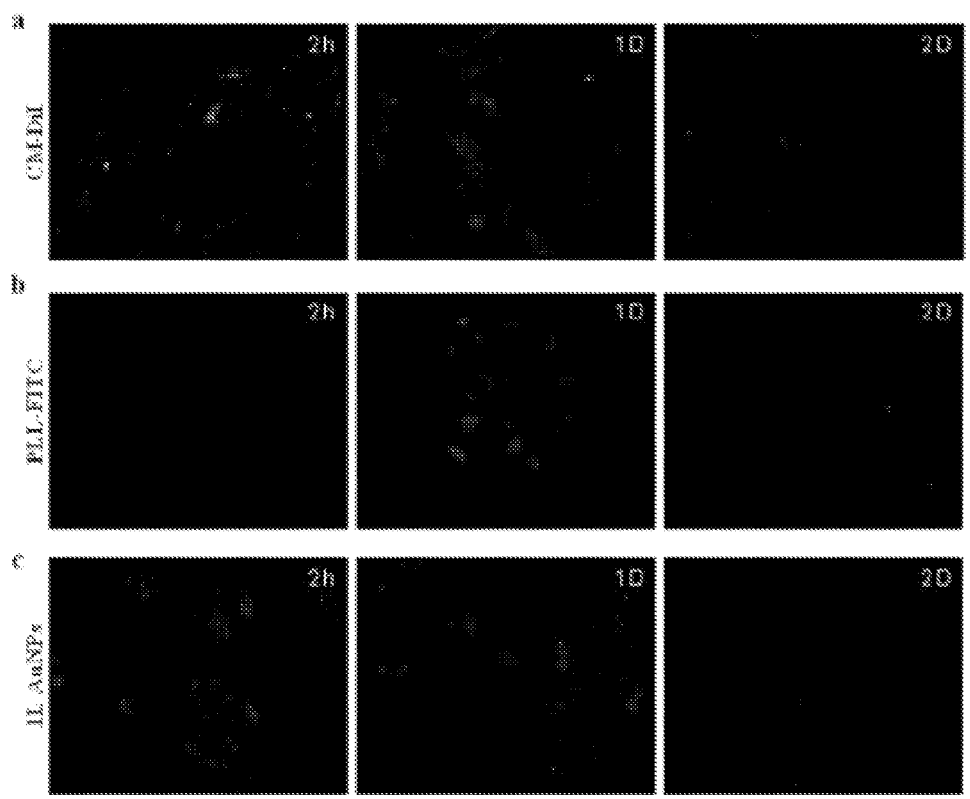

FIG. 25 shows live cell imaging in HeLa cells with time course. After incubation with CM-DiI, 2 μM (FIG. 25A) for 30 minutes, PLL-FITC (FIG. 25B) for 4 hours, or 1L AuNPs (FIG. 25C) for 12 hours, fluorescence signal was investigated with fluorescence microscopy in HeLa cells.

Figure 26:
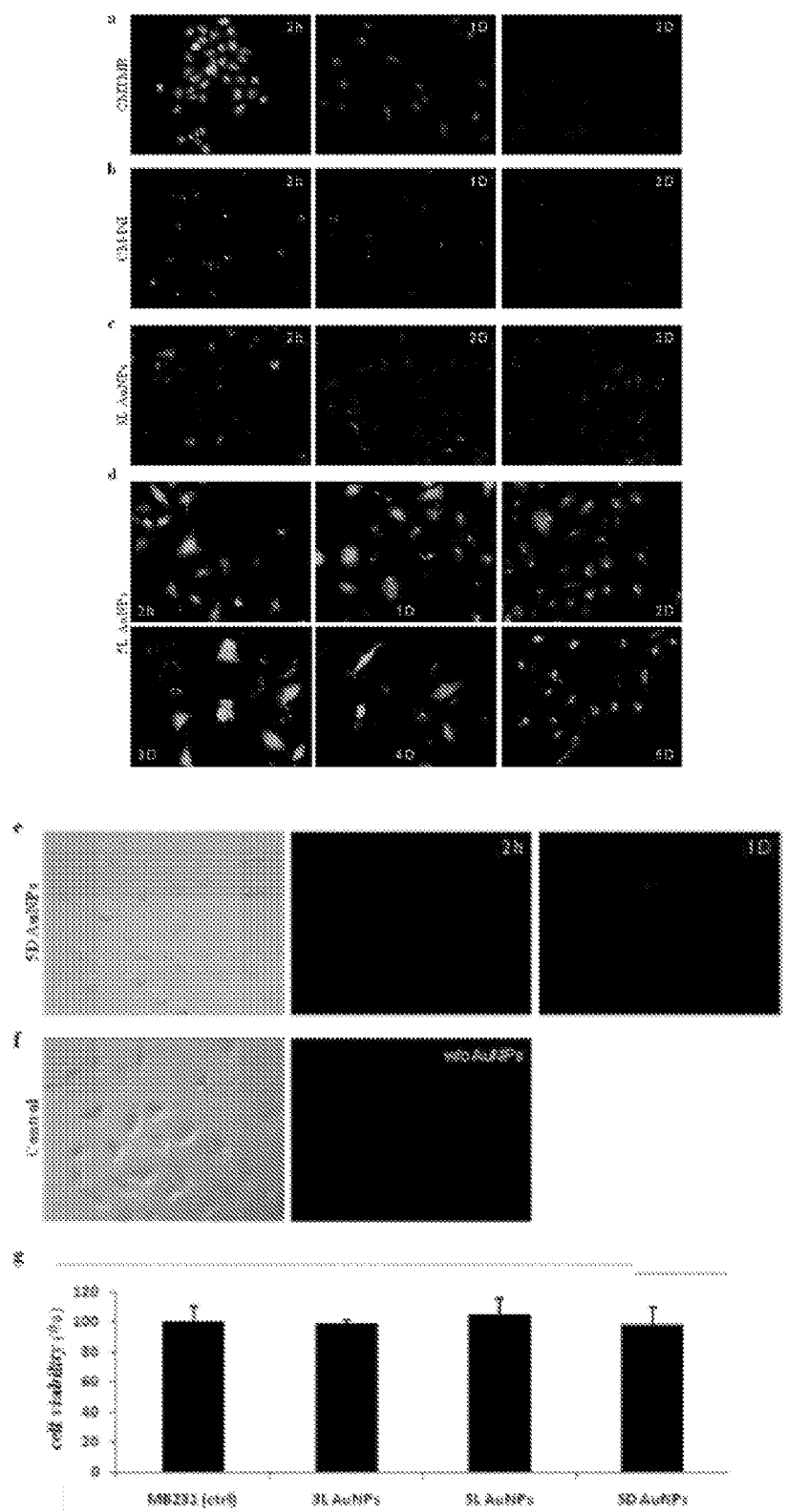

FIG. 26 shows live cell imaging and cytotoxicity in MDA-MB231 cells. After incubation with cell tracker, CMTMR, 7.5 μM (FIG. 26A) for 15 minutes, CM-DiI, 2 μM (FIG. 26B) for 30 minutes, or various multilayered fluorescent AuNPs, such as 3L (FIG. 26C), 5L (FIG. 26D) and 5D (FIG. 26E) for 12 hours, fluorescence signal was investigated with fluorescence microscopy. Control is shown is FIG. 26F. Cell viability (FIG. 26G) was also evaluated after incubation for 24 hours with various multilayered fluorescent AuNPs using CellTiter solution in MDA-MB231 cells.

Figure 27:
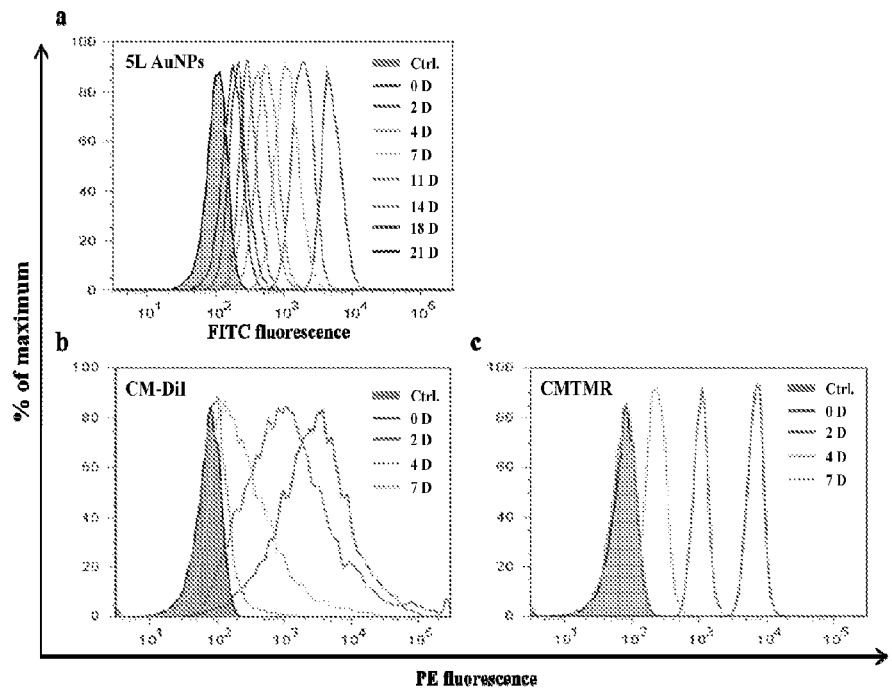

FIG. 27 shows fluorescence retention through generations in Jurkat cells. After treatment with 5L AuNPs (FIG. 27A), CM-DiI (1 μM) (FIG. 27B), or CMTMR (2 μM) (FIG. 27C), fluorescence intensity was evaluated by flow cytometry for 21 days.

Figure 28:
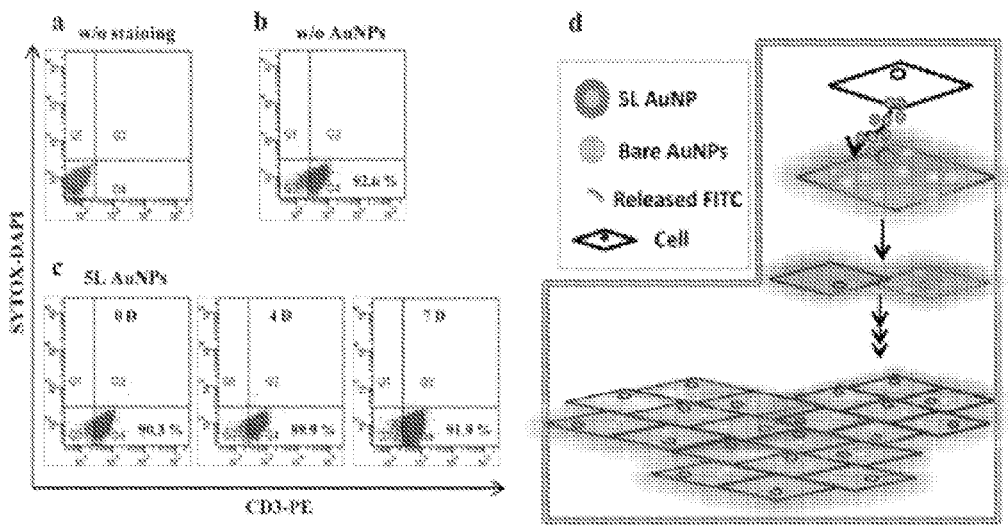

FIG. 28 shows cell phenotype and viability after treatment with 5L AuNPs in Jurkat cells. CD3 expression (PE) and cell viability (DAPI) without staining (FIG. 28A) and double staining without treatment (FIG. 28B) or treatment with 5L AuNPs (FIG. 28C) were assessed for 7 days using flow cytometry. FIG. 28D shows an illustration of cellular uptake and signal release from multilayered fluorescent AuNPs through generations.

Figure 29:
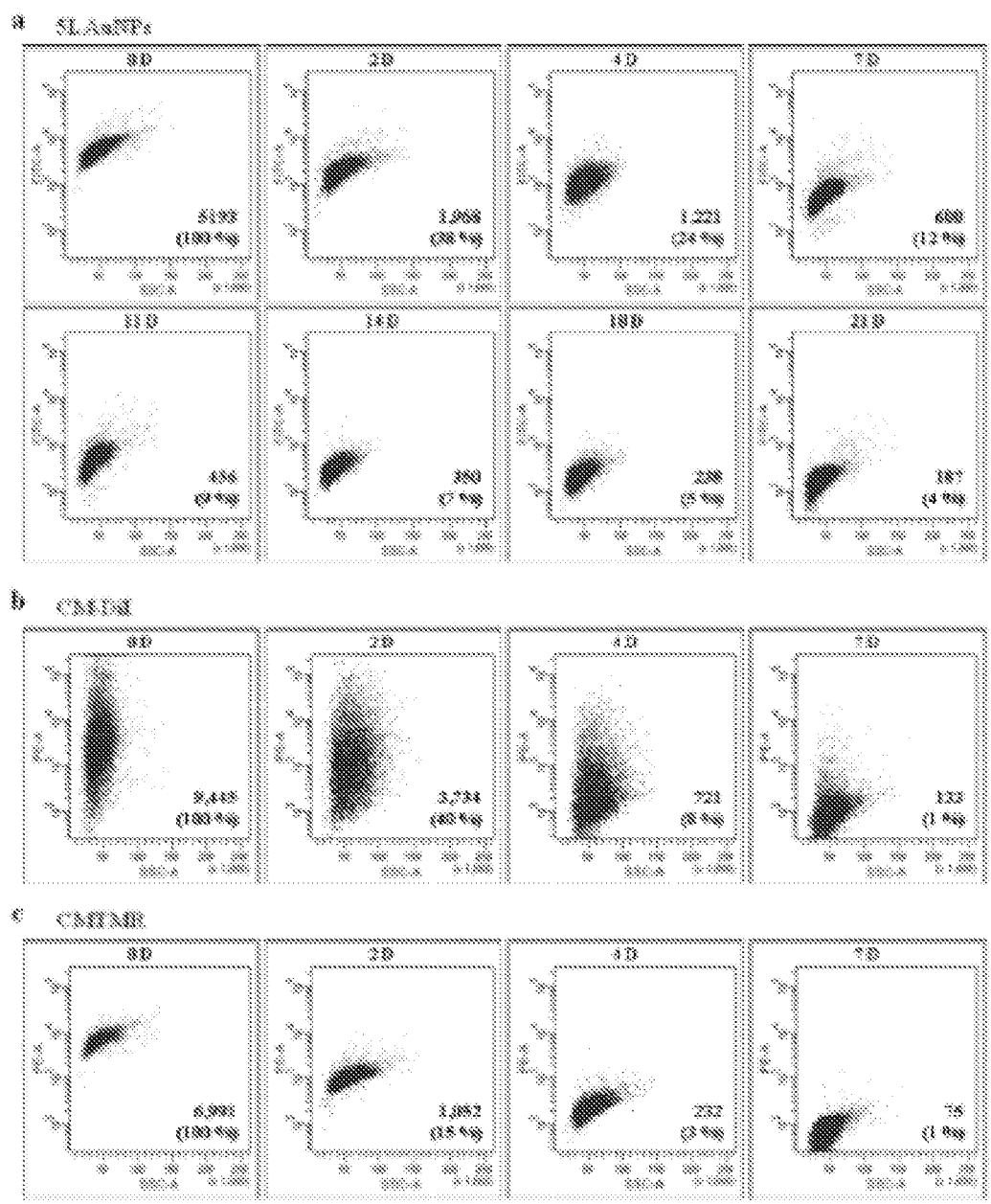

FIG. 29 shows cell population and fluorescence intensity of Jurkat cells. After treatment with 5L AuNPs (FIG. 29A), CM-DiI, 1 μM (FIG. 29B) or CMTMR, 2 μM (FIG. 29C) to Jurkat cells, fluorescence intensity was measured by flow cytometry with time course. Inserted number in each column shows the average fluorescence intensity value and the percentage, the intensity at 0 Day was set as 100%.

DETAILED DESCRIPTION

Provided herein are polypeptides that are selectively cleaved by cathepsin E. The polypeptides comprise a fluorescent donor moiety, an energy acceptor moiety, and an amino acid sequence comprising a Leucine-Proline, Serine-Leucine-X, or Leucine-X-Proline linkage at a scissile bond of the polypeptide, wherein X is any amino acid residue. The amino acid sequence comprising the Leucine-Proline, Serine-Leucine-X, or Leucine-X-Proline linkage is between the fluorescent donor moiety and the energy acceptor moiety. The scissile bond is selectively cleaved by cathepsin E, wherein cleavage of the scissile bond results in fluorescence.

Optionally, the fluorescent donor moiety is selected from the group consisting of a cyanine (Cy) fluorophore, IRD41, IRD700, NIR-1, LaJolla Blue, indocyanine green (ICG) and analogs thereof, indotricarbocyanine (ITC), AMC, pyropheophorbide-α, EDANS fluorophore, a chlorin, a porphyrin, rose bengal, porfimer sodium, and 7-methoxycoumarin-4-acetic acid (Mca). Examples of chlorins and porphyrins include bacteriochlorin, hematoporphyrin, chlorin e6, tetraphenylporphyrin, and benzoporphyrin. Fluorescent donor moieties are commercially available from corporations such as GE Healthcare (Piscataway, N.J.); Dyomics (Jena, Germany); Molecular Probes (Invitrogen; Carlsbad, Calif.); ATTO-TEC (Siegen, Germany); Visen (Bedford, Mass.); and Li-Cor (Lincoln, Nebr.) and are well known in the art.

Optionally, the energy acceptor moiety is selected from the group consisting of NIR fluorescence absorber (NIRQ820), a black hole quencher (BHQ), a blackberry quencher, A2-quencher, DABCYL quencher, IRD QC-1 quencher, a Cy quencher, and dinitrophenyl. Energy acceptor moieties are commercially available from corporations such as Biosearch (Novato, Calif.); Berry Associates (Dexter, Mich.); Li-Cor (Lincoln, Nebr.); and GE Healthcare (Piscataway, N.J.) and are well known in the art.

Optionally, the fluorescent donor moiety and energy acceptor moiety are the same moiety. By way of an example, the fluorescent donor moiety and energy acceptor moiety can be a Cy fluorophore. Prior to cleavage of the scissile bond, the fluorescent donor moiety and the energy acceptor moiety can be self-quenching. Cleavage of the scissile bond results in fluorescence.

The amino acid sequence of the polypeptide that is selectively cleaved by cathepsin E can, for example, comprise Ala-Gly-Phe-Ser-Leu-Pro-Ala-Lys-Arg (SEQ ID NO:1). Optionally, the amino acid sequence comprises Phe-Ser-Leu-Pro-Ala (SEQ ID NO:2) or Phe-Ser-Leu-X-Pro-Ala (SEQ ID NO:3). Optionally, the amino acid sequence comprises Ala-Gly-Phe-Ser-Leu-Gly-Pro-Lys-Arg (SEQ ID NO:4). The amino acid sequence can comprise, for example, SEQ ID NO:1 or SEQ ID NO:4 with up to 2 conservative amino acid substitutions.

The fluorescent donor moiety or energy acceptor moiety can, for example, be linked to the polypeptides in a range of 1-100 angstroms apart, which results in the quenching of the fluorescent donor moiety. Ranges for each fluorescent donor moiety and corresponding energy acceptor moiety are known in the art, as are basic methods involving Foerster resonance energy transfer (FRET), see, e.g., Gambin and Deniz, Mol. Biosyst. 6(9):1540-7 (2010); Roy et al., Nat. Methods 5(6): 507-16 (2008); and Joo et al., Annu Rev. Biochem. 77:51-76 (2008).

The fluorescent donor moiety or energy acceptor moiety can, for example, be linked to the polypeptides by a spacer polypeptide. Optionally, the spacer polypeptide is 5 to 10 amino acid residues in length. Optionally, the spacer polypeptide is 6 to 8 amino acid residues in length. The fluorescent donor moiety or the energy acceptor moiety can, for example, be covalently linked to the amino-terminal Ala residue of SEQ ID NO:1 or SEQ ID NO:4. The fluorescent donor moiety or the energy acceptor moiety can, for example be covalently linked to the Lys residue of SEQ ID NO:1 or SEQ ID NO:4. In instances where the fluorescent donor moiety is covalently linked to the amino-terminal Ala residue of SEQ ID NO:1 or SEQ ID NO:4, the energy acceptor moiety is covalently linked to the Lys residue of SEQ ID NO:1 or SEQ ID NO:4. In instances where the energy acceptor moiety is covalently linked to the amino terminal Ala residue of SEQ ID NO:1 or SEQ ID NO:4, the fluorescent donor moiety is covalently linked to the Lys residue of SEQ ID NO:1 or SEQ ID NO:4. Optionally, the Arg residue of SEQ ID NO:1 or SEQ ID NO:4 is in a D conformation.

The polypeptides described herein can be made using various techniques known to one of skill in the art. Optionally, the polypeptides can be chemically synthesized from individual amino acids that make up the final sequence of the polypeptide. Optionally, the polypeptides can be produced commercially by BACHEM (Torrance, Calif.), GenScript (Piscataway, N.J.), Sigma-Aldrich (St. Louis, Mo.), and Invitrogen (Carlsbad, Calif.).

By way of another example, nucleic acids that encode the provided polypeptides that are selectively cleaved by cathepsin E are disclosed, e.g., nucleic acid sequences that encode SEQ ID NO:1, SEQ ID NO:2, SEQ ID NO:3, or SEQ ID NO:4 are disclosed. These sequences include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequences.

As with all peptides, polypeptides, and proteins, including fragments thereof, it is understood that additional modifications in the amino acid sequence of the polypeptides that are selectively cleaved by cathepsin E can occur that do not alter the nature or function of the peptides, polypeptides, or proteins. Such modifications include conservative amino acids substitutions and are discussed in greater detail below.

The polypeptides provided herein have a desired function of being selectively cleaved by cathepsin E. The polypeptides are tested for their desired activity using the in vitro assays described herein.

The polypeptides described herein can be further modified and varied so long as the desired function is maintained. It is understood that one way to define any known modifications and derivatives or those that might arise, of the disclosed polypeptides herein is through defining the modifications and derivatives in terms of identity to specific known sequences. Specifically disclosed are polypeptides that have at least 75, 76, 77, 78, 79, 80, 81, 82, 83, 84, 85, 86, 87, 88, 89, 90, 91, 92, 93, 94, 95, 96, 97, 98, 99 percent identity to polypeptides that are selectively cleaved by cathepsin E provided herein. Those of skill in the art readily understand how to determine the identity of two polypeptides. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman, Adv. Appl. Math 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-10 (1989); Jaeger et al., Methods Enzymol. 183: 281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

Protein modifications include amino acid sequence modifications. Modifications in amino acid sequence may arise naturally as allelic variations (e.g., due to genetic polymorphism), may arise due to environmental influence (e.g., exposure to ultraviolet light), or may be produced by human intervention (e.g., by mutagenesis of cloned DNA sequences), such as induced point, deletion, insertion, and substitution mutants. These modifications can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue(s) inserted in its place. Such substitutions generally are made in accordance with the following Table 1 and are referred to as conservative substitutions.

TABLE 1

Amino Acid Substitutions

| Amino Acid | Substitutions (others are known in the art) |
| --- | --- |
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods. By way of example, modifications are made by site specific mutagenesis of nucleotides in the DNA encoding the polypeptide, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis. Optionally, the polypeptides can be synthesized to contain the desired modification. Artificial synthetic polypeptides are commercially available from such corporations as GenScript (Piscataway, N.J.), ChemPep® (Wellington, Fla.), or BaChem (Torrance, Calif.), and methods of synthesizing artificial polypeptides are known in the art.

Also provided are methods of detecting cathepsin E. The methods comprise contacting the cathepsin E with the polypeptides provided herein and detecting fluorescence. Detection of fluorescence indicates the presence of cathepsin E. Optionally, the contacting step is performed in vivo. Optionally, the contacting step is performed in vitro. Optionally, the cathepsin E is in a cell. The cell can, for example, be a cancer cell. Optionally, the cancer cell is selected from the group consisting of a pancreatic ductal adenocarcinoma cell, a cervical adenocarcinoma cell, a gastric adenocarcinoma cell, a prostate cancer cell, a colorectal cancer cell, a lung cancer cell, a breast cancer cell, an adenoendocrine carcinoma cell, and a neuroendocrine positive cancer cell.

Also provided are methods of diagnosing cancer in a subject. The methods comprise contacting a cell of the subject with the polypeptides provided herein and detecting an increase in fluorescence in the subject as compared to a control. The polypeptide can be administered systemically or locally. An increase in fluorescence caused by cleavage of the polypeptide by cathepsin E in the subject indicates the subject has cancer. Optionally, the contacting step is performed in vitro using a sample from the subject. Optionally, the contacting step is performed in vivo. Techniques for in vivo delivery of the polypeptides provided herein and measuring fluorescence in a subject are known in the art. See, for example, Choi et al. "Selective Antitumor Effect of Novel Protease-Mediated Photodynamic Agent," Cancer Research 66: 7225-7229 (2006).

Also provided are methods of detecting a pre-cancerous condition in a subject. The methods comprise contacting a cell of the subject with the polypeptides provided herein and detecting an increase in fluorescence in the subject as compared to a control. An increase in fluorescence caused by cleavage of the polypeptide by cathepsin E indicates the subject has a pre-cancerous condition. Optionally, the contacting step is performed in vitro using a sample from the subject. Optionally, the contacting step is performed in vivo. If performed in vivo, the polypeptide can be administered locally or systemically.

Further provided are methods for detecting the presence of a cancer or a pre-cancerous condition in a subject, wherein the subject has been treated previously for cancer, optionally, wherein the cancer was determined previously to be in remission. The methods comprise selecting a subject previously treated for cancer, contacting a cell of the subject with the polypeptides provided herein, and detecting an increase in fluorescence in the subject as compared to a control. An increase in fluorescence caused by the cleavage of the polypeptide by cathepsin E in the subject indicates that the subject has cancer or a pre-cancerous condition. The contacting step can be in vitro or in vivo, as described above. The subject previously treated for cancer could have been treated with chemotherapy, radiation therapy, surgery, etc. The subject may be clinically free of cancer.

The detecting step can comprise fluorescence microscopy and in vivo imaging methods like X-ray, MRI, and fluorescent imaging. Other techniques for diagnosing cancer via in vivo fluorescence imaging are known in the art. See, for example, Bourg et al., "A mouse model for monitoring calpain activity under physiological and pathological conditions," J. Biol. Chem. 22:281(51): 39672-80 (2006) and Kularatne et al., "Deep-tissue imaging of intramolecular fluorescence resonance energy-transfer parameters," Opt. Letters 35(9): 1314-6 (2010). Other techniques for in vivo diagnosis include, but are not limited to, MRI, optical coherence tomography (OCT) (see, for example, Lankenau et al. "Optical coherence tomography allows for the reliable identification of laryngeal epithelial dysplasia and for precise biopsy: a clinicopathological study of 61 patients undergoing microlaryngoscopy" Laryngoscope 120(10): 1964-70 (2010), and coherent anti-Stokes Raman scattering (CARS) endoscopy (see, for example, Evans et al. "Chemical imaging of tissue in vivo with video-rate coherent anti-Stokes Raman scattering microscopy," Proc. Natl. Acad. Sci. USA 102(46): 16807-12 (2005). One or more in vivo imaging techniques can be utilized to diagnose cancer in a subject. A sample can, for example, comprise cells or tissue isolated from the subject.

Also provided is a method of monitoring the effectiveness of a cancer treatment in a subject being treated for cancer. The method comprises contacting a cell of the subject at various time points with the polypeptides described herein and detecting a level of fluorescence. A decreasing level of fluorescence over the course of the cancer treatment indicates that the treatment is effective. A steady or increasing level of fluorescence over the course of the treatment indicates that the treatment is ineffective. The contacting step can be in vitro or in vivo, as described above. Cells can be within a sample, including a tumor biopsy or a biological fluid, like blood.

Optionally, the cancer or pre-cancerous condition are selected from the group consisting of a pancreatic ductal adenocarcinoma, a cervical adenocarcinoma, a gastric adenocarcinoma, a prostate cancer, a lung carcinoma, a breast cancer, an adenoendocrine carcinoma, a neuroendocrine positive tumor, and pre-cancerous conditions thereof.

As used herein, control refers to a nondiseased cell from the same subject or a different subject. Optionally, the level of fluorescence in the subject is compared to a known reference value or a nondiseased subject. The known reference value can, for example, be from the same subject at previous time points or it can be from a different, nondiseased subject. Those of skill in the art are capable of determining the appropriate controls for diagnosing cancer in a subject.

Also provided herein is a multilayered nanoparticle or a composition comprising the multilayered nanoparticle wherein the multilayered nanoparticle comprises a charged nanoparticle core or capsule coated with alternating positive and negative layers. Optionally, the positive layer comprises a positively charged protease degradable polypeptide. Optionally, the negative layer comprises a negatively charged therapeutic agent or a therapeutic agent and a means for providing the agent with a negative charge. For example, optionally, the therapeutic agent is linked to a negatively charged polymer.

Also provided are methods of treating or preventing a disease characterized by expression of a protease in a subject. The methods comprise administering to the subject a multilayered nanoparticle. The method optionally comprises identifying a subject with or at risk of developing a disease characterized by the expression of a protease. The multilayered nanoparticle used in the method comprises at least one layer of a therapeutic agent and at least one layer of a protease degradable polypeptide. Administration of the multilayered nanoparticle to the subject with or at risk of developing a disease characterized by the expression of a protease results in cleavage of the protease degradable polypeptide and release of the therapeutic agent, which treats or prevents the disease characterized by the expression of the protease.

Also provided is a method of localizing and/or treating or preventing a disease characterized by expression of a protease in a subject. The method comprises administering to the subject a multilayered nanoparticle. The multilayered nanoparticle can, for example, comprise at least one layer of a protease degradable detectable agent (e.g., a fluorescent agent) and at least one layer of a therapeutic agent or a spacing agent. The protease degradable detectable agent could be a specific polypeptide substrate (e.g., a polypeptide described herein)

loaded with multiple fluorochromes, such as Cy dyes, Alexa dyes, fluorescein dyes, rhodamine dyes, cyanine dyes and others. Detecting the presence of the detectable agent in the subject localizes the multilayered particle. Fluorescence is detected once the protease degradable polypeptide is cleaved releasing the fluorescent agent. Various imaging methods can be used to detect the fluorescent agent.

Optionally, the protease degradable polypeptide is positively charged and the therapeutic agent or spacing agent is negatively charged. Optionally, the protease degradable polypeptide is negatively charged and the therapeutic agent or spacing agent is positively charged.

Optionally, while the presence of the detectable agent localizes the disease characterized by the expression of a protease in the subject, the release of the detectable agent allows for the release of the therapeutic agent, thereby treating or preventing the disease in the subject.

Optionally, the protease is selected from the group consisting of cathepsins, matrix metalloproteinases, thrombin, and viral proteases. Optionally, the protease is selected from the group consisting of cathepsin B, cathepsin D, cathepsin E, cathepsin G, cathepsin L, cathepsin K, cathepsin S, caspase 1, DPP-IV, HIV protease, HSV protease, matrix metalloproteinase 2, matrix metalloproteinase 7, matrix metalloproteinase 9, and gelatinase.

Optionally, the disease characterized by the expression of the protease is selected from the group consisting of cancer, an apoptosis-related disease, thrombosis, atherosclerosis, arthritis, diabetes, HIV, HSV, HPV, atopic dermatitis, infectious diseases, Alzheimer's disease, Parkinson's disease, and cardiovascular disease. The cancer can, for example, be selected from the group consisting of pancreatic cancer, intestinal cancer, bladder cancer, colorectal cancer, liver cancer, cervical cancer, prostate cancer, brain cancer, ovarian cancer, lung cancer, breast cancer, head and neck cancer, lymphoma, leukemia, myeloma, and gastric cancer. One of skill in the art tests for expression of the protease by the target cells to determine if the disease is characterized by the expression of the protease. Accordingly, the nanoparticle is configured with a polypeptide degradable by a protease expressed by the target cells.

The charged nanoparticle core can, for example, be selected from the group consisting of a gold nanoparticle, a silicon nanoparticle, an iron oxide nanoparticle, a quantum dot, or a calcium carbonate core nanoparticle. Optionally, the charged nanoparticle core is removed after assembly of the multilayered nanoparticle to leave a capsule. Optionally, this capsule can comprise a therapeutic agent selected from the group consisting of an RNA, a DNA, an antisense molecule, a ribozyme, an siRNA, a shRNA molecule, an miRNA molecule, a drug, a protein, an aptamer, a small molecule, a peptide, an inorganic molecule, an organic molecule or an antibody The charged protease degradable polypeptide can comprise an amino acid sequence comprising a Leucine-Proline or a Leucine-X-Proline linkage at a scissile bond of the polypeptide, wherein X is an amino acid residue, and wherein the scissile bond is selectively cleaved by cathepsin E. Optionally, the protease degradable polypeptide comprises SEQ ID NO:1, SEQ ID NO:2, SEQ ID NO:3, or SEQ ID NO:4. The positively charged protease degradable polypeptide can, for example, be poly-L-lysine (PLL). By way of another example, the positively charged protease degradable polypeptide is polyethylenimine (PEI). Positively charged protease degradable polypeptides are known in the art, see, e.g., Weissleder et al., Nat. Biotechnol. 17(4):375-8 (1999); Tung et al., Canc. Res. 60:4953-8 (2000); Bremer et al., Nat. Med. 7(6):743-8 (2001); Tung et al., Chembiochem 3(2-3): 207-11 (2002); Shah et al., Canc. Res. 64(1):273-8 (2004); Funovics et al., Anal. Bioanal. Chem. 377(6):956-63 (2003).

The charged therapeutic agent can, for example, be selected from the group consisting of a nucleic acid molecule, a small molecule, and a polypeptide. Optionally, the nucleic acid molecule is selected from the group consisting of an siRNA molecule, a miRNA molecule, a shRNA molecule, an aptamer molecule, or an antisense molecule. The nucleic acid molecule can, for example, target an overexpressed mRNA molecule in the disease characterized by the expression of a protease. The mRNA molecule can, for example, be selected from the list consisting of VEGF, VEGFR1, RTP801, keratin 6a, p53, M2 subunit of ribonucleotide reductase (RRM2), immunoproteasome beta subunit LMP2, immunoproteasome beta subunit LMP7, immunoproteasome beta subunit MECL1, and HIV tat/rev. mRNAs overexpressed in diseases characterized by the expression of a protease are known in the art.

The negatively charged spacing agent can, for example, comprise an agent selected from the group consisting of polyacrylic acid, polylactic acid, dextran sulfate, heparin, polyglutamic acid, hyaluronic acid, and nucleic acids. The positively charged spacing agent can, for example, comprise an agent selected from the group consisting of chitosan, polylysine, polyarginine, polydiallyldimethylammonium, polyallylamine, polyvinylpyrrolidine, and polyethyleneimine, and poly(lysine-alanine).

Optionally, the multilayered nanoparticle comprises at least one layer of a therapeutic agent and at least one layer of a protease degradable polypeptide. The multilayered nanoparticle can, for example, comprise two, three, four, or five or more layers of the therapeutic agent and two, three, four, or five or more layers of the protease degradable polypeptide.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

As used throughout, a subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g., cancer). The term patient or subject includes human and veterinary subjects.

A subject at risk of developing a disease or disorder can be genetically predisposed to the disease or disorder, e.g., have a family history or have a mutation in a gene that causes the disease or disorder, or show early signs or symptoms of the disease or disorder. A subject currently with a disease or disorder has one or more than one symptom of the disease or disorder and may have been diagnosed with the disease or disorder.

The methods and agents as described herein are useful for both prophylactic and therapeutic treatment. For prophylactic use, a therapeutically effective amount of the agents described herein are administered to a subject prior to onset (e.g., before obvious signs of a disease characterized by expression of the protease) or during early onset (e.g., upon initial signs and symptoms of a disease characterized by expression of the protease). Prophylactic administration can occur for several days to years prior to the manifestation of symptoms of a disease characterized by expression of the protease. Prophylactic administration can be used, for example, in the preventative treatment of subjects diagnosed with a genetic predisposition to a disease characterized by expression of the protease. Therapeutic treatment involves administering to a subject a therapeutically effective amount of the agents described herein after diagnosis or development of a disease characterized by expression of the protease.

According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

Methods for delivering nanoparticles comprising therapeutic agents are known in the art. See, for example, Dass et al. "Nanoparticle-mediated interleukin-12 cancer gene therapy" J. Pharm. Sci. 13: 472-85 (2010) and Liu et al. "Nanomedicine for drug delivery and imaging: a promising avenue for cancer therapy and diagnosis using targeted functional nanoparticles," Int. J. Cancer. 120(12):2527-37 (2007). Methods for delivering nanoparticles comprising interfering RNAs, for example siRNA, are known also known in the art. See, for example, Davis et al. "Evidence of RNAi in humans from systemically administered siRNA via targeted nanoparticles" Nature 464:1067-1070 (2010) describes systemic administration of nanoparticles comprising siRNAs to produce specific gene inhibition in tumors. See also, Medarova et al. "In vivo imaging of siRNA delivery and silencing in tumors" Nature Medicine 13: 3720-377 (2007).

As used herein the terms treatment, treat, or treating refers to a method of reducing the effects of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

Methods of administration include, but are not limited to, mucosal, topical, intradermal, intrathecal, intratracheal, via nebulizer, via inhalation, intramuscular, intraperitoneal, vaginal, rectal, intravenous, subcutaneous, intranasal, and oral routes. Combinations of administration can also be utilized. For example, an agent can be delivered intranasally and intravenously to the subject. In another example, an agent can be administered orally and intravenously to the subject. Compounds can be administered by any convenient route, for example by infusion or bolus injection, by absorption through epithelial or mucocutaneous linings (for example, oral mucosa, rectal, vaginal and intestinal mucosa, etc.) and can be administered together with other biologically active agents. Administration can be systemic or local. Therapeutic agents can be delivered locally to the area in need of treatment, for example by topical application or local injection.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1

Selective Detection of Cathepsin E Enzymatic Activity

Materials.

All reagents used were of analytical or HPLC grade. Dicholormethane (DCM), N-methylpyrolidone (NMP) and methanol (MeOH) were purchased from Fisher (Fair Lawn, N.J.). N,N-dimethylformamide (DMF), diethylether, acetonitrile (MeCN), diisopropylethylamine (DIPEA), piperidine, pepstatin A, triisopropylsilane (TIS), 2,4,6-trinitrobenzenesulfonic acid (TNBS), triethylamine (TEA) and 1,2-ethanedithiol (EDT) were purchased from Sigma-Aldrich (Milwaukee, Wis.). HOBT and HBTU were purchased from Applied Biosystems (Foster City, Calif.). Fmoc protected amino acids were purchased from AnaSpec (Fremont, Calif.). Fmoc-Rink Amide MBHA resin, and Fmoc-Lys dinitrophenyl (Dnp)-OH were purchased from Novabiochem (La Jolla, Calif.). Cath E, Cath D, Cath S and Cath B were purchased from Calbiochem, EMD Bioscience (Gibbstown, N.J.). Anti-Cathepsin E antibody was purchased from R&D Systems (Minneapolis, Minn.).

Peptide Substrate Synthesis.

All peptide probes were synthesized by solid-phase peptide synthesis (SPPS) using the standard Fmoc chemistry on an automatic synthesizer (ABI-433A, Applied Biosystems). Rink amide MBHA resin, 100 µmol, with a substitution level of 0.7 µmol/mg was used as the support for peptide amide synthesis. Ten fold molar excess, relative to the resin loading, of each Fmoc protected amino acids was coupled sequentially to the resin using the HBTU/HOBT coupling strategy. Dnp group was attached to the ε-amino group of lysine side chain of all peptides during solid-phase synthesis using Fmoc-Lys (Dnp)-OH as the building block.

After completion of the peptide chain elongation, coumarin-based fluorophore, 7-Methoxycoumarin-4-acetic acid (Mca), was coupled to the N-terminal amino group via in situ activation. Three equivalents of Mca (300 µmol, 70.26 mg), relative to the resin loading, were dissolved in 9 mL NMP. HBTU (270 µmol, 102.39 mg) and HOBT (300 µmol, 39.45 mg) were dissolved in 2 mL DMF. These two solutions were mixed, and six equivalents (600 µmol, 103 µL) of DIPEA were added and vortexed thoroughly for 10-15 minutes. This solution was added directly to Rink amide MBHA resin bound peptide in a manual SPPS reaction vessel and agitated gently for 6 hours under N2 at room temperature in the dark. The reagents were drained and washed twice with NMP. The completion of Mca coupling was confirmed by TNBS assay. A small sample of peptidyl resin beads (~10 mg) was placed in a plastic filter tube to be colorimetrically tested for free —NH2 groups. The resin was washed with THF twice for 2 minutes. A few drops of 10% DIPEA in NMP were added, followed by 2 drops of TNBS. If the resin does not show reddish color, the coupling is considered complete.

Thereafter, all protecting groups were removed and the peptides were cleaved from the resin using a deprotection-scavenger cocktail (TFA:$H_2O$:TIS:EDT=94:2.5:1.0:2.5, 10 mL/g peptidyl resin) in a manual SPPS reaction vessel at room temperature in the dark with gentle agitation under $N_2$ for 3 hours. The cleavage cocktail containing peptide substrates were filtered and reduced in volume to ~1 mL. Cold diethyl ether was added to precipitate peptides. Crude peptides were redissolved in MeCN:$H_2O$ (50:50 v/v, ~6 mL) and purified by reversed phase high performance liquid chromatography (RP-HPLC) using a C18 preparative Column (Nova-Pak® HR, 6 µm, 60 Å, 19 mm ID×300 mm L; Waters, Milford, Mass.) with a linear gradient from 10% solvent B to 50% solvent B (8 mL/min) in 60 minutes on a Varian-ProStar 210 Chromatography system (Palo Alto, Calif.). HPLC solvent A is $H_2O$ containing 0.1% TFA, and solvent B is MeCN containing 0.1% TFA. Detection was carried out at 220 nm and 280 nm using a Varian-ProStar L-345 UV-V is detector (Varian; Palo Alto, Calif.). The purity of substrates was analyzed by analytical RP-HPLC using a C-18 column (5 µm, 4.6 mm ID×150 mm L Vydac, GRACE, Deerfield, Ill.) on a Varian 920-LC Liquid Chromatography system coupled to a UV-Vis/Fluorescence diodarray detector, and equipped with Galaxie Chromatography Data System™ (version 1.9) (Varian). Fractions with the same purity were collected together and lyophilized to yield orange-yellowish powders with greater than 97% purity. Purity represents the percentage of the area under the UV peak of interest to the total areas of all detected UV peak in the HPLC chromatogram.

HPLC showed the aspartic peptidase substrates a, b, c, d, and e with retention factors (k') of 7.01, 6.99, 7.03, 6.64, and 6.78, respectively. The molecular weight of the purified substrate and hydrolyzed fragments was confirmed by ESI-MS (Thermo Finnigan LCQ Fleet mass spectrometer, West Palm Beach, Fla., USA), and the raw data were analyzed using Xcalibur software. ESI-MS showed the molecular ions (m/z) of each aspartic peptidase substrate. The conjugate was stored at 4° C. in the dark.

Enzyme Cleavage and Substrate Specificity Assay.

The catalytic selectivity of Cath E and Cath D was determined fluorometrically by FRET-based hydrolysis of intramolecularly quenched peptide substrates a-e. Fluorogenic substrates a-e (10 µL, 200 µM) were incubated with 23 pmol of Cath E or Cath D in 50 mM sodium acetate buffer, pH 4, containing 150 mM NaCl, and the total volume was brought to 100 µL, using the same buffer. Cath S and Cath B were pre-activated by incubation with 100 mM sodium acetate buffer solution, pH 6.5, containing 5 mM DTT and 5 mM EDTA for 5 minutes. Cath S and Cath B (23 pmol) were incubated with 10 µL, of 200 µM fluorogenic substrate e at 100 mM sodium acetate buffer solution, pH6.5, containing 5 mM DTT and 5 mM EDTA, and the total volume was brought to 100 µL, using the same buffer. All assays were performed in triplicate in 96 well black walls, clear-bottom plates (Corning, N.Y.). The change in the fluorescence intensity was monitored over time using SpectraMax.$M2^e$ fluorescence spectrophotometer (Molecular Devices; Sunnyvale, Calif.) at excitation wavelength ($\lambda_{ex}$) of 340 nm and emission wavelength ($\lambda_{em}$) of 405 nm at 37° C. Control experiments were performed simultaneously by replacing the enzyme with assay buffer.

Enzyme Digestion and Fragments Characterization.

Substrate e was subjected to aspartic peptidase digestion using Cath E and Cath D. Fluorogenic substrate e (10 µL, 100 µM) was incubated at 37° C. for 3 hours with excess Cath E or Cath D (~119 pmol) in 100 µL, of 50 mM sodium acetate buffer (pH 4) containing 150 mM NaCl. The resulting digestion fragments were analyzed by the aforementioned analytical RP-HPLC and ESI-MS.

Enzyme Inhibition and Selective Immunoprecipitation of Cathepsin E.

Stock solution of pepstatin A was prepared by dissolving 2 mg pepstatin A in 1 mL of 10% (v/v) acetic acid in methanol. Substrate e solution (10 µL, 200 µM) in 50 mM sodium acetate buffer (pH 4) containing 150 mM NaCl, 46 pmol of Cathepsin E or D was added followed by 1 µL of 1 mM pepstatin A/methanol. Two sets of control experiments were performed simultaneously by replacing the enzymes with assay buffer and by using methanol instead of pepstatin A/methanol. All assays were performed in triplicate in 96 well assay plates and the change in the fluorescence intensity was monitored over time using $\lambda_{ex}$=340 nm and $\lambda_{em}$=405 nm at 37° C.

In a microcentrifuge tube, 5 µg Cath E enzyme was incubated with a specific Cath E antibody in 1:1 ratio using 500 µL, 1×PBS as an immunoprecipitation buffer. The mixture was gently mixed for 60 minutes at 4° C. Protein-G-sepharose was added and allowed to immobilize the specific Cath E antibody for 60 additional minutes on ice. The mixture was centrifuged at 3000 rpm for 2 minutes, and the supernatant was collected and used for the subsequent enzyme assay as described before.

Cathepsin E Dose Response.

The initial rates of substrate e hydrolysis by Cath E were monitored using a fluorescence plate-reader. Hydrolysis of different substrate e concentrations, 10, 20, 40 and 60 µM, was performed at pH 4 in 50 mM sodium acetate buffer containing 150 mM NaCl. Cath E with various concentrations, 2.27, 4.55, 6.82 nM, were incubated with substrate e and the changes in the fluorescence intensities were monitored for 10 minutes. The substrate e hydrolysis was determined by integrating the fluorescence intensity, and plotted by the amount of the hydrolyzed substrate e over time.

Kinetic Parameters of Substrate e.

The initial velocities of the hydrolysis reactions were measured between 0 and 10 minutes using several concentrations of substrate e including: 5, 10, 20, 40, 60, 80, 100 µM. All of the used substrate e concentrations were much higher than the concentrations of enzyme (2.3, 4.5 and 6.8 nM). To measure the initial rates of the substrate e proteolysis and to determine Michaelis-Menten kinetic parameters $V_{max}$ and $K_m$ of the Cath E and Cath D, the Michaelis-Menten equation was transformed using the Woolf kinetic transformation $[S/v=(S/V_{max})+(K_m/V_{max})]$. The initial velocity was calculated from the slope during the linear phase of the reaction and S/V plotted versus substrate e concentration. The graph representation gave straight lines and $V_{max}$ and $K_m$ were calculated by the linear regression of the line to obtain the slope and intercept. The turnover number of Cath E enzyme ($K_{cat}$) was calculated using the equation $K_{cat}=V_{max}/[\text{Cath E}]$, where [Cath E] represents the Cath E concentration in µM and Vmax is the maximum velocity in µM S-1. All the reactions and measurements were carried out in 50 mM sodium acetate buffers (pH 4.0) using the aforementioned setting.

Statistical Analysis.

Statistical Package for the Social Sciences (version 13, SPSS, Chicago, Ill.) was used for examining the null hypothesis and assessing the statistical significance of the observed fluorescence intensity differences. Paired-samples T-test with two-tailed P-values was employed with statistical significance attributed to P<0.05.

Substrate Design and Synthesis.

Proteases are usually highly specific with respect to substrates because of the structure of their active cleft (Dunn, Nat. Biotechnol. 18:149-50 (2000)). This specificity can be evidenced by the enzyme's ability to distinguish between very similar molecules. However, not all proteases are so specific. Cath E and Cath D accept numbers of closely related substrates if they possess some common structural features. The bulky hydrophobic phenylalanine amino acid residues at position P1 and P1' of the scissile bond have been described in the majority of reported substrates for both Cath E and Cath D (Yasuda et al., Biol. Chem. 386:299-305 (2005); Scarborough et al., Protein Sci. 2:264-76 (1993); Gulnik et al., FEBS Lett. 413:379-84 (1997); Yasuda et al., J. Biochem. 125:1137-43 (1999); Rao-Naik et al., Proteins 22:168-81 (1995)). Only few amino acid residues at P1 and P1' positions have been reported (Scarborough et al., Protein Sci. 2:264-76 (1993)).

The distinction of the catalytic activity of Cath E from that of Cath D is still problematic even with the large number of developed substrates. Lacking distinction between proteolytic activity of Cath E and Cath D might be in part due to the persistent usage of Phe as the common residue at the cleavage position (Yasuda et al., Biol. Chem. 386:299-305 (2005); Baechle et al., J. Pept. Sci. 11:166-74 (2005); Scarborough et al., Protein Sci. 2:264-76 (1993); Gulnik et al., FEBS Lett. 413:379-84 (1997); Yasuda et al., J. Biochem. 125:1137-43 (1999); Rao-Naik et al., Proteins 22:168-81 (1995)). It was hypothesized that using a hydrophobic amino acid residue other than Phe at the scissile bond and/or switching amino acids at P1 and P1' positions might lead to a better substrate that is capable of differentiating Cath E and Cath D.

A previously reported peptide substrate described as the most sensitive sequence (substrate a, Table 2) for Cath E was used as a reference (Yasuda et al., Biol. Chem. 386:299-305 (2005)). Substrates b and c, derived from the peptide substrate Gly-Lys-Pro-Ile-Leu-Phe-Phe-Arg-Leu-Lys (SEQ ID NO:16), previously described as sensitive substrate for Cath E and Cath D (Yasuda et al., J. Biochem. 125:1137-43 (1999); Rao-Naik et al., Proteins 22:168-81 (1995)), were also selected to compare sequence preference and examine the effect at P4' position. Gly residue was inserted at P4' position of substrate b based on the substrate sequence previously described as sensitive and specific for Cath D (Baechle et al., J. Pept. Sci. 11:166-74 (2005)). After examining the hydrophobicity of the P1 residue in the reported substrates, it is believed that a hydrophobic group is critical. According to the Kyte and Doolittle hydropathy scale, the hydrophobicity index of Leu is slightly higher (3.8) than that of Phe (2.8) (Kyte and Doolittle, J. Mol. Biol. 157:105-32 (1982)). Thus, Leu was selected as the hydrophobic amino acid residue at P1 position in substrates d and e. The effect of the P1' position was studied by using two conformationally distinctive amino acid residues. One is a conformationally unrestricted Gly residue and the other one is a rigid Pro residue. A charged D-Arg residue, which resists enzymatic hydrolysis, was placed at the C-termini of all substrates to increase solubility.

Due to significant spectral overlap between the emission spectrum of Mca and the absorbance spectrum of Dnp, they are widely used as a fluorophore and quencher pair. While the Mca-fluorophore moieties were attached to the N-terminal residues of the substrates, the Dnp quencher moieties were anchored to the ε-amino group of lysine residue's side chain after the prime scissile position. The characteristics of the prepared peptide probes were confirmed using ESI-MS (Table 2).

TABLE 2

List of developed peptide substrates and their characteristics.

| Sub. | Peptide Seq. P4 P3 P2 P1 ** P1' P2' P3' P4' | Calculated $[M + H]^+$ | Observed $[M + H]^+$ | Observed $[M + 2H]^{2+}/2$ |
|---|---|---|---|---|
| a | Mca-Gly-Ser-Pro-Ala-Phe**Leu-Ala-Lys(Dnp)-DArg-CONH$_2$ (SEQ ID NO: 5) | 1327.59 | 1327.56 | 664.39 |
| b | Mca-Gly-Pro-Ile-Leu-Phe**Phe-Arg-Leu-Gly-Lys(Dnp)-DArg-CONH$_2$ (SEQ ID NO: 6) | 1685.03 | 1685.06 | 843.56 |

TABLE 2-continued

List of developed peptide substrates and their characteristics.

| Sub. | Peptide Seq. P4 P3 P2 P1 ** P1' P2' P3' P4' | Calculated [M + H]$^+$ | Observed [M + H]$^+$ | Observed [M + 2H]$^{2+}$/2 |
|---|---|---|---|---|
| c | Mca-Gly-Pro-Ile-Leu-Phe**Phe-Arg-Leu-Lys(Dnp)-DArg-CONH$_2$ (SEQ ID NO: 7) | 1627.5 | 1627.91 | 814.97 |
| d | Mca-Ala-Gly-Phe-Ser-Leu**Gly-Pro-Lys(Dnp)-DArg-CONH$_2$ (SEQ ID NO: 4) | 1313.58 | 1313.70 | 657.52 |
| e | Mca-Ala-Gly-Phe-Ser-Leu**Pro-Ala-Lys(Dnp)-DArg-CONH$_2$ (SEQ ID NO: 1) | 1327.61 | 1327.62 | 664.55 |

Enzyme Cleavage Sensitivity and Substrate Specificity Assay.

Figure 1A:
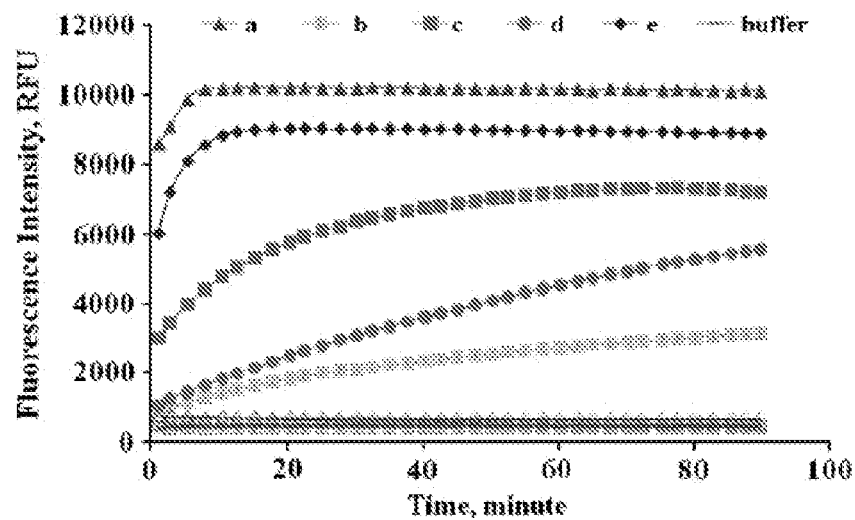
FIG. 1 shows changes in the fluorescence intensity of substrates a-e (200 μM) with 23 pmol of Cath E (FIG. 1A) and Cath D (FIG. 1B) in 50 mM NaOAc buffer containing 150 mM NaCl (pH 4.0). Solid filled and unfilled markers denote the enzyme treated and untreated substrates, respectively.
Figure 1B:
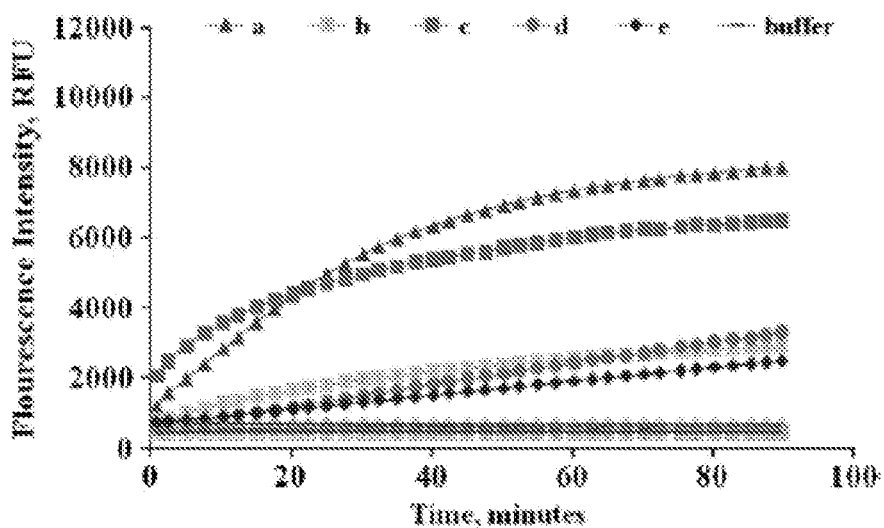

The protease mediated hydrolysis of the prepared fluorogenic substrates was followed by measuring changes in fluorescence intensity over time (FIG. 1). Without enzymes, substrates a-e showed and maintained an evident quenching over the monitored period, thus the fluorescence intensity of the substrates was comparable to that of buffer solution (FIGS. 1A and 1B).

A prominent fluorescence increase of substrate a was observed instantaneously upon incubation with Cath E (FIG. 1A). Substrate a showed the fastest increase and the highest fluorescence signal among all investigated substrates. Unfortunately, such leading increase in fluorescence signal with Cath E was observed as well upon incubation with Cath D (FIG. 1B). As seen with Cath E, the increase in fluorescence signals of substrate a upon incubation with Cath D was the highest among all investigated substrates. Phe-Leu at P1 and P1' positions in substrate a might allow constructive interaction with the binding sites of Cath D and Cath E.

Compared to substrate b, substrate c shows superior increase in the fluorescence intensity upon hydrolysis by both Cath E and Cath D (FIGS. 1A and 1B). Knowing that the scissile peptide bond of both substrates b and c shares the same sequence of amino acids except at the distant P4' position, points out to the significant role that P4' position might play in the substrate cleavage susceptibility. Although substrate b and c exhibit distinctive susceptibility to Cath E and Cath D, they could not distinguish their proteolytic activities effectively. Most likely, having Phe-Phe at P1 and P1' position of the scissile peptide bond could not offer preferred selectivity.

Substrates d and e differ only in the amino acid residues at P1' and P2' positions; nevertheless their proteolytic activation by Cath E was dramatically different (FIG. 1A). While substrate e was activated by Cath E quickly and reached saturation within 10 minutes, substrate d showed relatively slow hydrolysis and did not reach saturation within the monitored period. On the other hand, both substrates d and e exhibited similar slow hydrolysis by Cath D (FIG. 1B). It is conceivable that placing a conformationally restricted Pro residue at P1' position boosts the activation of the Cath E intermediate, whereas a Gly residue at the same position failed to demonstrate the same influence. While it was considered essential to have Phe in the substrate scissile bond to be susceptible by Cath E and Cath D in the literature (Yasuda et al., J. Biochem. 125:1137-43 (1999)), the results obtained from this study demonstrate that the susceptibility of -Leu-Pro- is critical to Cath E, but not to Cath D.

Substrate selectivity was represented by the number fold difference in fluorescence signal of Cath E over Cath D (FIG. 2). Substrate e showed a striking 265-fold higher fluorescent signal ratio upon incubation with Cath E at 1 minute (FIG. 2) and the ratio maintained high during the entire time period monitored. Comparatively, small differences were observed for substrates a and d, 17.9 and 12 fold, respectively, at the initial time point. The ratios continued to drop further to 4.5 and 4.0 fold at 10 minutes and to 1.6 and 2.3 fold, respectively, at the end of 45 minutes.

Although the peptide sequences of substrates d and e are similar except at the prime side of the scissile bond, P1' and P2' positions, the difference in their fluorescence signal ratio was instantly recognizable. Placing a residue with exceptional conformational restrain, such as Pro at P1' position of substrate e, has a constructive influence on the selectivity between Cath E and Cath D.

Negligible fluorescent signal ratios were observed for substrate b and c, 1.6 and 1.5 fold, respectively, immediately after incubation and remained low (FIG. 2). This insignificant fluorescence signal ratio implicates the failure of the sequences possessing Phe-Phe, substrate b and c, at their scissile peptide bond in distinguishing between Cath E and Cath D. These fluorescence signal ratio results demonstrated the superiority of substrate e over the other investigated substrates in distinguishing Cath E and Cath D.

To further confirm the confined cleavage specificity to Cath E, the peptide substrate e was subjected to hydrolysis using two additional major lysosomal cathepsins, Cath S and Cath B, believed to be involved in similar biological catalytic activities (FIG. 3A). As Cath E, upregulation and secretion of Cath B has been shown to occur in many types of tumors and to correlate positively with their invasive and metastatic capabilities by dissolving extracellular barriers (Nomura and Katunuma, J. Med. Invest. 52:1-9 (2005)). Both Cath E and Cath S, a major lysosomal cysteine proteinase mediating degradation of class II major histocompatibility complex (MHC) in antigen presenting cells, have been reported to be involved in formation of amyloid proteins (Zaidi et al., Biochem. Biophys. Res. Commun. 360:51-55 (2008); Nakanishi et al., J. Neurochem. 68:739-49 (1997)).

Similar to Cath D, limited increases in the fluorescence signal were observed by incubation of substrate e with Cath S or Cath B (FIG. 3B). The fluorescent signal increased less than 15% of that observed with Cath E in 90 minutes. Excessive increases in the fluorescence signal of substrate e were observed immediately upon incubation with Cath E. The fluorescence signal continued increasing fairly quickly at 30 minutes of incubation with Cath E. Statistical analysis using paired-samples T-test indicates that fluorescence differences are significant (two-tailed P-values of <0.001). These results verify the pronounced specificity of substrate e to Cath E.

Cleavage Site Identification.

To identify the exact scission site, substrate e was incubated with five times more Cath E at 37° C. for 3 hours. The incubation mixtures were analyzed by analytical HPLC (FIG. 4A) and the identity of the digestion substrate fragments were characterized by ESI-MS (FIG. 4B). The RP-HPLC chromatogram of the digested substrate e with Cath E showed only two major substrate fragments I and II (FIG. 4A). The fluorescence-HPLC chromatogram revealed a single fluorescent-peak overlaid with UV peak of substrate fragment I. Based on LC-MS analysis, peaks I and II resulting from Cath E digestion were corresponding to Mca-Ala$^1$-Gly$^2$-Phe$^3$-Ser$^4$-Leu$^5$-OH m/z 709.3 [M+H$^+$, 710.16] (SEQ ID NO:21), and -Pro$^6$-Ala$^7$-Lys(Dnp)$^8$-DArg$^9$-CONH$_2$ m/z 635.31 [M+H$^+$, 636.35] (SEQ ID NO:22), respectively. The LC-MS and fluorescence-HPLC results demonstrate that Cath E enzyme cleaves substrate e exclusively between Leu$^5$ and Pro$^6$.

When incubated with a high dose of Cath D for overnight hydrolysis, two minor cleavage sites were identified, one is between the P1 and P1' sites (-Leu$^5$-Pro$^6$-) and a secondary site was found between P3 and P4 positions (-Gly$^2$-Phe$^3$-).

Enzyme Inhibition and Selective Immunoprecipitation of Cath E.

To further confirm the specificity of the substrate e activation, the inhibition effect of aspartic peptidases on substrate e hydrolysis was tested. Pepstatin A was selected based on its specific universal inhibition capabilities for acid peptidases (Yasuda et al., Biol. Chem. 386:299-305 (2005); Zaidi et al., FEBS J. 274:3138-49 (2007); Kitamura et al., J. Mol. Biol. 387:1186-1198 (2009)). It forms a complex with almost all aspartic peptidases without inhibiting cysteine or serine proteases (Yasuda et al., Biol. Chem. 386:299-305 (2005); Zaidi et al., FEBS J. 274:3138-49 (2007); Yasuda et al., J. Biochem. 125:1137-43 (1999)), thus it would non-selectively inhibit the proteolytic activity of Cath E and D. In addition, selective inhibition of Cath E could be conducted using a specific anti-Cath E antibody, which recognizes both pro and mature Cath E with less than 1% cross-reactivity with Cath D according to the manufacturer data sheet. The antibody-Cath E complexes were pulled down by addition of antibody binding protein-G coupled insoluble matrix (sepharose beads). After centrifugation, the remaining supernatant was used for the enzyme specificity assay. The inhibition effect of pepstatin A and anti-Cath E antibody on substrate e hydrolysis by Cath E and Cath D was examined over the investigated time period (FIG. 5).

The complete inhibition of the fluorescence signal by pepstatin A confirms that the registered fluorescence signal of substrate e is solely due to the aspartic peptidase Cath E and/or Cath D (FIG. 5A). The specificity of the inhibition process was further confirmed by selective immunological precipitation of Cath E using a specific Cath E antibody. Complete absence of substrate e activation was observed after the selective immunoprecipitation of Cath E (FIG. 5B). The evident inhibition by the specific Cath E antibody substantiates that the observed increase in the fluorescence signal of substrate e is exclusively due to the catalytic activation by Cath E enzyme.

Enzyme Kinetics.

To quantify the kinetic constants of the Cath E enzyme, the proteolysis of substrate e was examined by incubating 10, 20, 40 and 60 μM of substrate e with 2.27, 4.55, 6.82 nM of Cath E for 10 minutes at 37° C. The change in the fluorescence intensity of each substrate e concentration was monitored over time using a fluorescence spectrophotometer at $\lambda_{ex}$=340 nm and $\lambda_{em}$=405 nm. Linear increases in the concentration of the fluorescently labeled digestion product were observed for all the investigated concentrations of substrate e and Cath E. Under the assay conditions, the linear phases of hydrolysis were maintained within the investigated time period between 0 and 10 minutes, even with the lowest concentration of substrate e (FIG. 6A). The observed linear increase in the rate of the hydrolysis with increasing substrate e concentrations implies that the catalysis rate of Cath E is directly proportional with the concentrations of substrate e within the monitored period.

To estimate Michaelis-Menten parameters ($V_{max}$ and $K_m$), the velocities of the hydrolysis at early time points were measured at different concentrations (10, 20, 40, 60, 80 and 100 μM) of substrate e. Initial rates of cleavage at varying concentrations of peptide substrate e were determined and values for Km and Kcat were calculated (Table 3). While the obtained $K_m$ value, 19.37 μM, indicates higher binding affinity of Cath E for the substrate e, the high $K_{cat}$ value, 322.5 S$^{-1}$, suggests a higher efficiency of Cath E in transforming substrate e to its hydrolyzed products. In contrast, no measurable cleavage was observed using up to 54 nM of Cath D under the same measurement condition.

TABLE 3

Kinetic parameters for hydrolysis of fluorogenic substrate e by Cath E. All reactions and measurements were carried out in 50 mM sodium acetate buffers (pH 4.0) for 10 minutes at 37° C. Fluorescent measurements were collected with 340 nm excitation and 405 nm emissions.

| | | | Woolf kinetic transformation | | | |
|---|---|---|---|---|---|---|
| Cath. Enzyme | Conc. (nM) | $R^2$ | $V_{max}$ (μM S$^{-1}$) | $K_m$ (μM) | $K_{cat}$ (S$^{-1}$) | $K_{cat}/K_m$ (mM$^{-1}$S$^{-1}$) |
| E | 6.8 | 0.96 | 2.2 | 19.37 | 322.5 | 16.7 |

Table 4 compiles the reported specificity constant ($K_{cat}/K_m$) of Cath E and Cath D using various substrates including peptide substrate e. The calculated specificity constant value of Cath E enzyme for substrate e, 16.7 μM$^{-1}$ S$^{-1}$, was comparable to those reported for other substrates (Table 4). The high $K_{cat}/K_m$ value reveals the high specificity of Cath E in binding and transforming substrate e. Although sequences 6 and 7 show a considerably high $K_{cat}/K_m$ value for Cath E, 10.9 and 12.2, respectively, they also exhibit high values for Cath D, 15.6 and 16.3, respectively. Sequences 6 and 7, thus, were not able to distinguish Cath E from Cath D. Sequence 2 and sequence 3 possess almost the same succession except at the P3 and P3' positions, however, their $K_{cat}/K_m$ values for Cath E were vastly different. The $K_{cat}/K_m$ value of sequence 3 for Cath E was around 16 fold higher than the value of sequence 2. Interestingly, their $K_{cat}/K_m$ values for Cath D were extremely close. The specificity constant of Cath E for substrate e represents one of the highest reported $K_{cat}/K_m$ values. This is not only a reflection of the efficacy of Cath E in binding substrate e, but it also displays the effectiveness of transforming the bound substrate e into hydrolyzed fragments. Importantly, no measurable cleavage was observed using the Cath D enzyme under the same reaction conditions.

TABLE 4

Specificity constant (Kcat/km) of Cath E for various substrates.

| | Substrate Sequence | | | | | | | | Catalytic Eff. $K_{cat}/K_m$ (mM$^{-1}$ S$^{-1}$) | |
|---|---|---|---|---|---|---|---|---|---|---|
| Seq. | P5 | P4 | P3 | P2 | P1 | *P1' | P2' | P3' | Cath E | Cath D |
| 1 (Sub. e) (SEQ ID NO: 1) | Ala | Gly | Phe | Ser | Leu | *Pro | Ala | Lys(Dnp) | 16.7 | NM$^a$ |
| 2 (SEQ ID NO: 8) | Gly | Ser | Ser | Ala | Phe | *Leu | Ala | Phe | 0.69 | 0.35 |
| 3 (Sub. a) (SEQ ID NO: 5) | Gly | Ser | Pro | Ala | Phe | *Leu | Ala | Lys | 11.2 | 0.92 |
| 4 (SEQ ID NO: 9) | Lys | Pro | Ile | Leu | Phe | *Phe | Arg | Leu | NR$^b$ | 0.03 |
| 5 (SEQ ID NO: 10) | Lys | Pro | Ile | Ser | Phe | *Phe | Arg | Leu | NR$^b$ | 0.14 |
| 6 (SEQ ID NO: 11) | Lys | Pro | Ile | Leu | Phe | *Phe | Arg | Leu | 10.9 | 15.6 |
| 7 (SEQ ID NO: 12) | Lys | Pro | Ile | Ile | Phe | *Phe | Arg | Leu | 12.2 | 16.3 |
| 8 (SEQ ID NO: 13) | Lys | Pro | Ile | Met | Phe | *Phe | Arg | Leu | NR$^b$ | 5.4 |
| 9 (SEQ ID NO: 14) | Lys | Pro | Ile | Leu | Phe | *Phe | Arg | Leu | NR$^b$ | 7 |
| 10 (SEQ ID NO: 15) | Lys | Pro | Ile | Cys | Phe | *Phe | Arg | Leu | NR$^b$ | 14.0 |

$^a$No measurable cleavage was observed using up to 54 nM of Cathepsin D under the same measurement condition.
$^b$Not reported.

Example 2

Detection of Pancreatic Cancer Tumors and Precursor Lesions by Cathepsin E

Pancreatic Tissues and Cell Lines.

Paraffin embedded tissue slides of human normal pancreas and pancreatic adenocarcinoma were obtained from the Department of Pathology, University of Texas, M. D. Anderson Cancer Center. Thirty-seven human paraffin samples (10 of normal pancreas, 12 with PanIN1, 22 with PanIN2, 9 with PanIN3 and 13 with invasive carcinoma) were used. A cell line derived from primary tumor grafts, MD Anderson Pancreatic Adenocarcinoma Tumor Cells-3 (MDA PATC-3) and an establish pancreatic cancer cell line (Mpanc96) (Peiper et al., Int. J. Cancer 71:993-9 (1997)) were used and grown in RPMI-1640 supplemented with 10% FBS, 1 mM sodium pyruvate, 2 mM L-glutamine, 1× non-essential amino acids (Gibco; Invitrogen; Carlsbad, Calif.), and 1× Pen/Strep (100 U/ml Penicillin, 100 ug/ml Streptomycin).

Analysis of Cath E mRNA Levels by Real-Time Polymerase Chain Reaction (RT-PCR).

Total RNA from normal pancreas, chronic pancreatitis and pancreatic adenocarcinoma tissues were prepared using Trizol reagent (Invitrogen; Carlsbad, Calif.) and further purified using RNeasy kit (Qiagen Inc.; Valencia, Calif.) with 15 minutes of DNase digestion. Reverse transcription was conducted using AMV Reverse Transcriptase kit as per the manufacturer's instructions (Promega; Madison, Wis.). Briefly, 1 μg of total RNA was denatured for 5 minutes at 70° C., cooled for 5 minutes on ice, then reverse transcriptase (RT) was added to a total volume of 20 μl, and reverse transcription was conducted for 60 minutes at 42° C. RT-PCR was performed on a thermal cycler (Bio-Rad, Hercules, Calif.) for 40 cycles (denaturation, 20 seconds at 95° C.; annealing and extension 1 minute at 60° C.) using specific primers for Cath E (NM_001910): forward primer TCACCTTCACCATTAACG-GAGTC (SEQ ID NO:23) and reverse primer GCATTC-CATCCACGAAGTCCA (SEQ ID NO:24) and a Taqman probe Hex-CCCTCAGCCCAACTGCCTACACCC-BHQ1 (SEQ ID NO:25). Primers for Ribosome protein S6 (NM_001010): forward primer AAGGAGAGAAGGATATT CCTGGAC (SEQ ID NO:26), reverse primer AAGGGCTTTCTTACAACATACTGG (SEQ ID NO:27)), and a Taqman probe (FAM-TGATACTACAGTGCCTCGC-CGCCT-BHQ-1 (SEQ ID NO:28)) were used as internal controls for each samples.

Immunohistochemical Localization of Cath E.

Unstained 4 μm sections of human clinical specimens and mouse tissues were deparaffinized with xylene and rehydrated with ethanol. Antigen retrieval was performed with DAKO antigen retrieval solution (Dako, Carpinteria, Calif.) using a microwave at 98° C. for 10 minutes. Endogenous peroxidase was blocked by hydrogen peroxide (3%) treatment for 10 minutes. For protein blocking 5% normal horse serum plus 1% normal goat serum in PBS was applied for 1 hour. Primary antibodies were incubated over night at 4° C. in blocking solutions. The following antibodies were used: Cath E (sc-6508, Santa Cruz Biotechnology, Santa Cruz, Calif.) (1:50 dilution for human specimens and 1:200 dilution for mouse specimens) and a biotinylated rabbit anti goat secondary (Vector Labs; Burlingame, Calif.) (1:100). Slides were then incubated with ready-to-use horseradish peroxidase streptavidin solution (Vector Labs) for 30 minutes. Finally, slides were developed with 3,3-diaminobenzidine substrate (Vector Labs) and counterstained with hematoxylin, washed and dehydrated with ethanol, fixed with xylene and mounted.

Cath E Probe Synthesis.

Cath E peptide substrate, Ala-Gly-Phe-Ser-Leu-Pro-Ala-Gly-CysCONH$_2$ (SEQ ID NO:29) prepared by standard solid phase synthesis was labeled with Cy5.5 (GE; Piscataway, N.J.) and then used for probe synthesis. Peptide loadings on the D-polyethylene glycol protected grafted copolymer (DPGC) were calculated using the relative mole ratio of the imaging probes to the DPGC. On average, each polymer carrier had ~23 of cy5.5 fluorochromes attached, and the probe showed ~95% of fluorescence quenching.

Animal Models.

To assess whether Cath E activity served as a biomarker for in vivo imaging, studies were performed in human pancreatic cancer xenografts in immunodeficient mice (acquired from the National Cancer Institute with age of the mice ranging from 5-6 weeks old) and transgenic mice. Animals were housed at the MD Anderson Cancer Center animal facility. Mice used for optical imaging studies were fed with a chlorophyll-free diet. Genetic PanINs and PDAC mouse models were developed by crossing cLGL-KRas$^{G12V}$ with Bac-Ela-CreER mice as described previously (Ji et al., Gastroenterology 137:1072-82 (2009)). These animals developed PanINs at 2 months and PDAC by ~6 months. In addition, LSL- KRas$^{G12D}$ mice (Jackson et al., Genes Dev. 15:3243-8 (2001)) were crossed with floxed p53 mice (Jonkers et al., Nat. Genet. 29:418-25 (2001)) and pancreatic specific cre (Pdx-1-Cre) mice (Hingorani et al., Cancer Cell 4:437-50 (2003)) to yield mice which possessed conditional p53 deletion and endogenous levels of mutant KRas$^{G12D}$ (Olive et al., Clin. Cancer. Res. 12:5277-87 (2006)). PDAC in these mice developed in 6-8 weeks after birth (Bardeesy et al., Proc. Natl. Acad. Sci. USA 103:5947-52 (2006)). Littermates without PDAC served as controls. LSL-KRas$^{G12D}$, p53 floxed, and Pdx-1-Cre genetic mice were obtained from the Mouse Models for Human Cancer Consortium Repository (Rockville, Md.).

For the immunohistochemical localization of Cath E in mouse tissues, 46 samples from genetically engineered mouse models (GEMMs) were used. These included 31 samples of the cLGL-KRas$^{G12V}$ with Bac-Ela-CreER mice (27 contained PanIN1, 14 contained PanIN2, 6 contained PanIN3 and 5 contained invasive carcinoma) and 5 of the p53 conditional deletion/LSL-Kras$^{G12D}$/Pdx1-Cre Mice, which all contained invasive carcinoma. Ten normal litter control mice were also included, 5 per genetic strain.

Human cancer specimens used for transplantation as primary tumor grafts were obtained from patients with pancreatic invasive ductal adenocarcinoma who had undergone initial surgical resection at UT MD Anderson Cancer Center (Kim et al., Nat. Protoc. 4:1670-80 (2009)). Nude mice were anesthetized with a single intraperitoneal injection of ketamine (100 mg/kg) and xylazine (10 mg/kg). After washing with sterile PBS, tumor fragments were placed in the subcutaneous space of immunodeficient mice (Kim et al., Nat. Protoc. 4:1670-80 (2009)). When the tumor was visible, it was dissected out and transplanted into male nude mice and allowed to grow for 30 days. Then, the Cath E-activatable fluorescent probe was injected and mice were imaged 48 hours after injection. At the end of the experiment, tumor tissue was excised, imaged, sectioned and stained with hematoxylin and eosin (H&E) stain.

To establish orthotopic tumors, mice were anesthetized as described above, and the pancreas was exposed through a left abdominal incision (laparotomy). Subconfluent MDA PATC-3 cells were detached with 0.25% trypsin-EDTA and cell viability was assessed by trypan blue exclusion. Cells (1×10$^6$) were resuspended in 50 uL of Hanks Balanced Salt Solution (HBSS) and directly injected into the pancreas (caudal). After tumor implantation, the pancreas was carefully returned to the peritoneal cavity and the abdomen was closed. Two months after tumor implantation, fluorescent probe was injected via tail vein and imaged 48 hours after injection.

In Vivo and Ex Vivo Imaging.

Subcutaneous models (human material PDAC tumor grafts with mice bearing 2 tumors each n=4, MDA PATC-3 orthotopic model n=3, MPanc96 expressing low levels of Cath E (MPanc96-FG30) n=10, and MPanc96 expression high levels of Cath E (Mpanc96-Cath E) n=10) and two transgenic models with litter controls (n=5 each) were used to assess the usefulness of the Cath E-activatable imaging probe. Animals were injected with a single dose of the optical imaging probe (1 nmol/100 µl PBS) or saline (controls) intravenously through tail vein using a 30 gauge syringe needle. The anesthetized mice were placed in the heated imaging platform of IVIS-100/Spectrum optical imaging systems (Xenogen/Caliper, Mountain View, Calif.). White light and near infrared fluorescence (NIRF) images were acquired sequentially using Cy5.5 fluorescence filters (615-665 nm excitation filter and 695-770 nm emission filter). Mice were imaged 48 hours post probe intravenous injection. Mice were sacrificed and organs/tissues were excised and rinsed with PBS then imaged for their associated NIRF. Fluorescence variations between different organs/tissues were corrected by subtracting the autofluorescence signals obtained from imaging organs/tissues of mice without any probe injected. General illumination setting and image acquisition parameters were: epi-illumination; 0.5 sec. exposure time; f/stop=2; binning (HR)4; field of view (FOV=12.9 cm or 6.5 cm width and height). The mean fluorescence flux from each image was defined as photons per second per centimeter squared per steradian (p/s/cm$^2$/sr). Acquired images were analyzed using Living Image 3.1 software (Xenogen/Caliper, Alameda, Calif.). Fluorescence contrast, defined as radiance, was quantified using identical size regions of interest (ROI).

Statistical Analysis.

Statistically significant differences were determined by two-tailed unpaired Student's t-test (P<0.05 was taken as significant) with Graph Pad Prism 5 software (GraphPad Software, La Jolla, Calif.).

Cath E is Highly Upregulated in Human and Mouse PDAC and PanINs.

The specificity of Cath E expression in human and animal GEMMs PDAC samples, including the different stages of PanIN lesions, was assessed. For this purpose, levels of Cath E mRNA were compared in human samples of normal pancreas, chronic pancreatitis (a benign inflammatory disease of the pancreas) and PDAC using quantitative real-time PCR (n=5 each; FIG. 15A). Cath E expression was confirmed to be up-regulated in PDAC ~117 fold when compared to normal pancreas (p=0.0072) and ~22 fold increase when compared to chronic pancreatitis (p=0.0089), therefore, confirming its specificity for PDAC. To verify the cell type expressing Cath E, human and mouse tissues were next examined by immunohistochemistry. Cath E was observed to be absent in normal pancreas of both human and GEMMs (FIGS. 15B and 15C). In contrast, Cath E expression was found to be highly upregulated in PanIN lesions (FIGS. 15D-15I and Table 5) and PDAC (FIGS. 15J and 15K and Table 5) in both humans and GEMMs.

TABLE 5

Percentage of animals containing different grade PanINs and tumors that were positive for Cath E expression

|  | Normal | PanIN1 | PanIN2 | PanIN3 | PDAC |
| --- | --- | --- | --- | --- | --- |
| Human | 0/10 (0%) | 12/19 (63%) | 22/22 (100%) | 9/10 (90%) | 12/14 (93%) |
| Mouse | 0/10 (0%) | 27/27 (100%) | 14/14 (100%) | 6/6 (100%) | 10/10 (100%) |

PDAC in Xenografts and Genetic Mouse Models can be Selectively Detected by Cath E Activity.

The potential usefulness of detecting PDAC by measuring Cath E activity using a Cath E-activatable imaging probe was determined. This Cath E-activatable imaging probe was able to detect Cath E activity in lysates from PDAC cells engineered to express Cath E enzyme at different levels (FIG.

Figure 18A:
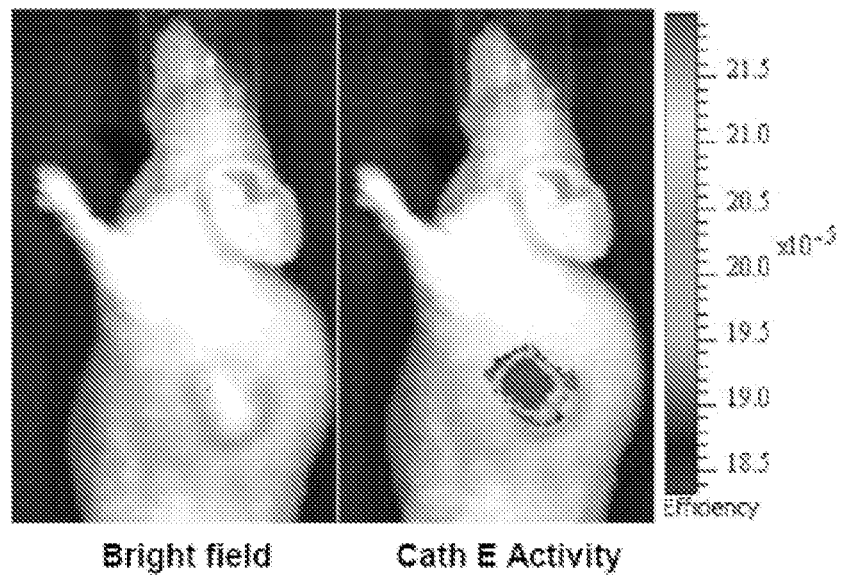
Figure 18B:
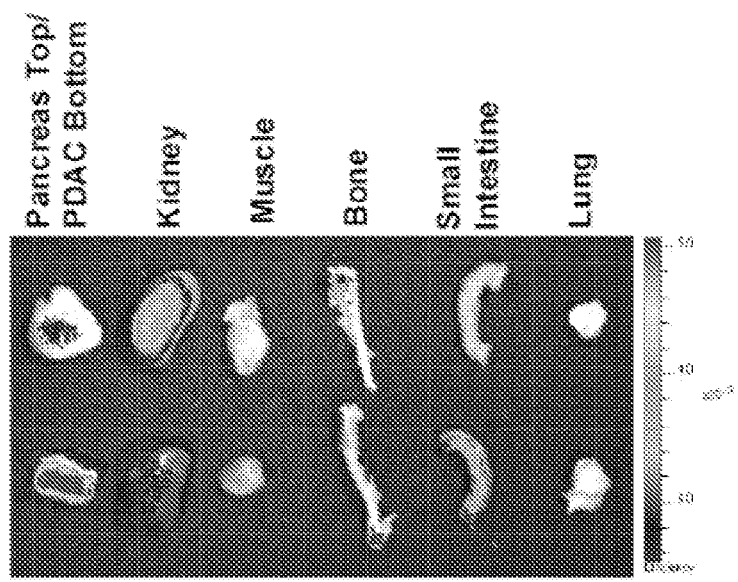
Figure 18C:
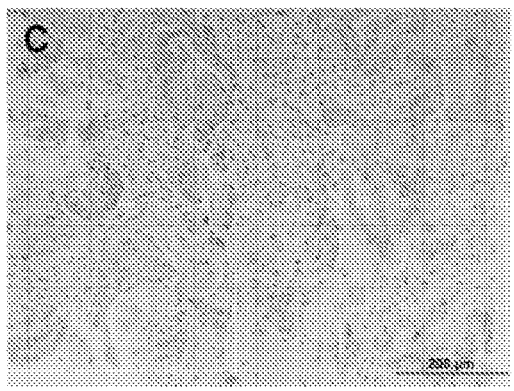
Figure 18D:
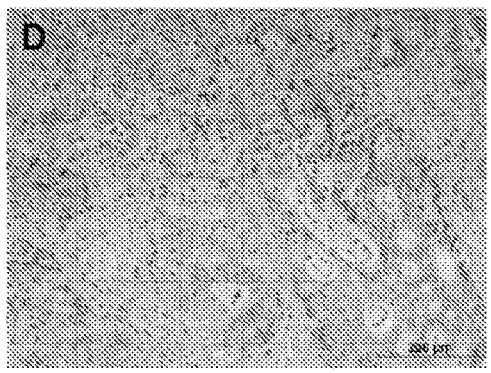
Figure 18E:
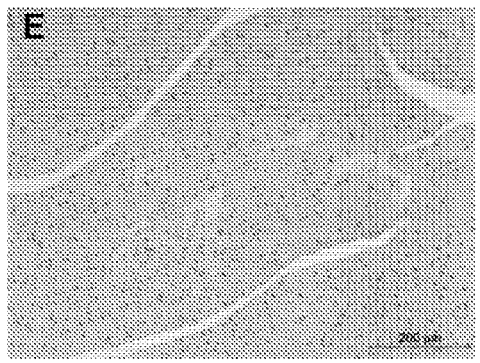
Figure 18F:
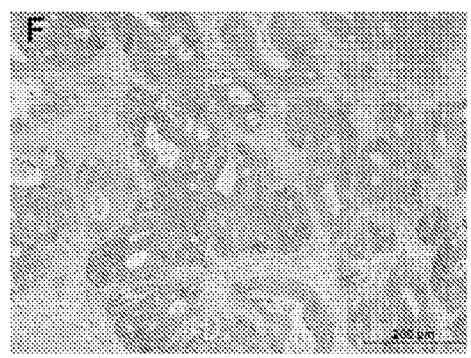

16A) and the signal correlated with the Cath E expression in vitro (FIGS. 16B-16D) and in vivo (FIG. 17). Therefore, the Cath E-activatable imaging probe was tested in various clinically relevant animal tumor models. Initially, tumors were formed in immunodeficient mice by subcutaneous transplantation of PDAC tumor material from a patient (tumor graft). The animals were then injected IV with the Cath E-activatable imaging probe. Animals injected with the probe, but not uninjected animals, developed a strong specific fluorescence signal localized to the implanted tumor grafts after 48 hours (n=4; FIG. 18A). Next, primary pancreatic cancer cells isolated from patient tumor grafts were injected orthotopically into the pancreas of immunodeficient mice. The Cath E-activatable imaging probe was then administered to these animals with orthotopic human primary cells from tumor grafts. Organs were excised and examined ectopically (n=3; FIG. 18B). A strong signal specifically localized to the tumors in the pancreas was observed. These human primary tumor cell models developed a prominent stroma similar to that in the tumor grafts (FIGS. 18C and 18D) or observed in human PDAC. High Cath E expression was seen in the tumors localized specifically to the cancer cells (FIG. 18F) and no Cath E expression was seen in the normal pancreas (FIG. 18E).

To verify the results in an autochthonous model of PDAC, tumors developed in well-established GEMMs were also imaged. It was found that the Cath E activity sensitive probe readily enabled the imaging of PDAC tumors from both GEMMs models used (n=5 each) (FIG. 19, top and middle panel, and 20; signal increased ~15 fold, p=0.0002) and also a tumor metastasis in the lung (FIG. 19, bottom panel) in these models. The characteristics of the GEMMs PDAC tumors were confirmed by histology and Cath E expression was assessed (FIGS. 19D-19G), which confirmed that the cancer cells are the source of the Cath E expression in the tissues imaged. Outside the pancreas, signals were limited except for the liver (FIG. 20), probably due to high non-specific enzymatic activity. To directly examine the relative signals, different tissues were subjected to side by side imaging comparisons and quantitative fluorescence signal analysis (FIG. 20D). The tumor to non-tumor signal ratios were as followed, tumor/normal pancreas 2.2, tumor/kidney 1.9, tumor/muscle 5.5, tumor/bone 2.6, tumor/small intestine 1.7, tumor/lung 2.9, tumor/spleen 3.9, which clearly suggest tumor specificity of the probe.

Pancreas with PanIN Lesions can be Detected Using Cath E Activity.

Figure 21A:
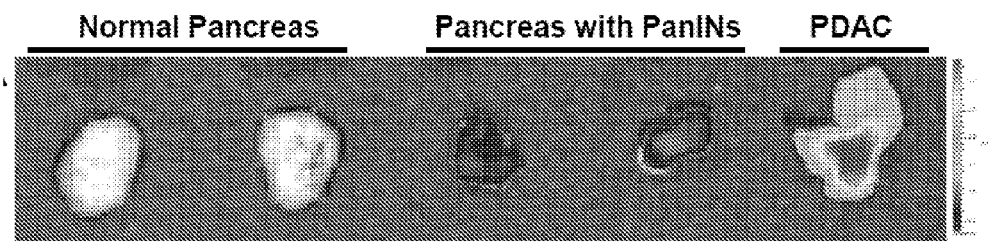
Figure 21B:
Figure 21C:
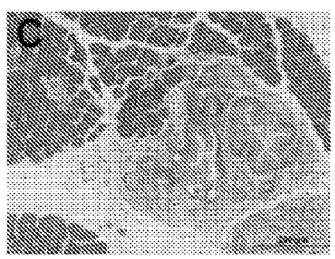
Figure 21D:
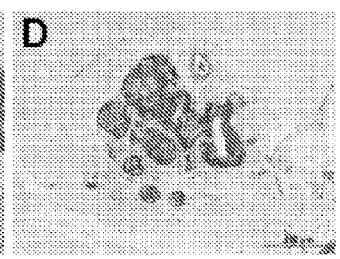
Figure 21E:
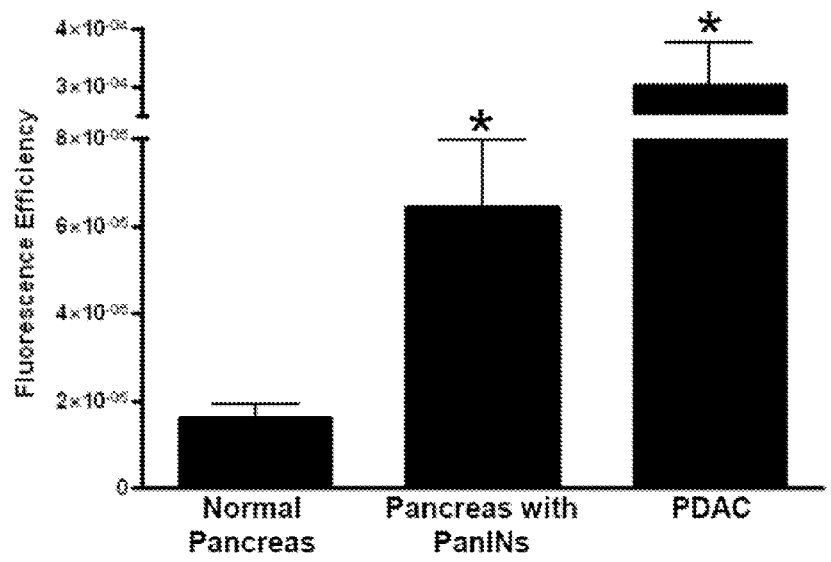

Histological immunohistochemical analysis showed high Cath E expression in human and mouse PanIN lesions (FIGS. 15D-15I). Therefore, whether the Cath E-activatable imaging probe could detect pancreas with precancerous lesions was determined. For this purpose, a transgenic pancreatic cancer mouse model that forms abundant PanINs at early times and then progresses to invasive and metastatic disease over several months was used (Ji et al., Gastroenterology 137:1072-82 (2009); Hingorani et al., Cancer Cell 4:437-50 (2003)). Mice were injected with the Cath E-activatable imaging probe at times during which only PanINs (2 months), but no tumors, were present (cLGL-KRas$^{G12V}$ with Bac-Ela-CreER mice). Cath E probe generated a strong specific signal (~3 fold, p=0.0058) in the pancreas of these mice bearing PanIN lesions when compare to normal pancreas (n=5; FIGS. 21A and 21E), and this signal was significantly lower than that of PDAC tumors (FIGS. 21A and 21E). The presence of PanIN lesions and lack of tumors was verified by histological analysis (FIG. 21C) and Cath E expression of the pancreas containing PanIN was confirmed to be specifically in the PanIN lesions (FIG. 21D). Pancreas containing PanINs and tumors from both GEMMs gave similar results and the data was pooled for both models in the quantitative analysis of fluorescence of (FIG. 21E).

Example 3

Multilayer sRAuNPs

Chemicals and Materials.

All siRNA and poly-L-lysine (Mw=15,000-30,000 g mol$^{-1}$) were obtained from Sigma-Aldrich (St. Louis, Mo.). Bare AuNPs (40 nm) were purchased from BB International (Cardiff, UK), Lipofectamine 2000 was from Invitrogen (Carlsbad, Calif.), D-Luciferin was from Regis Technologies (Morton Grove, Ill.) and MTT solution was from Promega (Madison, Wis.).

Preparation and Characterization of Multilayer sRAuNPs.

Using layer by layer (LbL) method, multiple layers of siRNA and PLL were successfully deposited on an Au surface. The sequences of siRNA against luciferase are sense strand: 5'-CGUACGCGGAAUACUUCGAdTdT-3' (SEQ ID NO:17), antisense strand: 5' UCGAAGUAUUC-CGCGUACGdTdT-3' (SEQ ID NO:18), and of control nonsense siRNA are sense strand: 5'-AGCUUCAUAAGGCG-CAUGCdTdT-3' (SEQ ID NO:19) and antisense strand: 5'-GCAUGCGCCUUAUGAAGCUdTdT-3' (SEQ ID NO:20) (Elbashir et al., Nature 411:494 (2001)). For cellular uptake experiments, a fluorochrome cyanine dye, cy5, was tagged on the 5' end of the sense siRNA. Au solution (3.15× 10$^9$ particles in 0.7 mL) was added dropwise onto a PLL solution (0.5 mL of 5 mg mL$^{-1}$) in pure water. After incubating for 30 minutes in the dark with gentle shaking, the solution was centrifuged for 30 minutes at 16,100 g using a microcentrifuge (Eppendorf, Hauppauge, N.Y.). The supernatant was removed, and the gel-like deep red pellet was re-suspended with pure water and centrifuged for 30 minutes at 16,100 g. After one more wash, PLL coated AuNPs were stored in pure water. Next a polyelectrolyte layer was deposited by adding PLL coated AuNPs (in 0.5 mL pure water) to siRNA solution (4.0 μM, 0.5 mL). The reaction solution was incubated in the dark for 30 minutes with gentle shaking, followed by three washes. The deposition procedures were repeated to have a total of 7 layers of polyelectrolytes (4 layers of PLL and 3 layers of siRNA). Sizes and zeta potentials of AuNPs in water were measured by Zetasizer Nano-ZS (Malvern, Worcestershire, UK) according to the manufacturer's instruction.

Transmission Electron Micrographs (TEM) Images.

Size of AuNPs was measured by TEM using JEOL 2010 FasTEM (JEOL Ltd., Tokyo, Japan). In brief, all samples were prepared by placing a drop of the NPs solution onto a carbon coated copper TEM grid (Ted Pella Inc., Redding, Calif.) of mesh size 300. After 5 minutes, the excess amount of the solution was removed using blotting paper. Negative staining of the sample was performed with one drop of Nano-W® (methylamine tungstate, Nanoprobes, Yaphank, N.Y.) for 45 seconds. The excess reagent was blotted away and the grids were allowed to dry overnight before the microscopy was performed. TEM measurements were operated at an accelerating voltage of 200 KV with a LaB6 filament.

Protease Assisted siRNA Release.

To measure the release of siRNA from sRAuNPs, formulated particles (1.26×10$^8$ particles) were incubated in a 96-well culture plate at 37° C. with or without 50 μL trypsin-EDTA (0.25%, Sigma-Aldrich) in phosphate buffered saline (PBS). After incubation, the concentration of siRNA in supernatant (1.5 μL) was determined by ND-1000 spectrophotometer (NanoDrop, Wilmington, Del.) at different time points. The protease-induced fluorescent change of siRNA was determined by incubating the sR1(cy5)P AuNPs ($1.26 \times 10^8$ particles) in a 96-well culture plate with or without trypsin (50 µL) in RPMI 1640 medium (Thermo Scientific, Rockford, Ill.) containing serum (Sigma-Aldrich) at 37° C. and the increase of cy5 fluorescence signal was analyzed by spectramax M2 plate reader (Molecular Devices, Sunnyvale, Calif.) with a 649 nm excitation and a 670 nm emission for 24 hours.

Cell Lines.

The human breast cancer cell line stably expressing firefly luciferase (MDA-MB231-luc2) and the human prostate cancer cell line stably expressing firefly luciferase (LNCaP-luc2) were purchased from Caliper (Alameda, Calif.). MDA-MB231-luc2 cell line were cultured in minimum essential medium (Invitrogen, Carlsbad, Calif.), while LNCaP-luc2 cell line were cultured in RPMI 1640 medium (Thermo Scientific) and both cell lines were supplemented with 2 mM L-glutamine, 100 U mL$^{-1}$ penicillin, 100 mg mL$^{-1}$ streptomycin, and 10% heat-inactivated fetal bovine serum (Sigma-Aldrich) in a humidified atmosphere of 5% $CO_2$ at 37° C.

Cellular Uptake of sRAuNPs.

MDA-MB231-luc2 cells ($5.0 \times 10^4$) and LNCaP-luc2 ($2.5 \times 10^5$) cells were seeded on a 35 mm culture dish with a glass bottomed microwell (Met-Tek Inc, Clackamas, Oreg.). After 24 hr or 48 hr, the culture medium was replaced with fresh sR1(cy5)P AuNPs ($1.58 \times 10^9$ particles) containing medium, and further cultured for 8 hours. Cells were then washed twice with PBS and cultured in the phenol red free medium. Real time fluorescent images of cells were acquired by a LCV-110 incubator fluorescence microscopy (Olympus Corporation; Tokyo, Japan). For flow cytometry analysis, MDA-MB231-luc2 cells ($5.0 \times 10^4$) and LNCaP-luc2 cells ($2.5 \times 10^5$) were seeded on 6-well culture plate (BD Falcon; San Jose, Calif.) and cultured for 24 or 48 hours. sR1(cy5)P AuNPs ($1.58 \times 10^9$ particles) were added and further cultured for 24 hours. After removal of the cultured medium, the cells were washed with PBS and then detached from the wells by trypsin-EDTA. After three more washes with PBS in tube, the cy5 fluorescence signal inside of cells indicating the uptake of siRNA were measured by BD FACSAria III flow cytometry (BD Biosciences; San Jose, Calif.).

Cytotoxicity Measurement of sRAuNPs.

MTT assay was performed to determine the cytotoxicity of Lipofectamine 2000 (Invitrogen) and the preparations of sRAuNPs. Briefly, MDA-MB231-luc2 cells were collected by trypsinization, counted, and plated in a 96-well culture plate at a density of $5 \times 10^3$ (or $2.5 \times 10^4$ of LNCaP-luc2) cells per well. One day later, sRAuNPs ($1.26 \times 10^8$ particles) and Lipofectamine 2000 (0.2 µL) were added and the cells were further cultured for 24 hours. MTT solutions (20 µL, Promega) were then added to each well. After incubation for an additional 3 hours, absorbance was measured at 570 nm using a SpectraMax plate reader (Molecular Devices).

Gene Silencing in MDA-MB231-luc2 and LNCaP-luc2 Cell Lines.

For the examination of the gene silencing effect, bioluminescence measurement was performed after incubating with various multilayered AuNPs. Cells were seeded in a 96-well black clear bottom culture plate at a density of $2.5 \times 10^3$ (or $1.25 \times 10^4$ of LNCaP-luc2) cells per well. One day later, different sRAuNP ($1.26 \times 10^8$ particles) were added to each well and cultured for another 24 hours. The cells were further cultured in phenol red free medium for another 5 days. Manufacturer's direction was followed for the transfection with Lipofectamine. Bioluminescence measurement was performed using IVIS 200 (Caliper) immediately after addition of 125 µg mL$^{-1}$ of D-Luciferin (Regis).

Effective Gene Silencing by Multilayered siRNA Coated Gold Nanoparticles.

FIG. 7 shows the preparation flow of multiple layered siRNA gold nanoparticles (sRAuNPs). It is known that the solubility of the coated AuNPs is largely affected by size and surface charges. The concentration and molecular weight of polycations and siRNA all have been optimized to prevent aggregation (Song et al., Small 6:239 (2010); Elbarky et al., Nano Lett. 9:2059 (2009)). Using an optimized procedure, densely packed sRAuNPs were obtained. To assemble the multiple layered sRAuNPs, the negatively charged gold particles in water were dropped into the positive charged PLL solution (average Mw: 22.5 KDa) for the first layer of coating. The reaction solution was incubated for 30 minutes, and then the coated particles were spun down by centrifuge. After several washes with sterilized water, the PLL coated AuNPs were added to the negatively charged siRNA (21 bp against luciferase) solution. After incubation, free unbound siRNAs were removed by centrifugation and the particles were re-suspended in sterilized water. As shown in FIG. 7, by repeating these procedures, multiple layers—total 4 layers of PLL and 3 layers of siRNA—were successfully deposited on Au surface by electrostatic interaction.

Transmission electron micrographs (TEM) images of bare AuNPs (40 nm) and polyelectrolyte coated AuNPs were collected (FIG. 8A). The visualization of the polyelectrolyte layers was achieved after negative staining with methylamine tungstate. Under TEM, all coated particles (sR1P, sR2P, and sR3P) were found about 50 nm in diameter. For comparison, the hydrodynamic diameter of the formulated particles was also measured by dynamic light scattering (DLS) after each layer of coating. The size of initial bare AuNPs was 40 nm, while the particle size increased steadily with the number of layers (sR1: 104 nm/sR1P: 151 nm/sR2P: 159 nm/sR3P: 183 nm). The differences between DLS and TEM might be caused by the hydrodynamic structure of sRAuNPs. The initial zeta potential of bare AuNPs was −42 mV. The PLL loading brought up the surface charge to about +46 mV, while the subsequent siRNA layer dragged it down to about −30 mV again. This characteristic zigzag pattern of zeta potential indicated the successful layering of the alternatively charged molecules (FIG. 8B).

The next critical step was to confirm that the fabricated siRNA could be released from sRAuNPs by proteases. PLL is made of a natural amino acid, lysine, so that it can be degraded by many different types of proteases, including lysosomal cathepsin B, and trypsin. Enzyme assisted release of siRNA was determined by incubating various sRAuNPs with trypsin in buffer, and fractions of the solution were collected at different time points to determine the concentration of released siRNA. As expected, the release kinetic of siRNA from sRAuNPs depended on the number of layers (sR1P>sR2P>sR3P) (FIG. 9A). It took about 3 days for siRNA to be fully released from the sR1P particles which had one layer of siRNA and two layers of PLL under the testing condition; whereas, it required 4 and 5 days for sR2P which had 2 siRNA/3 PLL and sR3P which had 3 siRNA/4 PLL, respectively. The data also validated the hypothesis that more siRNA could be carried on a single particle by multiple layering. The final siRNA concentration released from sRANPs for sR1P, sR2P and sR3P are 0.3, 0.7 and 1.1 µM, respectively. Similar results were observed in serum condition using sR1(cy5)P which were coated with cyanine dye, cy5, tagged siRNA. As shown in FIG. 9B, the fluorescence intensity of cy5 increased persistently because of the trypsin assisted release, and, importantly, the particle remained stable without trypsin, indicating no siRNA was released from the particle during the experimental period.

Figure 10A:
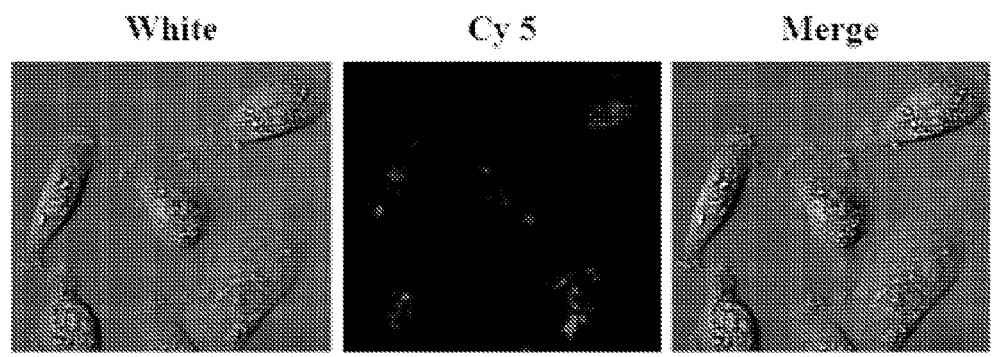
Figure 10B:
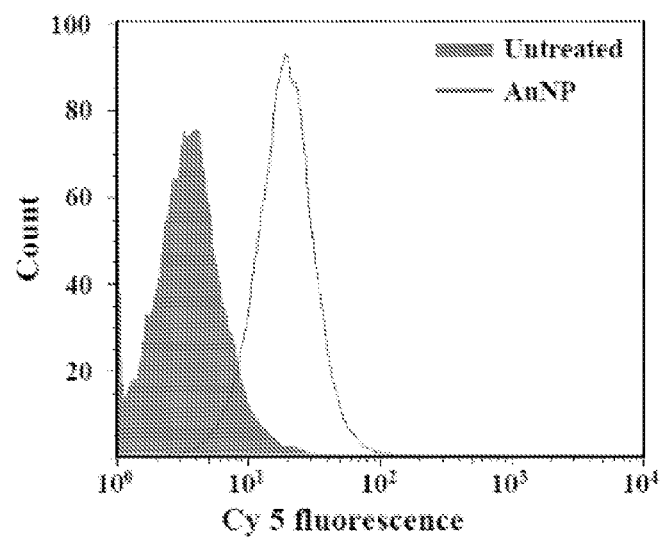
Figure 10C:
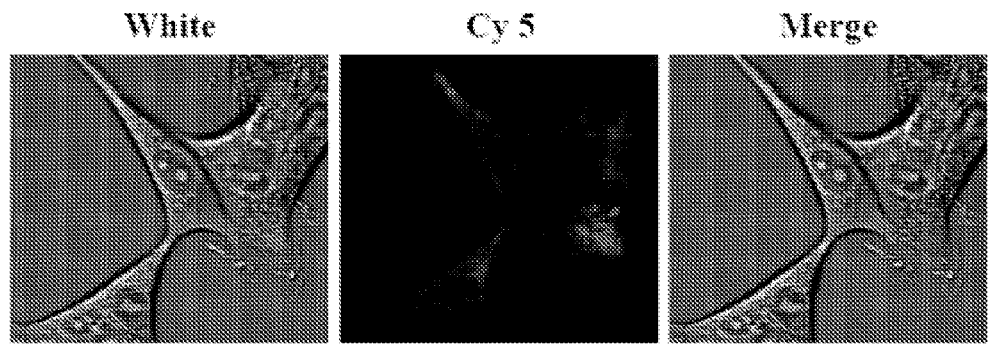
Figure 10D:
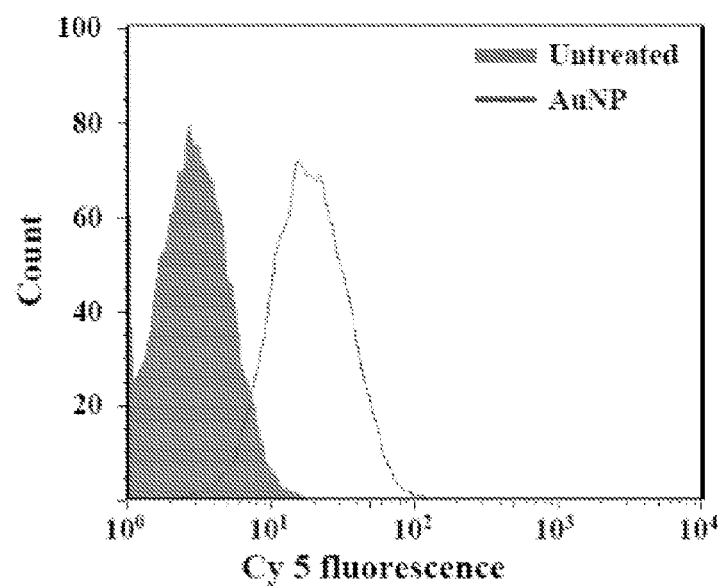

The ability of sRAuNPs to enter cells was investigated by real time fluorescence microscopy and flow cytometry. MDA-MB231-luc2 (FIG. 10A) and LNCaP-luc2 (FIG. 10C) cell lines were incubated with sR1(cy5)P AuNPs ($1.58 \times 10^9$ particles) for 8 hours. Since cy5 label was anchored to the siRNA, the fluorescence images reveal the location of the siRNA. Punctate fluorescence signal was seen in the early time points, while the signal was diffused into the cytoplasm as time progressed (FIGS. 10A and 10C). Cellular uptake of sRAuNPs by both cell lines was also confirmed by flow cytometry analysis. Strong cy5 fluorescent signal was obtained 24 hours after incubating with sR1(cy5)P AuNPs (FIGS. 10B and 10D). These cellular uptake data indicated that sRAuNPs require no transfection agent to enter cells, and, once it is internalized, the siRNA can be freed from particles slowly.

It has been reported that the toxicity of the formulated AuNPs depends on the chemical composition of the surface molecules, and high molecular weight polycationic carriers in non-viral vector delivery system could be toxic (Kunath et al., J. Control Release 89:113 (2003); Giljohann et al., Angew. Chem. Int. Ed. 49:3280 (2010); Read et al., Nucleic Acids Res. 33:e86 (2005)). Therefore the cytotoxicity of the prepared sRAuNPs was evaluated in MDA-MB231-luc2 and LNCaP-luc2 cell lines by comparing it with Lipofectamine 2000, which is a widely used transfection agent. As shown in FIG. 11, no significant toxicity was detected for all sRAuNPs, while some toxicity was observed with Lipofectamine 2000 in both cell lines (cell viability: less than 80%).

Finally the siRNA gene silencing effect was investigated by measuring the luciferase activity. MDA-MB231-luc2 cells stably expressing firefly luciferase were incubated with sR1P, sR2P, sR3P, siRNA/Lipofectamine, or free siRNA (FIG. 12). In addition, a control sR3P was prepared with a nonsense siRNA. After incubation with different sRAuNPs for 5 days, the luminescence of MDA-MB231-luc2 cells was measured immediately after addition of luciferin. It was found that the luminescence was reduced to about 43% by sR1P (siRNA 0.3 µM: $1.26 \times 10^8$ particles). Furthermore, the luciferase silencing effects was dependent on the number of siRNA layers. With the same amount of particles ($1.26 \times 10^8$), the luminescence intensity was down to 28% by sR2P (siRNA 0.7 µM), and to 18% by sR3P (siRNA 1.1 µM). No significant silencing effect was observed, when the luciferase siRNA in sR3P was replaced by a nonsense control siRNA. In comparison, the Lipofectamine formulation maintained 62% of luminescence, even though the siRNA concentration had been doubled (2.2 µM). Free unformulated siRNA (2.2 µM) didn't show any appreciable effect under the same conditions, either. Similar results were observed with LNCaP-luc2 cell lines. All results suggested that the three layered siRNA coated (sR3P) AuNPs was the best formulation in gene silencing (>80%) among all the different kinds of siRNA delivery formulations.

The positive charge has made the assembly straightforward, and also assisted the cellular delivery. It is known that positively charged NPs are most effective in crossing negatively charged cell membrane and localizing in the cytosol or nucleus (Verma and Stellacci, Small 6:12 (2010); Arvizo et al., Nano Lett. 10:2543 (2010); Cho et al., Nano Lett. 9:1080 (2009)). Due to the slow release of siRNA, excellent silencing effect was achieved even 5 or 6 days after single sRAuNPs treatment. Previously, the importance of biodegradable polymers for the improvement of siRNA release has been recognized (Elbakry et al., Nano Lett. 9:2059 (2009)). PLL was degraded slowly inside of cell, resulting in a persistent siRNA effect. In addition, the multilayered sRAuNPs carried more siRNA into cell and silenced the target gene more effectively than the monolayer sRAuNPs.

LbL technology had previously been reported; however, as a method it was not popular in siRNA delivery. A monolayered siRNA particle formulated with PEI has been prepared for siRNA delivery, and a thin film-based multilayered siRNA was prepared with PEI for electroporation purpose (Elbakry et al., Nano Lett. 9:2059 (2009); Fujimoto et al., Anal. Bioanal. Chem. 397:571 (2010)). Most recently PLL layered with siRNA has been applied to a thin film and albumin NPs (Zhang et al., Biomaterials 31:6013 (2010); Singh et al., Acta Biomater. 6:4277 (2010)). In contrast, the design presented above is a particle based multilayered sRAuNPs design which could have great impact in siRNA therapy. These results show that a multilayered sRAuNPs system is a much more effective system than a monolayered system. Furthermore, two or three different siRNAs which target different genes can be conveniently formulated on a single multilayered sRAuNPs, achieving a synergistic gene silencing effect. Dual silencing of target siRNA has been reported to be more effective than a single siRNA silencing (Tai et al., Mol. Pharm. 7:543 (2010); Kumar et al., 134:577 (2008)).

Example 4

Comparison of One or Two Types of siRNA Coated AuNPs

Using the multilayered siRNA coating technique, one or two different types of siRNA were successfully deposited on a PLL coated Au surface. Two siRNA sequences, Seq 1 (Elbashir et al., Nat. 411:494 (2001)) and Seq 2 (Chang et al., Nat. Meth. 3:707 (2006)), targeting luciferase were adopted from the literature. Single layer siRNA coated AuNPs, sR1P luc (Seq 1) or sR1P luc (Seq 2), were formed by sequential coating of Seq 1 (or Seq 2) siRNA and PLL onto the PLL coated Au surface. Multi-layer siRNA coated AuNPs with Seq 1 and Seq 2, sR2P luc (Seq 1+Seq 2), were fabricated by sequential coating of Seq 1 siRNA, PLL, Seq 2 siRNA and PLL onto the PLL coated Au surface.

To examine the gene silencing effect, bioluminescence measurement was performed by incubating with various multilayered AuNPs. Cells were seeded in a 96-well black wall clear bottom culture plate at a density of $1.25 \times 10^4$ of LNCaP-luc2 cells per well. One day later, different sRAuNP ($1.26 \times 10^8$ particles) were added to each well and cultured for additional 5 days. A bioluminescence measurement was performed using IVIS 200 (Caliper) immediately after addition of 125 mg mL$^{-1}$ of D-Luciferin (FIG. 13).

Example 5

Cathepsin B Protease Degradable Polypeptide

A variety of proteases are involved in the degradation of the extracellular matrix and basement membranes and therefore are key factors in the progression of cancers (30). Some types of cathepsins, a class of lysosomal proteases, are among the most related ones (Berdowska, Clin. Chim. Acta 342(1-2): 41-69 (2004)). Cathepsin B, for example, correlates with invasiveness and metastatic capabilities in many tumors (Frosch et al., Apmis 107(1):28-37 (1999)). Expression of cathepsin B in high-grade dysplasia and adenomas has been previously documented (Khan et al., Mod. Pathol. 11(8):

704-8 (1998), Campo et al., Am. J. Pathol. 145(2):301-9 (1994), Marten et al., Gastroenterology 122(2):406-14 (2002)).

Since cathepsin B is known to be over-expressed in various tumors and cathepsin B recognizes lysine and arginine peptide substrates, a polylysine imaging probe has been developed (Weissleder et al., Nat. Biotechnol. 17(4):375-8 (1999)). The poly-L-lysine (PLL) backbone is sterically protected by multiple methoxy-polyethyleneglycol (PEG) side chains. Each polymer backbone contains an average of 92 PEG molecules, and the overall molecular weight is about 450,000 Daltons (Da). The free lysine residues on the partially modified backbone are attached to multiple near-infrared (NIR) fluorochromes whose fluorescence signal is negligible in the non-activated state because of energy resonance transfer between fluorochromes (Tung et al., Bioconjug. Chem. 10(5): 892-6 (1999)). The probes are thus not detectable during in vivo circulation, and only become fluorescent after proteolytic activation.

The protease selectivity of this polylysine based imaging probe was evaluated with a panel of common human proteases found in the area of tumors. All enzymatic assays were performed in triplicate at pH 4.5 (50 mM Sodium acetate, 1 mM dithiothreitol) to simulate the pH environment of endosomal or lysosomal compartments, a primary residence for cathepsins. Matrix metalloproteinases (MMPs) were additionally tested at physiological pH (PBS buffer, pH 7.4, 1 mM dithiothreitol). In vitro assays demonstrated substantial activation of the probe by the cysteine proteases cathepsin B and L, but not by the other tested cysteine proteases, K and S (FIG. 14). Negligible NIR fluorescence (NIRF) signal amplification was produced by the aspartic proteases cathepsin D, G, or MMPs 2 and 9. The screening suggests that the synthesized probe is suitable to be degraded by cathepsin B and L activity in vivo.

Example 6

In Vivo Gene Silencing by Multilayered siRNA Coated Nanoparticles Comprising Polypeptides that are Selectively Cleaved by Cathepsin E Using the multilayered siRNA coating technique, one or more types of siRNA are deposited on an Au surface coated with a polypeptide that is selectively cleaved by cathepsin E. For example, the polypeptide can be selected from the group consisting of SEQ ID NO:1, SEQ ID NO: 2, SEQ ID NO: 3 and SEQ ID NO: 4. The siRNA can be any siRNA targeted to an mRNA that is overexpressed in tumor cells or otherwise desirable as a therapeutic target. For example, the siRNA can be targeted against p53 mRNA, VEGF mRNA, or any other mRNA of interest. The nanoparticles are delivered to the subject via methods described in the art (see, for example, Davis et al. "Evidence of RNAi in humans from systemically administered siRNA via targeted nanoparticles" Nature 464: 1067-1070 (2010), which describes systemic administration of nanoparticles comprising siRNAs to produce specific gene inhibition in tumors. See also, Medarova et al. "In vivo imaging of siRNA delivery and silencing in tumors" Nature Medicine 13: 3720-377 (2007)). To evaluate the inhibitory effects of the siRNA, total RNA can be extracted from the tumor and the amount of mRNA for the target mRNA of interest is measured via RT-PCR to measure a decrease in mRNA expression affected by the siRNA. One of skill in the art can obtain tissue sections from the tumor and measure the amount of protein, for example, with a labeled antibody, in order to determine if the siRNA resulted in decrease protein expression. Combinations of mRNA and protein quantitation can be performed. These examples are by no means limiting as one of skill in the art would know that there are numerous methods for measuring mRNA and protein expression that can be utilized in the methods described herein.

Example 7

Layered Nanoprobe for Long-Lasting Fluorescent Cell Label

Methods

Chemicals and Materials.

Poly-L-lysine ($M_w$=30,000~70,000), poly-D-lysine ($M_w$=30,000~70,000), poly acrylic acid (35 wt. % solution, average $M_w$=15,000), fluorescein 5(6)-isothiocyanate (FITC), and the monoclonal anti-CD3-PE antibody were obtained from Sigma-Aldrich (St. Louis, Mo.). Bare AuNPs (40 nm) were purchased from BB International (Cardiff, UK). SYTOX Blue, CM-DiI, and CMTMR were from Invitrogen (Carlsbad, Calif.). Amicon Ultracel membranes (10 kDa) were from Millipore (Billerica, Mass.), and CellTiter aqueous one solution was from Promega (Madison, Wis.).

Preparation of PLL-FITC and PDL-FITC.

Different amounts of FITC (0.1, 0.2, 0.4, 0.6, 0.8, or 1.0 mg) in dimethylformamide (DMF) solution (500 µl) were reacted with 1 mg PLL or PDL in NaHCO$_3$ (1 mM, 500 µl) with constant shaking in the dark at room temperature for 2 hours. The reaction products were separated using molecular weight cut-off membrane filters (10 kDa, Millipore). The resulting PLL-FITC and PDL-FITC was collected and washed several times with sterilized water until the color was clear.

Proteolytic Activation of PLL-FITC.

To measure the dequenching effect, the prepared PLL-FITC (PLL 0.2 nmole in 5 µl) and PDL-FITC (PDL 0.2 nmole in 5 µl) in PBS were incubated with 10 µl trypsin-EDTA (0.25%, Sigma-Aldrich) in a 96-well culture plate at 37° C., and the increase in the FITC fluorescence signal was assessed using a Spectramax M2 plate reader (Molecular Devices, Sunnyvale, Calif.) at 480 nm excitation and 530 nm emission for 3 hours.

Preparation of Multilayered Fluorescent AuNPs.

AuNP solution (40 nm, 3.15×10$^9$ particles in 700 µl) was added drop-wise into a PLL-FITC solution (PLL, 1.8 nmole in 500 µl). After incubating for 30 minutes in the dark with gentle shaking, the solution was centrifuged (30 minutes at 16,100 g, using a microcentrifuge; Eppendorf, Hauppauge, N.Y.). The supernatant was removed, and the gel-like deep red pellet was suspended in pure water and centrifuged again (30 minutes at 16,100 g). After a further wash, PLL-FITC-coated AuNPs were resuspended in pure water (500 µl). Next, the PLL-FITC-coated AuNPs were added to a PAA solution (23.3 mM, 500 µl). The reaction solution was incubated in the dark for 30 minutes with gentle shaking, followed by three washes. The deposition procedures were repeated to a total of nine layers of polyelectrolyte (five layers of PLL-FITC and four layers of PAA). Zeta potentials of prepared AuNPs in water were measured using a ZetaPALS (Brookhaven Instruments Corp., Holtsville, N.Y.) and sizes were measured using a Zetasizer Nano-ZS (Malvern, Worcestershire, UK) according to the manufacturer's protocol.

Protease-Assisted Fluorescence Release from Multilayered AuNPs.

The protease-induced fluorescence change of the multilayered fluorescent AuNPs was determined by incubating various formulated particles (7.88×10$^8$ particles) in a 96-well culture plate with or without trypsin (25 µl) in PBS at 37° C. and the increase in the FITC fluorescence signal was analyzed using a Spectramax M2 plate reader (Molecular Devices) at 480 nm excitation and 530 nm emission for 8 hours.

Cell Lines.

HeLa cells and MDA-MB231 human breast cancer cells were cultured in DMEM medium (Mediatech Inc., Manassas, Va.), and Jurkat cells were cultured in RPMI 1640 medium (Thermo Scientific, Rockford, Ill.). All culture media were supplemented with 2 mM L-glutamine, 100 U/ml penicillin, 100 mg/ml streptomycin, and 10% heat-inactivated fetal bovine serum (Sigma-Aldrich) in a humidified atmosphere with 5% $CO_2$ at 37° C.

Live Cell Imaging Using Fluorescence Microscopy.

Fluorescence images of live cells were acquired using a fluorescence microscopy system (Olympus, Tokyo, Japan). Briefly, HeLa and MDA-MB231 cells were collected by trypsinization, counted, and plated in a 96-well black clear-bottom culture plate (Corning Life Sciences, Pittston, Pa.) at a density of $1\times10^3$ cells per well. After 1 day, AuNPs ($2.52\times10^8$ particles) were added and incubated for 12 hours. Cells were then washed three times with PBS and cultured in phenol red-free medium and imaged with a fluorescence microscopy at the time points indicated. In a separate set of experiment, cells were treated with CellTrackers, CM-DiI (2 µM), or CMTMR (7.5 µM, Invitrogen). One day after cell seeding, HeLa and MDA-MB231 cells were incubated with CM-DiI for 5 minutes at 37° C. and then further incubated at 4° C. for an additional 15 minutes according to manufacturer's protocol. After removing the medium, the cells were then incubated for an additional 15 minutes at 4° C. For CMTMR study, cells were incubated with CMTMR for 30 minutes at 37° C. and the medium was then replaced with fresh medium and incubated for a further 30 minutes. After labeling with CM-DiI or CMTMR, cells were washed three times with PBS and cultured in phenol red-free medium and imaged under a fluorescence microscopy as indicated.

Cytotoxicity Assessment of the Multilayered Fluorescent AuNPs.

A cell proliferation assay was performed to assess the cytotoxicity of the various treatments. Briefly, HeLa and MDA-MB231 cells were collected by trypsinization, counted, and plated in a 96-well culture plate at a density of $5\times10^3$ cells per well. One day after seeding, AuNPs ($2.52\times10^8$ particles) were added and the cells were cultured for a further 24 hours. At day 2, 20 µl CellTiter solution (Promega) was added to each well and incubated for an additional 3 hours, and then the absorbance of the solution was measured at 490 nm using a Spectramax M2 plate reader (Molecular Devices).

Fluorescence Retention in Jurkat Cells.

Jurkat cells ($1.0\times10^6$ cells) were seeded in a 12-well culture plate (BD Falcon, San Jose, Calif.) together with 5L AuNPs ($1.26\times10^9$ particles) in 400 µl RPMI 1640 medium and cultured for 24 hours in the dark at 37° C. in a 5% $CO_2$ atmosphere. Cells ($4\times10^5$) were then transferred to a FACS tube after three washes with PBS, and the FITC fluorescence signal inside the cells was measured using a BD LSR II flow cytometry (BD Biosciences, San Jose, Calif.). Remaining cells were cultured in 6-well culture plates (BD Falcon) in 4 ml RPMI 1640 medium. The procedure was repeated at different time points, up to 21 days. In a separate set of experiments, Jurkat cells ($1.0\times10^6$) were incubated with CM-DiI (1 µM) or CMTMR (2 µM) following the manufacturer's instructions. On the designated day, the fluorescence signal of CM-DiI or CMTMR was measured using a PE filter set by a BD LSR II flow cytometry.

Assessment of CD3 Expression Profiles and Cytotoxicity after Treatment with 5L AuNPs.

One day after incubating Jurkat cells ($1.0\times10^6$) with 5L AuNPs ($1.26\times10^9$ particles) in a 12-well culture plate in 400 µl RPMI medium, a fraction of the cells ($4\times10^5$) was moved to a FACS tube, followed by three PBS washes. Anti-CD3 antibody (3 µl, Sigma-Aldrich) and SYTOX Blue (2 µl, Invitrogen) in 1 ml PBS were added according to the manufacturer's instructions. PE fluorescence for CD3 expression and DAPI for cytotoxicity in Jurkat cells were measured for up to 7 days using a BD LSR II flow cytometry.

Results

A labeling nanoprobe was prepared with multiple layers of polyelectrolytes, sequentially assembled on an inert AuNP, using alternating charged polymers (FIG. 22A). The negatively charged polyelectrolyte used was polyacrylic acid (PAA), and the positively charged layer was biodegradable poly-L-lysine (PLL) decorated with fluorescein isothiocyanate (FITC). Because the positively charged lysine residues in PLL can be degraded by many intracellular proteases, such as cathepsins B and L, PLL was selected as the backbone to provide a slow-release capability. When multiple FITC residues were loaded onto one PLL backbone, self-quenching occurred due to the close proximity of neighboring fluorochromes. Importantly though, this quenched signal could be recovered on proteolytic degradation of the PLL backbone. The optimal loading ratio (FITC/PLL=10/1) that provided the maximum quenching/dequenching effect and protease accessibility was determined from a series of PLL conjugates with differing amounts of FITC. A greater than 34-fold change in fluorescence signal was observed upon treatment with a model protease, trypsin (FIG. 23A). Higher loading of FITC provided no further benefit. For comparison, FITC was also loaded on a non-degradable poly-D-lysine (PDL) at the same ratio (FITC/PDL=10/1) and treated in the same way. As expected, the fluorescence signal was not increased (FIG. 23B), suggesting that proteolysis is required to release the quenched fluorescence signal.

To assemble the multilayered fluorescent AuNPs, the negatively charged AuNPs (40 nm) in water were dropped into the positively charged PLL-FITC solution (average $M_w$=50 kDa) for the first layer of coating. The reaction mixture was incubated for 30 minutes, and then the coated particles were spun down by centrifugation. After three washes with sterilized water, the PLL-FITC-coated AuNPs (1L AuNPs) were added to the negatively charged PAA ($M_w$=15 kDa) solution. By repeating these procedures (FIG. 22A), multilayered AuNPs—up to five layers of PLL-FITC and four layers of PAA (5L AuNPs)—were successfully fabricated by electrostatic interactions. The successful alternating layers of charged polyelectrolytes were evidenced by the zigzag pattern of the surface zeta potentials (FIG. 22B). The PLL coating brought the surface charge from negative to positive, whereas the PAA coating switched it from positive to negative. The hydrodynamic diameter of the prepared AuNPs was measured by dynamic light scattering (DLS) after coating with each layer. The size of initial bare AuNPs was 40 nm and the prepared particle size increased steadily with the number of layers (1L: 63 nm; 3L: 112 nm; 5L: 144 nm) (FIG. 22C).

AuNPs prepared with different number of layers were then subjected to protease activation. As shown in FIG. 22D, particles were stable in phosphate-buffered saline (PBS), but when treated with protease, the fluorescence signal change was layer-dependent. The optimal formulation was 5L AuNPs (five layers of PLL and four layers of PAA), the fluorescence of which changed by 195-fold. The fluorescence signal change of 7L AuNPs, however, was similar to that of 5L AuNPs despite the two additional layers of PLL-FITC added to the particles. Under the same conditions, when protease-resistant PDL-FITC was used in the assembly, no fluorescence change was seen with the PDL-FITC coated AuNPs (5D AuNPs, five layers of PDL and four layers of PAA), as observed with the free PDL-FITC peptide (FIG. 23B), again suggesting that protease degradation is required to release the packed fluorochromes. Comparing the protease-induced fluorescence changes between free PLL-FITC and assembled particle, a much larger change was seen with the assembled particles. This was presumably caused by the layer-by-layer packing, because fluorescence quenching could occur not only within each PLL molecule, but also between layers. Additionally, the kinetics of the fluorescence release of the nanoprobes was much slower than that of free PLL-FITC molecules, suggesting the protease required more time to digest the tightly packed layers.

The ability of the multilayered fluorescent nanoprobe to label live cells was investigated by comparing the nanoprobe with commercially available cell labeling reagents, CM-DiI and CMTMR, using fluorescence microscopy. HeLa cells were incubated with cell trackers and various multilayered fluorescent nanoprobes (FIG. 24). When incubated with CMTMR, the fluorescence signal was strong at short time points but decreased quickly and lasted only for 2 days (FIG. 24A). When incubated with 3L AuNPs, the intracellular fluorescence signal was sustained for approximately 3 days (FIG. 24B). However, a prolonged fluorescence signal was found with 5L AuNPs. A high fluorescence signal was maintained for more than 14 days with negligible background (FIG. 24C). CM-DiI, PLL-FITC without AuNPs, and 1L AuNPs were also tested with HeLa cells; however, their signal strengths were much weaker than that of the 5L AuNPs (FIG. 25). As expected, there was no signal when non-degradable 5D AuNPs were used (FIG. 24D). Similar signal patterns were seen with MDA-MB231 cells using either commercially available cell trackers or our multilayered fluorescent nanoprobes (FIG. 26). However, in MDA-MB231 cells, the fluorescence signal could only be followed for 5 days, because of the fast growing nature of MDA-MB 231 cells. Among the probes tested, only 5L AuNPs could maintain a strong fluorescence signal to day 5 in MDA-MB231 cells. The cytotoxicity of the prepared multilayered fluorescent nanoprobes was evaluated in HeLa (FIG. 24F) and MDA-MB231 (FIG. 26G) cells. No significant toxicity was detected in any nanoprobe-treated cells.

To gain a better understanding of signal retention after cell division, a suspension of the Jurkat T cell line was tested with 5L AuNPs (FIG. 27A) or the commercially available cell tracking agents, CM-DiI and CMTMR (FIGS. 27B and 27C). After incubation with various labels, aliquots of cells were collected and analyzed by flow cytometry (FIG. 29). The initial fluorescence intensity of each label was controlled to a similar level for a fair comparison. Similar retention patterns were seen with the CM-DiI and CMTMR cell trackers. The intensity in CM-DiI- and CMTMR-treated cells had declined to 8-% and 3-% of the original intensity, respectively, after 4 days of incubation. At day 7, the labels were largely gone, and the signal had declined to a background level. As the doubling time of the Jurkat T cell line is approximately 48 hours, this result suggested the label lasted for about three divisions. In contrast, the 5L AuNPs offered a much longer signal duration. At day 4, the signal intensity was still 24-%. At days 7 and 14, the signal had declined to 12-% and 7-%, respectively. Even after 21 days, the 4-% remaining signal was still detectable by FACS. These results suggest that the slow release mechanism prolonged the duration of action of the cell labels and that the nanoparticles were suitable for labeling dividing cells.

The potential toxicity of the nanoprobes in Jurkat cells was further assessed by monitoring a T-cell-specific surface marker. Specifically, after treatment with 5L AuNPs, cells were stained with an anti-CD3-phycoerythrin (PE) antibody and SYTOX Blue to confirm cell phenotypic integrity and viability, respectively. No significant difference between 5L AuNPs-treated and non-treated cells was seen up to 7 days (FIGS. 28B and 28C), indicating the safety of this long-lasting nanoprobe.

In summary, the tightly packed polyelectrolytes showed slow proteolytic degradation, so that the attached fluorochromes were not released at once, and this slow-release process resulted in a constant supply of fluorochromes, maintaining the intracellular fluorescence signal at a high level for a prolonged time. Because each particle acts as a reservoir, the developed nanoprobe also worked well with dividing cells. During division, the nanoprobes could be distributed into daughter cells, and then refilled the daughter cells with newly released fluorochromes (FIG. 28D). The long-lasting labeling strategy developed could have enormous potential in in vivo tracking of cells, because the intracellular fluorescence signal lasts for weeks, much longer than current labeling approaches.

What is claimed is:

1. A polypeptide comprising:
   (a) a fluorescent donor moiety;
   (b) an energy acceptor moiety;
   (c) an amino acid sequence comprising a Leucine-Proline or a Leucine-X-Proline linkage at a scissile bond of the polypeptide, wherein X is an amino acid residue, wherein the amino acid sequence comprising the Leucine-Proline or Leucine-X-Proline linkage is between the fluorescent donor moiety and the energy acceptor moiety, wherein the scissile bond is selectively cleaved by cathepsin E, and wherein cleavage of the scissile bond results in fluorescence, wherein the amino acid sequence is selected from the group consisting of Ala-Gly-Phe-Ser-Leu-Pro-Ala-Lys-Arg (SEQ ID NO:1); SEQ ID NO:1 with up to two conservative amino acid substitutions in the sequence, except for Leu-Pro; Phe-Ser-Leu-Pro-Ala (SEQ ID NO:2); SEQ ID NO:2 with up to two conservative amino acid substitutions in the sequence, except for Leu-Pro; Phe-Ser-Leu-X-Pro-Ala (SEQ ID NO:3); SEQ ID NO:3 with up to two conservative amino acid substitutions in the sequence, except for the Leucine and Proline in Leu-X-Pro; Ala-Gly-Phe-Ser-Leu-Gly-Pro-Lys-Arg (SEQ ID NO:4); and SEQ ID NO:4 with up to two conservative amino acid substitutions in the sequence, except for the Leucine and Proline in Leu-Gly-Pro.

2. The polypeptide of claim 1, wherein the fluorescent donor moiety and the energy acceptor moiety are the same moiety.

3. The polypeptide of claim 1, wherein the fluorescent donor moiety or the energy acceptor moiety are linked to the polypeptide by a spacer.

4. The polypeptide of claim 1, wherein the fluorescent donor moiety or energy acceptor moiety is covalently linked to the N-terminal Ala of SEQ ID NO:1, is covalently linked to the Lys of SEQ ID NO:1, is covalently linked to the Ala of SEQ ID NO:4 or SEQ ID NO:4 with up to two conservative amino acid substitutions, or is covalently linked to the Lys of SEQ ID NO:4 or SEQ ID NO:4 with up to two conservative amino acid substitutions.

5. The polypeptide of claim 1, wherein the amino acid sequence comprises SEQ ID NO:1.

6. The polypeptide of claim 1, wherein the amino acid sequence comprises SEQ ID NO:4.

7. A method of detecting cathepsin E comprising:
   (a) contacting the cathepsin E with the polypeptide of claim 1;
   (b) detecting fluorescence, wherein fluorescence indicates the presence of cathepsin E.

8. The method of claim 7, wherein the contacting step is performed in vivo.

9. The method of claim 7, wherein the contacting step is performed in vitro.

10. The method of claim 7, wherein the fluorescent donor moiety and the energy acceptor moiety are the same moiety.

11. The method of claim 7, wherein the amino acid sequence of the polypeptide is selected from the group consisting of Phe-Ser-Leu-Pro-Ala (SEQ ID NO:2); SEQ ID NO:2 with up to two conservative amino acid substitutions in the sequence, except for Leu-Pro; Phe-Ser-Leu-X-Pro-Ala (SEQ ID NO:3); and SEQ ID NO:3 with up to two conservative amino acid substitutions in the sequence, except for Leucine and Proline, in Leu-X-Pro.

12. The method of claim 11, wherein the fluorescent donor moiety or the energy acceptor moiety are linked to the polypeptide by a spacer.

13. The method of claim 7, wherein the fluorescent donor moiety or the energy acceptor moiety is covalently linked to the N-terminal Ala of SEQ ID NO:1 or SEQ ID NO:1 with up to two conservative amino acid substitutions, is covalently linked to the Lys of SEQ ID NO:1 or SEQ ID NO:1 with up to two conservative amino acid substitutions, is covalently linked to the Ala of SEQ ID NO:4 or SEQ ID NO:4 with up to two conservative amino acid substitutions, or is covalently linked to the Lys of SEQ ID NO:4 or SEQ ID NO:4 with up to two conservative amino acid substitutions.

14. The method of claim 7, wherein the amino acid sequence comprises SEQ ID NO:1.

15. The method of claim 7, wherein the amino acid sequence comprises SEQ ID NO:4.

16. The method of claim 7, wherein the cathepsin E is in a cell.

17. The method of claim 16, wherein the cell is a cancer cell.

18. A method of diagnosing a cathepsin-E related cancer or detecting a pre-cancerous condition of a cathepsin-E related cancer in a subject, the method comprising:
(a) contacting a cell of the subject with the polypeptide of claim 1;
(b) detecting fluorescence in the cell above background, wherein fluorescence in the subject above background indicates the subject has cancer or a pre-cancerous condition.

19. The method of claim 18, wherein the contacting step is performed in vivo.

20. The method of claim 18, wherein the contacting step is performed in vitro.

21. The method of claim 18, wherein the fluorescent donor moiety and the energy acceptor moiety are the same moiety.

22. The method of claim 18, wherein the amino acid sequence of the polypeptide is selected from the group consisting of Phe-Ser-Leu-Pro-Ala (SEQ ID NO:2); SEQ ID NO:2 with up to two conservative amino acid substitutions in the sequence, except for Leu-Pro; Phe-Ser-Leu-X-Pro-Ala (SEQ ID NO:3); and SEQ ID NO:3 with up to two conservative amino acid substitutions in the sequence, except for Leucine and Proline, in Leu-X-Pro.

23. The method of claim 22, wherein the fluorescent donor moiety or the energy acceptor moiety are linked to the polypeptide by a spacer.

24. The method of claim 18, wherein the fluorescent donor moiety or the energy acceptor moiety is covalently linked to the N-terminal Ala of SEQ ID NO:1 or SEQ ID NO:1 with up to two conservative amino acid substitutions, is covalently linked to the Lys of SEQ ID NO:1 or SEQ ID NO:1 with up to two conservative amino acid substitutions, is covalently linked to the Ala of SEQ ID NO:4 or SEQ ID NO:4 with up to two conservative amino acid substitutions, or is covalently linked to the Lys of SEQ ID NO:4 or SEQ ID NO:4 with up to two conservative amino acid substitutions.

25. The method of claim 18, wherein the amino acid sequence comprises SEQ ID NO:1.

26. The method of claim 18, wherein the amino acid sequence comprises SEQ ID NO:4.

27. The method of claim 18, wherein the cancer or pre-cancerous condition are selected from the group consisting of a pancreatic ductal adenocarcinoma, a cervical adenocarcinoma, a gastric adenocarcinoma, a prostate cancer, a colorectal cancer, a lung carcinoma, a breast cancer, an andenoendocrine carcinoma, a neuroendocrine positive tumor, and pre-cancerous conditions thereof.

28. The method of claim 18, wherein the subject has been previously treated for cancer.

29. A method of monitoring the effectiveness of a cancer treatment in a subject being treated for a cathepsin-E related cancer, the method comprising:
(a) contacting a cell of the subject at various time points with the polypeptide of claim 1; and
(b) detecting a level of fluorescence in the cell, wherein a decreasing level of fluorescence indicating that the treatment is effective, and wherein an unchanged or increasing level of fluorescence indicating that the treatment is ineffective.

30. The method of claim 29, wherein the contacting step is performed in vivo.

31. The method of claim 29, wherein the contacting step is performed in vitro.

32. The method of claim 29, wherein the fluorescent donor moiety and the energy acceptor moiety are the same moiety.

33. The method of claim 29, wherein the amino acid sequence of the polypeptide is selected from the group consisting of Phe-Ser-Leu-Pro-Ala (SEQ ID NO:2); SEQ ID NO:2 with up to two conservative amino acid substitutions in the sequence, except for Leu-Pro; Phe-Ser-Leu-X-Pro-Ala (SEQ ID NO:3); and SEQ ID NO:3 with up to two conservative amino acid substitutions in the sequence, except for Leucine and Proline, in Leu-X-Pro.

34. The method of claim 33, wherein the fluorescent donor moiety or the energy acceptor moiety are linked to the polypeptide by a spacer.

35. The method of claim 29, wherein the fluorescent donor moiety or the energy acceptor moiety is covalently linked to the N-terminal Ala of SEQ ID NO:1 or SEQ ID NO:1 with up to two conservative amino acid substitutions, is covalently linked to the Lys of SEQ ID NO:1 or SEQ ID NO:1 with up to two conservative amino acid substitutions, is covalently linked to the Ala of SEQ ID NO:4 or SEQ ID NO:4 with up to two conservative amino acid substitutions, or is covalently linked to the Lys of SEQ ID NO:4 or SEQ ID NO:4 with up to two conservative amino acid substitutions.

36. The method of claim 29, wherein the amino acid sequence comprises SEQ ID NO:1.

37. The method of claim 29, wherein the amino acid sequence comprises SEQ ID NO:4.

38. The method of claim 29, wherein the cancer is selected from the group consisting of a pancreatic ductal adenocarcinoma, a cervical adenocarcinoma, a gastric adenocarcinoma, a prostate cancer, a colorectal cancer, a lung carcinoma, a breast cancer, an adenoendocrine carcinoma, and a neuroendocrine positive tumor.

39. A polypeptide comprising an amino acid sequence comprising a Leucine-Proline or a Leucine-X-Proline linkage at a scissile bond of the polypeptide, wherein X is an amino acid residue, wherein the scissile bond is selectively cleaved by cathepsin E, wherein cleavage of the scissile bond results in fluorescence, and wherein the amino acid sequence is selected from the group consisting of Ala-Gly-Phe-Ser-Leu-Pro-Ala-Lys-Arg (SEQ ID NO:1) and SEQ ID NO:1 with up to two conservative amino acid substitutions in the sequence, except for Leu-Pro.

40. A polypeptide comprising an amino acid sequence comprising a Leucine-Proline or a Leucine-X-Proline linkage at a scissile bond of the polypeptide, wherein the scissile bond is selectively cleaved by cathepsin E, wherein cleavage of the scissile bond results in fluorescence, and wherein the amino acid sequence is selected from the group consisting of Phe-Ser-Leu-Pro-Ala (SEQ ID NO:2) and SEQ ID NO:2 with up to two conservative amino acid substitutions in the sequence, except for Leu-Pro.

41. A polypeptide comprising an amino acid sequence comprising a Leucine-Proline or a Leucine-X-Proline linkage at a scissile bond of the polypeptide, wherein X is an amino acid residue, wherein the scissile bond is selectively cleaved by cathepsin E, wherein cleavage of the scissile bond results in fluorescence, and wherein the amino acid sequence is selected from the group consisting of Phe-Ser-Leu-X-Pro-Ala (SEQ ID NO:3) and SEQ ID NO:3 with up to two conservative amino acid substitutions in the sequence, except for the Leucine and Proline, in Leu-X-Pro.

42. A polypeptide comprising an amino acid sequence comprising a Leucine-Proline or a Leucine-X-Proline linkage at a scissile bond of the polypeptide, wherein X is an amino acid residue, wherein the scissile bond is selectively cleaved by cathepsin E, wherein cleavage of the scissile bond results in fluorescence, and wherein the amino acid sequence is selected from the group consisting of Ala-Gly-Phe-Ser-Leu-Gly-Pro-Lys-Arg (SEQ ID NO:4); and SEQ ID NO:4 with up to two conservative amino acid substitutions in the sequence, except for the Leucine and Proline, in Leu-Gly-Pro.

* * * * *

SEQUENCE LISTING

<160> NUMBER OF SEQ ID NOS: 29

<210> SEQ ID NO 1
<211> LENGTH: 9
<212> TYPE: PRT
<213> ORGANISM: Artificial Sequence
<220> FEATURE:
<223> OTHER INFORMATION: Artificial Construct

<400> SEQUENCE: 1

Ala Gly Phe Ser Leu Pro Ala Lys Arg
1               5

<210> SEQ ID NO 2
<211> LENGTH: 5
<212> TYPE: PRT
<213> ORGANISM: Artificial Sequence
<220> FEATURE:

<223> OTHER INFORMATION: Artificial Construct

<400> SEQUENCE: 2

Phe Ser Leu Pro Ala
1               5

<210> SEQ ID NO 3
<211> LENGTH: 6
<212> TYPE: PRT
<213> ORGANISM: Artificial Sequence
<220> FEATURE:
<223> OTHER INFORMATION: Artificial Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 3

Phe Ser Leu Xaa Pro Ala
1               5

<210> SEQ ID NO 4
<211> LENGTH: 9
<212> TYPE: PRT
<213> ORGANISM: Artificial Sequence
<220> FEATURE:
<223> OTHER INFORMATION: Artificial Construct

<400> SEQUENCE: 4

Ala Gly Phe Ser Leu Gly Pro Lys Arg
1               5

<210> SEQ ID NO 5
<211> LENGTH: 9
<212> TYPE: PRT
<213> ORGANISM: Artificial Sequence
<220> FEATURE:
<223> OTHER INFORMATION: Artificial Construct

<400> SEQUENCE: 5

Gly Ser Pro Ala Phe Leu Ala Lys Arg
1               5

<210> SEQ ID NO 6
<211> LENGTH: 11
<212> TYPE: PRT
<213> ORGANISM: Artificial Sequence
<220> FEATURE:
<223> OTHER INFORMATION: Artificial Construct

<400> SEQUENCE: 6

Gly Pro Ile Leu Phe Phe Arg Leu Gly Lys Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Artificial Construct

<400> SEQUENCE: 7

Gly Pro Ile Leu Phe Phe Arg Leu Lys Arg
1               5                   10

<210> SEQ ID NO 8
<211> LENGTH: 8

```
<212> TYPE: PRT
<213> ORGANISM: Artificial Sequence
<220> FEATURE:
<223> OTHER INFORMATION: Artificial Construct

<400> SEQUENCE: 8

Gly Ser Ser Ala Phe Leu Ala Phe
1               5

<210> SEQ ID NO 9
<211> LENGTH: 8
<212> TYPE: PRT
<213> ORGANISM: Artificial Sequence
<220> FEATURE:
<223> OTHER INFORMATION: Artificial Construct

<400> SEQUENCE: 9

Lys Pro Ile Leu Phe Phe Arg Leu
1               5

<210> SEQ ID NO 10
<211> LENGTH: 8
<212> TYPE: PRT
<213> ORGANISM: Artificial Sequence
<220> FEATURE:
<223> OTHER INFORMATION: Artificial Construct

<400> SEQUENCE: 10

Lys Pro Ile Ser Phe Phe Arg Leu
1               5

<210> SEQ ID NO 11
<211> LENGTH: 8
<212> TYPE: PRT
<213> ORGANISM: Artificial Sequence
<220> FEATURE:
<223> OTHER INFORMATION: Artificial Construct

<400> SEQUENCE: 11

Lys Pro Ile Leu Phe Phe Arg Leu
1               5

<210> SEQ ID NO 12
<211> LENGTH: 8
<212> TYPE: PRT
<213> ORGANISM: Artificial Sequence
<220> FEATURE:
<223> OTHER INFORMATION: Artificial Construct

<400> SEQUENCE: 12

Lys Pro Ile Ile Phe Phe Arg Leu
1               5

<210> SEQ ID NO 13
<211> LENGTH: 8
<212> TYPE: PRT
<213> ORGANISM: Artificial Sequence
<220> FEATURE:
<223> OTHER INFORMATION: Artificial Construct

<400> SEQUENCE: 13

Lys Pro Ile Met Phe Phe Arg Leu
1               5

<210> SEQ ID NO 14
<211> LENGTH: 8
<212> TYPE: PRT
```

```
<213> ORGANISM: Artificial Sequence
<220> FEATURE:
<223> OTHER INFORMATION: Artificial Construct

<400> SEQUENCE: 14

Lys Pro Ile Leu Phe Phe Arg Leu
1               5

<210> SEQ ID NO 15
<211> LENGTH: 8
<212> TYPE: PRT
<213> ORGANISM: Artificial Sequence
<220> FEATURE:
<223> OTHER INFORMATION: Artificial Construct

<400> SEQUENCE: 15

Lys Pro Ile Cys Phe Phe Arg Leu
1               5

<210> SEQ ID NO 16
<211> LENGTH: 8
<212> TYPE: PRT
<213> ORGANISM: Artificial Sequence
<220> FEATURE:
<223> OTHER INFORMATION: Artificial Construct

<400> SEQUENCE: 16

Pro Ile Leu Phe Phe Arg Leu Lys
1               5

<210> SEQ ID NO 17
<211> LENGTH: 19
<212> TYPE: RNA
<213> ORGANISM: Artificial Sequence
<220> FEATURE:
<223> OTHER INFORMATION: Artificial Construct

<400> SEQUENCE: 17
cguacgcgga auacuucga                                         19

<210> SEQ ID NO 18
<211> LENGTH: 19
<212> TYPE: RNA
<213> ORGANISM: Artificial Sequence
<220> FEATURE:
<223> OTHER INFORMATION: Artificial Construct

<400> SEQUENCE: 18
ucgaaguauu ccgcguacg                                         19

<210> SEQ ID NO 19
<211> LENGTH: 19
<212> TYPE: RNA
<213> ORGANISM: Artificial Sequence
<220> FEATURE:
<223> OTHER INFORMATION: Artificial Construct

<400> SEQUENCE: 19
agcuucauaa ggcgcaugc                                         19

<210> SEQ ID NO 20
<211> LENGTH: 19
<212> TYPE: RNA
<213> ORGANISM: Artificial Sequence
<220> FEATURE:
<223> OTHER INFORMATION: Artificial Construct
```

```
<400> SEQUENCE: 20
gcaugcgccu uaugaagcu                                                 19

<210> SEQ ID NO 21
<211> LENGTH: 5
<212> TYPE: PRT
<213> ORGANISM: Artificial Sequence
<220> FEATURE:
<223> OTHER INFORMATION: Artificial Construct

<400> SEQUENCE: 21

Ala Gly Phe Ser Leu
1               5

<210> SEQ ID NO 22
<211> LENGTH: 4
<212> TYPE: PRT
<213> ORGANISM: Artificial Sequence
<220> FEATURE:
<223> OTHER INFORMATION: Artificial Construct

<400> SEQUENCE: 22

Pro Ala Lys Arg
1

<210> SEQ ID NO 23
<211> LENGTH: 23
<212> TYPE: DNA
<213> ORGANISM: Artificial Sequence
<220> FEATURE:
<223> OTHER INFORMATION: Artificial Construct

<400> SEQUENCE: 23
tcaccttcac cattaacgga gtc                                            23

<210> SEQ ID NO 24
<211> LENGTH: 21
<212> TYPE: DNA
<213> ORGANISM: Artificial Sequence
<220> FEATURE:
<223> OTHER INFORMATION: Artificial Construct

<400> SEQUENCE: 24
gcattccatc cacgaagtcc a                                              21

<210> SEQ ID NO 25
<211> LENGTH: 24
<212> TYPE: DNA
<213> ORGANISM: Artificial Sequence
<220> FEATURE:
<223> OTHER INFORMATION: Artificial Construct

<400> SEQUENCE: 25
ccctcagccc aactgcctac accc                                           24

<210> SEQ ID NO 26
<211> LENGTH: 24
<212> TYPE: DNA
<213> ORGANISM: Artificial Sequence
<220> FEATURE:
<223> OTHER INFORMATION: Artificial Construct

<400> SEQUENCE: 26
aaggagagaa ggatattcct ggac                                           24
```

```
<210> SEQ ID NO 27
<211> LENGTH: 24
<212> TYPE: DNA
<213> ORGANISM: Artificial Sequence
<220> FEATURE:
<223> OTHER INFORMATION: Artificial Construct

<400> SEQUENCE: 27
aagggctttc ttacaacata ctgg                                              24

<210> SEQ ID NO 28
<211> LENGTH: 24
<212> TYPE: DNA
<213> ORGANISM: Artificial Sequence
<220> FEATURE:
<223> OTHER INFORMATION: Artificial Construct

<400> SEQUENCE: 28
tgatactaca gtgcctcgcc gcct                                              24

<210> SEQ ID NO 29
<211> LENGTH: 9
<212> TYPE: PRT
<213> ORGANISM: Artificial Sequence
<220> FEATURE:
<223> OTHER INFORMATION: Artificial Construct

<400> SEQUENCE: 29

Ala Gly Phe Ser Leu Pro Ala Gly Cys
1               5
```